US008168664B2

(12) United States Patent
Roberts et al.

(10) Patent No.: US 8,168,664 B2
(45) Date of Patent: *May 1, 2012

(54) METAXALONE PRODUCTS, METHOD OF MANUFACTURE, AND METHOD OF USE

(75) Inventors: Richard H. Roberts, Lakewood, NJ (US); Jie Du, Lansdale, PA (US); Matthew W. Davis, Erwinna, PA (US)

(73) Assignee: Mutual Pharmaceutical Company, Inc., Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/784,738

(22) Filed: May 21, 2010

(65) Prior Publication Data
US 2011/0065721 A1    Mar. 17, 2011

Related U.S. Application Data

(63) Continuation of application No. 12/127,930, filed on May 28, 2008, now abandoned, which is a continuation-in-part of application No. 11/349,534, filed on Feb. 6, 2006, now abandoned.

(60) Provisional application No. 60/726,861, filed on Oct. 14, 2005.

(51) Int. Cl.
*A61K 31/42* (2006.01)
(52) U.S. Cl. ...................................................... 514/376
(58) Field of Classification Search .................... 514/376
See application file for complete search history.

(56) References Cited

U.S. PATENT DOCUMENTS

| | | | |
|---|---|---|---|
| 3,062,827 A | 11/1962 | Lunsford | |
| 4,254,129 A | 3/1981 | Carr et al. | |
| 6,407,128 B1 | 6/2002 | Scaife et al. | |
| 6,683,102 B2 | 1/2004 | Scaife et al. | |
| 7,122,566 B1 | 10/2006 | Du et al. | |
| 7,378,434 B2 | 5/2008 | Du et al. | |
| 2004/0265889 A1 | 12/2004 | Durham et al. | |

OTHER PUBLICATIONS de Morais, S. M. F et al., The Major Genetic Defect Responsible for the Polymorphism of S-Mephenytoin Metabolism in Humans, J. Biol. Chem., 1994; vol. 269, No. 22, pp. 15419-15422.
Bruce, R.B. et al., Metabolism of Mextaxalone, J. Med Chem, 1966; vol. 9, pp. 286-288.
Sahi, J. et al., Comparative Effects of Thiazolidinediones on In Vitro P450 Enzyme Induction and Inhibition, Drug Metab. Dispos., 2003: vol. 31 (4) pp. 439-446.
Albanese, J. A., Metaxalone, Nurses Drug Reference, 2nd Ed., 1982; McGraw-Hill Book Company, New York, p. 427.
Abrams, A. C., Clinical Drug Therapy, 4th Ed., 1995; J.B. Lippincott Company, Philadelphia, pp. 145-149.
Korzekwa, K R., In vitro enzyme kinetics applied to drug-metabolizing enzymes in Drug-Drug Interactions, ed. A.D. Rodrigues, Chapter 2, Marcel Dekker, Inc., New York, 2002, pp. 33-54.
Clarke, S. E., Human Cytochromes P450 and their role in metabolism-based drug-drug Interactions, Drug-Drug Interactions, ed. A.D. Rodrigues, Chapter 3, Marcel Dekker, Inc., New York, 2002, pp. 55-88.
Silva, J.M. et al., In Vitro models for Studying Induction of Cytrochrome P450 Enzymes, Drug-Drug Interactions, ed. A. D. Rodrigues, Chapter 6, Marcel Dekker, Inc., New York, 2002, pp. 189-216.
Madan, A. et al., In vitro approaches for studying the inhibition of drug-metabolizing enzymes and identifying the drug-metabolizing enzymes responsible for the metabolism of Drugs, Drug-Drug Interactions, ed. A.D. Rodrigues, Chapter 7, Marcel Dekker, Inc., New York, 2002, pp. 217-294.
Wilkinson, G. R., In Vivo Probes for Studying Induction and Inhibition of Cytochrome P450 Enzymes in Humans, Drug-Drug Interactions, ed. A.D. Rodrigues, Chapter 12, Marcel Dekker, Inc., New York, 2002, pp. 439-504.
Carlson, S.P. et al., Development of a metabolic drug interaction database at the University of Washington, Drug-Drug Interactions, ed. A.D. Rodrigues, Chapter 14, Marcel Dekker, Inc., New York, 2002, pp. 549-563.
Greenblatt, D.J. et al., Drug-Drug interactions: Clinical perspective, Drug-Drug Interactions, ed. A.D. Rodrigues, Chapter 15, Marcel Dekker, Inc., New York, 2002, pp. 565-584.
Huang, S. et al., An integrated approach to assessing drug-drug interactions: a regulatory perspective, Drug-Drug Interactions, ed. A.D. Rodrigues, Chapter 17, Marcel Dekker, Inc., New York, 2002, pp. 605-632.
Yuan. R. et al., Evaluation of Cytochrome P450 Probe Substrates Commonly Used by the Pharmaceutical Industry to Study in Vitro Drug Interactions, Drug Metab. Dispos., 2002; vol. 30 (12), pp. 1311-1319.
Goshman, L. et al., Clinically significant Cytochrome P450 drug interactions, J. Pharm. Soc. Wisconsin, May-Jun. 1999; pp. 23-38.
Fathie, K., A Second Look at a Skeletal Muscle Relaxant; A Double-Blind Study of Metaxalone, Curr. Ther. Res 1964; vol. 6 (II), pp. 677-683.
Jesic, R. et al., Modern Functional Diagnostics in Liver Diseases, Arch Gastroentrohepatol 2001; vol. 20 (1-2), pp. 35-37.
NORVIR, Physicians' Desk Reference, 57th Edition, Thompson PDR, Montvale, N.J., 2003, pp. 482-489.
SKELAXIN, Physicians' Desk Reference, 57th Edition, Thompson PDR, Montvale, N.J., 2003, p. 1274.

(Continued)

*Primary Examiner* — Raymond Henley, III
(74) *Attorney, Agent, or Firm* — Cantor Colburn LLP

(57) ABSTRACT

Disclosed herein are methods of using metaxalone. In one embodiment, the method comprises determining that a patient in need metaxalone therapy is taking a substance that is a n inhibitor or an inducer of a cytochrome p450 isozyme, wherein the cytochrome P450 is CYP1A2, CYP2C8, CYP2C9, CYP2C19, CYP2D6, CYP2E1, or CYP3A4, and adjusting administration to the patient of metaxalone or the substance to avoid an adverse event associated with metaxalone. In another embodiment, the method comprises informing a user that metaxalone is metabolized by a cytochrome p450 isozyme, wherein the cytochrome P450 is CYP1A2, CYP2C8, CYP2C9, CYP2C19, CYP2D6, CYP2E1, or CYP3A4. Also included are articles of manufacture comprising a container containing a dosage form of metaxalone, wherein the container is associated with published material informing that metaxalone affects activity of a cytochrome p450 isozyme. Also disclosed are a method of treatment and a method of manufacturing a metaxalone product.

24 Claims, No Drawings

OTHER PUBLICATIONS

Waldman, H.J., Centrally acting skeletal muscle relaxants and associated drugs, J. Pain Symptom Mgmt.,1994; vol. 9 (7), pp. 434-441.

Walsky, R.L. et al., Validated Assays for Human Cytochrome P450 Activities, Drug Metab. Dispos., 2004; vol. 32 (6), pp. 647-660.

Walsky, R.L. et al., Examination of 209 drugs for inhibition of Cytochrome P450 2C8, J Clin Pharmacol. 2005; vol. 45 (1), pp. 68-78.

Tredger, J.M. et al., Cytochromes P450—Their impact on drug treatment, Hosp Pharm 2002; vol. 9: pp. 167-173.

Skeletal Muscle Relaxants (Systemic), USP DI, Drug Information for the Health Care Professional., 16th Ed., U.S. Pharmacopeial Convention, Inc., Rand McNally, Taunton, MA, 1996; pp. 2634-2637.

Pfeifer, M.A. et al., A highly successful and novel model for treatment of chronic painful diabetic peripheral neuropathy, Diabetes Care, 1993; vol. 16 (8), pp. 1103-1115.

Guidance for Industry, Drug Metabolism/Drug Interaction. Studies in the Drug Development Process: Studies in Vitro, Dept. of Health and Human Services, U.S. Food and Drug Administration, Apr. 1997.

Guidance for Industry, In Vivo Drug Metabolism/Drug Interaction Studies—Study Design, Data Analysis, and. Recommendations for Dosing and Labeling, Dept. of Health and Human Services, U.S. Food and Drug Administration, Nov. 1999.

Flockhart, D.A., Drug Interactions: Cytochrome P450 Drug Interaction Table. Indiana University School of Medicine (Sep. 22, 2004 update). [online] [retrieved from the Internet <URL: web.archive.org/web/20041011210832/http://www.medicine.iupui.edu/flockhart/table.htm> on or before Jun. 23, 2009].

Drug Interaction Studies—Study Design, Data Analysis, and implications for Dosing and Labeling—Preliminary Concept Paper, Dept. of Health and Human Services, U.S. Food and Drug Administration, Oct. 2004.

CRIXIVAN, Physicians' Desk Ref., 57th Edition, Thompson PDR, Montvale, N.J., 2003, pp. 1970-1977.

"Metaxalone", AHFS Drug Information, American Society of Health-System Pharmacists, Bethesda, MD, 2001, pp. 1331-1332.

*King Pharmaceuticals, Inc. et al. v. Sandoz Inc.*, 08-cv-05974 (D.N.J.), doc. 1, Complaint for Patent Infringement, filed Dec. 5, 2008.

*King Pharmaceuticals, Inc. et al. v. Sandoz Inc.*, 08-cv-05974 (D.N.J.), doc. 8, Answer, Defenses, and Counterclaims of Defendant Sandoz, Inc., filed Jan. 13, 2009.

*King Pharmaceuticals, Inc. et al. v. Sandoz Inc.*, 08-cv-05974 (D.N.J.), doc. 9, Plaintiffs' Reply to Defendant's Counterclaims, filed Feb. 5, 2009.

*King Pharmaceuticals, Inc. et al. v. Sandoz Inc.*, 08-cv-05974 (D.N.J.), King Pharmaceuticals, Inc.'s and King Pharmaceuticals Research and Development, Inc.'s Rule 26(a)(1) Initial Disclosures, dated Apr. 9, 2009.

*King Pharmaceuticals, Inc. et al. v. Sandoz Inc.*, 08-cv-05974 (D.N.J.), Initial Disclosures of Sandoz, Inc. Pursuant to Rule 26(a)(1), dated Apr. 8, 2009.

*King Pharmaceuticals, Inc. et al. v. Sandoz Inc.*, 08-cv-05974 (D.N.J.), Pharmaceutical IP Holding, Inc.'s Rule 26(a)(1) Initial Disclosures, dated Apr. 9, 2009.

*King Pharmaceuticals, Inc. et al. v. Sandoz Inc.*, 08-cv-05974 (D.N.J.), Plaintiffs' Preliminary Disclosure of Asserted Claims and Infringement Contentions, Pursuant to L. Pat. R.3.6, dated Jul. 13, 2009.

*King Pharmaceuticals, Inc. et al. v. Sandoz Inc.*, 08-cv-05974 (D.N.J.), Sandoz, Inc.'s Disclosures Pursuant to L. Pat. R.3.6, dated May 22, 2009.

*King Pharmaceuticals, Inc. et al. v. Sandoz Inc.*, 08-cv-05974 (D.N.J.), Sandoz, Inc.'s Identification of Claim Terms to be by Construed by the Court, dated Jun. 5, 2009.

*King Pharmaceuticals, Inc. et al. v. Sandoz Inc.*, 08-cv-05974 (D.N.J.), Plaintiffs' Disclosures of Preliminary Claim Constructions and Related Evidence, dated Jun. 26, 2009.

*King Pharmaceuticals, Inc. et al. v. Sandoz Inc.*, 08-cv-05974 (D.N.J.), Sandoz, Inc.'s Preliminary Claim Constructions, dated Jun. 26, 2009.

*King Pharmaceuticals, Inc. et al. v. Sandoz Inc.*, 08-cv-05974 (D.N.J.), doc. 34, Joint Claim Construction and Prehearing Statement, filed Jul. 27, 2009.

*King Pharmaceuticals, Inc. et al. v. Sandoz Inc.*, 08-cv-05974 (D.N.J.), Plaintiffs' Opening Memorandum in Support of Proposed Claim Construction, dated Oct. 13, 2009.

*King Pharmaceuticals, Inc. et al. v. Sandoz Inc.*, 08-cv-05974 (D.N.J.), Sandoz, Inc.'s Opening Claim Construction Brief, dated Oct. 13, 2009; doc. 40, filed Dec. 14, 2009.

Definitions for "concentration", "condition", "metabolism", "metabolize", "plasma", "receive", "substance", "therapy", Merriam-Webster Online Dictionary, 2009, <http://www.merriam-webstercom/dictionary>.

Definitions for "concentration", "plasma", "treat" in Stedman's Medical Dictionary, 28th ed., Lippincott Williams and Wilkins, Baltimore, MD (2006).

Definitions of "condition", "inform", "affect", "administer"/"administration", "substance", "substrate", "metabolize", "inhibit"/"inhibitor", "induce" in The American Heritage College Dictionary, 3rd ed., Houghton Mifflin Co., Boston (2000).

Definitions of "condition", "inform", "administer"/"administration", "substance", "substrate", "metabolize", "induce" in Compact Oxford Dictionary of Current English, 3rd ed., Oxford University Press, Oxford, UK (2005).

Definition for "compound"/"compounding" in The American Heritage Stedman's Medical Dictionary, Houghton Mifflin Co., Boston (1995), p. 176.

Definition of "substance" in Merriam Webster's Collegiate Dictionary, 11th ed. (2006).

Statement of Law and Facts Alleging Obviousness of U.S. Patent Nos. 7,122,566 and 7,378,434 by Generic Pharmaceutical Company, dated Nov. 5, 2008.

*King Pharmaceuticals, Inc. et al. v. Sandoz Inc.*, 08-cv-05974 (D.N.J.), docs. 41, 41-1, 41-2, 41-3, and 41-4 (Sandoz's Reply Claim Construction Brief, Declaration, Exhibits A, B and C), filed Dec. 14, 2009.

*King Pharmaceuticals, Inc. et al. v. Sandoz Inc.*, 08-cv-05974 (D.N.J.), Plaintiff's Responsive Memorandum in Support of Their Proposed Claim Construction and Supplemental Declaration in Support of Plaintiff's Proposed Claim Construction, dated Dec. 14, 2009.

Beebe, F.A. et al., A Clinical and Pharmacologic review of Skeletal Muscle Relaxants for Musculoskeletal Conditions, Am J Ther. Mar.-Apr. 2005;12(2):151-71.

International Preliminary Report on Patentability dated Mar. 26, 2009 for Application No. PCT/US06/40034.

Bynum, N.D. et al. "Postmortem Distribution of Tramadol, Amitriptyline, and Their Metabolites in a Suicidal Overdose," Journal of Analytical Toxicology (2005) 29(5): 401-406.

Chou, R. et al. "Comparative Efficacy and Safety of Skeletal Muscle Relaxants for Spasticity and Musculoskeletal Conditions: A Systematic Review," J. Pain Symptom Management (2004) 28(2): 140-175.

Elenbaas, J.K., "Centrally Acting Oral Skeletal Muscle Relaxants," Am. J. Hosp. Pharm. (1980) 37(10): 1313-1323.

Gruszecki, A.G. et al., "Polydrug Fatality Involving Metaxalone," J. Forensic Science (2003) 48(2): 432-434.

Kuykendall, J.R. and Rhodes, R.S., "Auditory Hallucinations Elicited by Combined Meclizine and Metaxalone Use at Bedtime," Ann. Pharmacother. (2004) 38(11): 1968-1969.

Moore, K.A. et al., "A Fatality Involving Metaxalone," Forensic Sci. Int. (2005) 149(2-3): 249-251.

Obach, R.S., "Human Liver Aldehyde Oxidase: Inhibition by 239 Drugs," Journal of Clinical Pharmacology (2004) 44 (1): 7-19.

Poklis J.L. et al., "Metaxalone (Skelaxin)-Related Death," Journal of Analytical Toxicology (2004) 28(6): 537-540.

Schafer E.W. et al. "The Acute Oral Toxicity Repellency, and Hazard Potential of 998 Chemicals to One or More Species of Wild Domestic Birds," Archives of Enviroment Contamination and Toxicology (1983) 12(3): 355-382.

Seidler, J. et al., "Identification and Prediction of Promiscuous Aggregating Inhibitors Among Known Drugs," Journal of Medicinal Chemistry (2003) 46(21): 4477-4486.

Toth, P.P. and Urtis J., "Commonly Used Muscle Relaxant Therapies for Acute Low Back Pain: A Review of Carisprodol, Cyclobenzaprine Hydrochloride and Metaxalone," Clinical Therapeutics (2004) 26(9): 1355-1367.

Prescribing Information for SKELAXIN (metaxalone), Aug. 2003, as accessed at www.kingpharm.com on Dec. 21, 2005.

METAXALONE PRODUCTS, METHOD OF MANUFACTURE, AND METHOD OF USE

CROSS-REFERENCE TO RELATED APPLICATIONS

This application is a continuation of U.S. application Ser. No. 12/127,930 filed May 28, 2008, now abandoned, which is a continuation-in-part of U.S. application Ser. No. 11/349,534 filed Feb. 6, 2006, now abandoned, which claims the benefit of U.S. Provisional Application Ser. No. 60/726,861 filed Oct. 14, 2005, each of which is hereby incorporated by reference in its entirety.

BACKGROUND

This application relates to metaxalone products for therapeutic purposes, and in particular to improved methods of use of metaxalone.

Metaxalone, 5-[(3,5-dimethylphenoxy)methyl]-2-oxazolidinone, is used as a skeletal muscle relaxant. The mechanism of action of metaxalone in humans has not been established but may be due to general central nervous system depression.

Metaxalone was approved by the U.S. Food and Drug Administration (FDA) in 1962 as an adjunct to rest, physical therapy, and other measures for the relief of discomforts associated with acute, painful musculoskeletal conditions, such as muscles in spasm. Metaxalone is marketed in the United States under the brand name SKELAXIN®. The dosage forms currently approved for marketing are tablets containing 400 milligrams (mg) or 800 mg of metaxalone. The currently recommended dose for adults and children over 12 years of age is 800 mg, three to four times a day.

Food can affect gastric emptying, and may also alter the release of an active agent from a dosage form, the solubilization of the active agent, and the transport of the active agent across the intestinal wall. For lipophilic, water-insoluble active agents, fatty meals can increase gastric residence time thereby increasing the time available for solubilization and also may enhance the solubilization of the active agent by the lipids contained in the meal. According to U.S. Pat. No. 6,407,128, evaluation of the effect of food on the pharmacokinetics of metaxalone showed that food increased the rate and extent of absorption of a 400 mg oral dosage form in humans.

Studies directed to possible interactions of metaxalone with other active agents have been limited. There have been no detailed studies of the specific enzymes involved in metabolism of metaxalone or of the inhibitory or inducing effects of metaxalone on any Phase I or Phase II metabolic enzymes. In particular, there appear to be no published studies of the inhibitory and inducing effects of metaxalone on particular human cytochrome p450 isozymes or the possible metabolism of metaxalone by particular human cytochrome p450 isozymes.

Several major enzymes and pathways are involved in drug metabolism. Pathways of drug biotransformation are usually divided into two major groups of reactions: Phase I and Phase II metabolism.

Some typical examples of Phase I metabolism include oxidation, hydrolysis and reduction. Examples of Phase I enzymes involved in oxidation reactions are the cytochrome p450 monooxygenase system, the flavin-containing monooxygenase system, alcohol dehydrogenase and aldehyde dehydrogenase, monoamine oxidase, and peroxidases for co-oxidation. Examples of Phase I enzymes involved in reduction are NADPH-cytochrome p450 reductase and reduced (ferrous) cytochrome p450. Examples of Phase I hydrolysis enzymes are epoxide hydrolase, esterases and amidases.

Phase II metabolism involves conjugation reactions. Typical conjugation reactions are glucuronidation, sulfation, amino acid conjugation, acetylation, methylation, and mercapturic acid conjugation. Examples of Phase II metabolic enzymes are glutathione S-transferases (GSTs), mercapturic acid biosynthetic enzymes (transpeptidases, peptidases, and N-acetylases), UDP-glucoron(os)yltransferases, N-acetyltransferases, amino acid N-acyl transferases, and sulfotransferases.

One of the most important groups of Phase I enzymes are the cytochrome p450 monooxygenase system enzymes. The cytochrome p450 enzymes are a highly diverse superfamily of enzymes. NADPH is required as a coenzyme and oxygen is used as a substrate. Each enzyme is termed an isoform or isozyme since each derives from a different gene.

Many members of the cytochrome p450 family are known to metabolize active agents in humans. Active agent interactions associated with metabolism by cytochrome p450 isoforms generally result from enzyme inhibition or enzyme induction. Enzyme inhibition often involves competition between two active agents for the substrate binding site of the enzyme, although other mechanisms for inhibition exist. Enzyme induction occurs when an active agent activates an enzyme or stimulates the synthesis of more enzyme protein, enhancing the enzyme's metabolizing capacity.

Cytochrome p450 isozymes identified as important in active agent metabolism are CYP1A2, CYP2A6, CYP2B6, CYP2C9, CYP2C19, CYP2D6, CYP2E1, and CYP3A4. Examples of cytochrome p450 enzymes known to be involved in active agent interactions are the CYP3A subfamily, which is involved in many clinically significant active agent interactions, including those involving non-sedating antihistamines and cisapride, and CYP2D6, which is responsible for the metabolism of many psychotherapeutic agents, such as thioridazine. CYP3A4 and CYP1A2 enzymes are involved in active agent interactions involving theophylline. CYP2C9, CYP1A2, and CYP2C19 are involved in active agent interactions involving warfarin. Phenytoin and fosphenytoin are metabolized by CYP1A2, CYP2C9, CYP2C19, and CYP3A4; mexiletine is metabolized by CYP2D6 and CYP1A2; and propafenone is metabolized by CYP2D6, CYP3A4, and CYP1A2.

Additionally, several cytochrome p450 isozymes are known to be genetically polymorphic, leading to altered substrate metabolizing ability in some individuals. Allelic variants of CYP2D6 are the best characterized, with many resulting in an enzyme with reduced, or no, catalytic activity. Gene duplication also occurs. As a result, four phenotypic subpopulations of metabolizers of CYP2D6 substrates exist: poor (PM), intermediate (IM), extensive (EM), and ultrarapid (UM). The genetic polymorphisms vary depending on the population in question. For example, Caucasian populations contain a large percentage of individuals who are poor metabolizers, due to a deficiency in CYP2D6—perhaps 5-10% of the population, while only 1-2% of Asians are PMs. CYP2C9, which catalyzes the metabolism of a number of commonly used active agents, including that of warfarin and phenytoin, is also polymorphic. The two most common CYP2C9 allelic variants have reduced activity (5-12%) compared to the wild-type enzyme. Genetic polymorphism also occurs in CYP2C19, for which at least 8 allelic variants have been identified that result in catalytically inactive protein. About 3% of Caucasians are poor metabolizers of active agents metabolized by CYP2C19, while 13-23% of Asians are poor metabolizers of active agents metabolized by CYP2C19.

Previous in vivo data from Bruce et al. (Bruce R B et al. (1966) Metabolism of metaxalone. J Med Chem. 9, 286 288) showed that 27% of metaxalone was converted to a carboxylic acid derivative that appeared to be subsequently glucuronidated to an additional metabolite. Bruce et al did not identify the metabolic enzymes involved in this process. However, the FDA has suggested that identification of the particular cytochrome P450 isozymes involved is warranted when cytochrome P450 enzymes account for at least 25% of the total clearance of an active agent, as observed for metaxalone, since in vitro identification of the cytochrome P450 isozymes that metabolize a particular active agent helps predict the potential for in vivo active agent interactions, the impact of polymorphic enzyme activity on active agent disposition, and the formation of toxic or active metabolites.

Active agent interactions present a health risk to patients and a medical challenge for all medical care workers. Various studies of adverse reactions from exposure to active agents have found that 6.5-23% of the adverse reactions result from active agent interactions. Unfortunately, each year a number of deaths occur as the direct result of patients taking a new prescription pharmaceutical product in combination with their existing medication regimen. By understanding the unique functions and characteristics of Phase I and Phase II metabolic enzymes, such as the cytochrome p450 enzyme superfamily, medical care workers such as physicians and pharmacists may better anticipate, avoid, or safely manage active agent interactions and may predict or explain an individual's response to a particular therapeutic regimen.

There accordingly remains a need in the art for improved methods for the administration and use of metaxalone, in particular methods that take into account the effects of metaxalone on activity of Phase I and Phase II metabolic enzymes, including the cytochrome P450 isozymes.

SUMMARY

Disclosed herein are methods of using metaxalone. Metaxalone can be used in the treatment of various diseases or conditions, including, for example, musculoskeletal conditions and head pain.

In an embodiment, the method comprises administering metaxalone and a substance that is a known inhibitor or a known inducer of CYP1A2, CYP2C8, CYP2C9, CYP2C19, CYP2D6, CYP2E1, or CYP3A4 to a patient; and monitoring the patient during administration of metaxalone and the substance.

In an embodiment, the method comprises determining that a patient in need metaxalone therapy is taking a substance that is a known inhibitor of a cytochrome p450 isozyme, wherein the cytochrome P450 is CYP1A2, CYP2C8, CYP2C9, CYP2C19, CYP2D6, CYP2E1, or CYP3A4, and adjusting administration to the patient of metaxalone or the substance to avoid an adverse event associated with metaxalone.

In an embodiment, the method comprises administering metaxalone and an inhibitor of a cytochrome p450 isozyme, wherein the cytochrome P450 is CYP1A2, CYP2C8, CYP2C9, CYP2C19, CYP2D6, CYP2E1, or CYP3A4 to a patient; and altering dosing of the inhibitor or metaxalone for the patient if metaxalone plasma concentration of the patient increases during coadministration with the inhibitor.

In an embodiment, the method comprises administering metaxalone and an inducer of CYP3A4 to a patient; and altering dosing of the inducer of CYP3A4 or metaxalone for the patient if metaxalone plasma concentration of the patient decreases during coadministration with the inducer of CYP3A4.

In an embodiment, the method comprises administering metaxalone and an inhibitor of CYP1A2, CYP2C8, CYP2C9, CYP2C19, CYP2D6, CYP2E1, or CYP3A4 to a patient; determining that the patient experiences a metaxalone-associated toxicity during coadministration with the inhibitor; and altering dosing of the inhibitor or metaxalone such that the metaxalone-associated toxicity is reduced.

In an embodiment, the method comprises administering metaxalone and an inducer of CYP1A2, CYP2C8, CYP2C9, CYP2C19, CYP2D6, CYP2E1, or CYP3A4 to a patient; determining that the patient experiences a subtherapeutic outcome for metaxalone during coadministration with the inducer; and altering dosing of the inducer or metaxalone such that efficacy is achieved.

In an embodiment, the method comprises determining that a patient in need metaxalone therapy is taking a substance that is a known inducer of CYP1A2, CYP2C8, CYP2C9, CYP2C19, CYP2D6, CYP2E1, or CYP3A4, and adjusting administration to the patient of metaxalone or the substance to avoid a subtherapeutic outcome with metaxalone.

In an embodiment, the method comprises administering metaxalone to a patient in need of metaxalone therapy; determining that a known inhibitor of CYP1A2, CYP2C8, CYP2C9, CYP2C19, CYP2D6, CYP2E1, or CYP3A4 is administered to the patient; and monitoring the patient during administration of metaxalone and the known inhibitor for an adverse event associated with metaxalone.

In an embodiment, the method comprises administering metaxalone to a patient in need of metaxalone therapy; determining that a known inducer of CYP1A2, CYP2C8, CYP2C9, CYP2C19, CYP2D6, CYP2E1, or CYP3A4 is administered to the patient; and monitoring the patient during administration of metaxalone and the known inducer for reduced efficacy of metaxalone.

In an embodiment, the method comprises determining for a patient to whom metaxalone is going to be administered or is being administered whether a substance that is currently being or will be administered to the patient is an inhibitor of a cytochrome P450 isozyme (CYP) selected from CYP1A2, CYP2C8, CYP2C9, CYP2C19, CYP2D6, CYP2E1, and CYP3A4; and determining risk for the patient of a metaxalone-associated toxicity resulting from inhibition of metaxalone metabolism by the CYP during coadministration of metaxalone and the substance.

In an embodiment, the method comprises determining for a patient to whom metaxalone is going to be administered or is being administered whether a substance that is currently being or will be administered to the patient is an inducer of a cytochrome P450 isozyme (CYP) selected from CYP1A2, CYP2C8, CYP2C9, CYP2C19, CYP2D6, CYP2E1, and CYP3A4; and determining risk for the patient of a subtherapeutic outcome for metaxalone resulting from induction of metaxalone metabolism by the CYP during coadministration of metaxalone and the substance.

In an embodiment, the method comprises determining a dosing regimen for metaxalone to be administered to a patient in need thereof, determining that a substance that is a known inhibitor of a cytochrome P450 isozyme (CYP) selected from CYP1A2, CYP2C8, CYP2C9, CYP2C19, CYP2D6, CYP2E1, and CYP3A4 is currently administered or will be administered to the patient, and altering dosing of metaxalone administered to the patient from the determined dosing regimen while the known inhibitor of the CYP is coadministered to the patient to prevent sedation.

In an embodiment, the method comprises determining that a substance that is a known inducer or a known inhibitor of a cytochrome P450 isozyme (CYP) selected from CYP1A2, CYP2C8, CYP2C9, CYP2C19, CYP2D6, CYP2E1, and CYP3A4 is administered to a patient in need of a skeletal muscle relaxant; and optimizing a dose of metaxalone administered to the patient by administering a dose of metaxalone greater than a standard dose if a known inducer of the CYP is administered to the patient or administering a dose less than a standard dose of metaxalone if a known inhibitor of the CYP is administered to the patient.

In another embodiment, the method comprises informing a user that metaxalone is metabolized by a cytochrome p450 isozyme, wherein the cytochrome P450 is CYP1A2, CYP2C8, CYP2C9, CYP2C19, CYP2D6, CYP2E1, or CYP3A4.

In another embodiment, the method comprises informing a user that metaxalone inhibits a cytochrome p450 isozyme.

In yet another embodiment, the method comprises informing a user that metaxalone induces a cytochrome p450 isozyme.

In another embodiment, the method comprises informing a user that metaxalone is metabolized by a cytochrome P450 isozyme (CYP), wherein the CYP is CYP1A2, CYP2C8, CYP2C9, CYP2C19, CYP2D6, CYP2E1, or CYP3A4; and that there is a potential active agent interaction for metaxalone with an active agent that is a substrate, inhibitor, or inducer of the CYP or that taking metaxalone with the active agent can affect the plasma concentration, bioavailability, safety, efficacy, or a combination comprising at least one of the foregoing of metaxalone or the active agent.

In another embodiment, the method comprises informing a user that metaxalone is an inhibitor or an inducer of a cytochrome p450 isozyme and administration of metaxalone with a substance that is a substrate of the cytochrome p450 isozyme can affect the plasma concentration, bioavailability, safety, efficacy, or a combination comprising at least one of the foregoing of the substance.

In yet another embodiment, the method comprises obtaining metaxalone from a container providing information that metaxalone affects activity of a cytochrome p450 isozyme.

In yet another embodiment, the method comprises obtaining metaxalone from a container providing information that metaxalone is metabolized by a cytochrome p450 isozyme.

In yet another embodiment, the method comprises obtaining metaxalone from a container providing information that metaxalone is an inhibitor or an inducer of a cytochrome p450 isozyme.

In yet another embodiment, the method comprises administering to a patient metaxalone and an active agent; and informing the patient that metaxalone affects activity of a cytochrome p450 isozyme.

In yet another embodiment, the method comprises informing a user that metaxalone affects activity of a cytochrome p450 isozyme; that administration of metaxalone with a substance can affect the plasma concentration, bioavailability, safety, efficacy, or a combination comprising at least one of the foregoing of metaxalone or the substance; and that any effect on the plasma concentration, bioavailability, safety, efficacy, or a combination comprising at least one of the foregoing of metaxalone or the substance can vary with administration of metaxalone with or without food.

In another embodiment, the method comprises obtaining metaxalone from a container providing information that metaxalone affects activity of a cytochrome p450 isozyme; that administration of metaxalone with a substance can affect the plasma concentration, bioavailability, safety, efficacy, or a combination comprising at least one of the foregoing of metaxalone or the substance; and that any effect on the plasma concentration, bioavailability, safety, efficacy, or a combination comprising at least one of the foregoing of metaxalone or the substance can vary with administration of metaxalone with or without food.

Also disclosed herein are methods of manufacturing a metaxalone product.

In one embodiment, the method comprises packaging a metaxalone dosage form with information that metaxalone affects activity of a cytochrome p450 isozyme.

In another embodiment, the method comprises packaging a metaxalone dosage form with information that metaxalone is metabolized by a cytochrome p450 isozyme.

In another embodiment, the method comprises packaging a metaxalone dosage form with information that metaxalone is an inhibitor or an inducer of a cytochrome p450 isozyme.

In yet another embodiment, the method comprises packaging a metaxalone dosage form with information that metaxalone affects activity of a cytochrome p450 isozyme; that administration of metaxalone with a substance can affect the plasma concentration, safety, or efficacy of the metaxalone or the substance; and that any effect on the plasma concentration, bioavailability, safety, efficacy, or a combination comprising at least one of the foregoing of metaxalone or the substance can vary with administration of metaxalone with or without food.

Also disclosed herein are articles of manufacture comprising a container containing a dosage form of metaxalone.

In one embodiment, the container is associated with published material informing that metaxalone affects activity of a cytochrome p450 isozyme.

In another embodiment, the container is associated with published material informing that metaxalone is metabolized by a cytochrome p450 isozyme.

In another embodiment, the container is associated with published material informing that metaxalone is an inhibitor or an inducer of a cytochrome p450 isozyme.

In yet another embodiment, the container is associated with published material informing that metaxalone affects activity of a cytochrome p450 isozyme; that administration to a patient of metaxalone with a substance can affect plasma concentration, bioavailability, safety, efficacy, or a combination comprising at least one of the foregoing of metaxalone or the substance; and that any effect on the plasma concentration, bioavailability, safety, efficacy, or a combination comprising at least one of the foregoing of metaxalone or the substance can vary with administration of metaxalone with or without food.

In yet another embodiment, the article comprises a container comprising a dosage form of metaxalone, and published material. In one embodiment, the published material informs that there is a potential active agent interaction with warfarin; or that administration with warfarin can affect the plasma concentration, bioavailability, safety, efficacy, or a combination comprising at least one of the foregoing of metaxalone or warfarin. In another embodiment, the published material informs that metaxalone is a substrate of CYP1A2, CYP2C8, CYP2C9, CYP2C19, CYP2D6, CYP2E1, or CYP3A4, or that metaxalone is an inhibitor of CYP1A2, CYP2B6, CYP2C9, CYP2C19, CYP2D6, CYP2E1, or CYP3A4, or that metaxalone is an inducer of CYP1A2 or CYP3A4.

Also disclosed herein is an article of manufacture comprising packaging material and a product contained within the packaging material, wherein the product comprises, as at least one active ingredient, metaxalone, and wherein the packaging material comprises a label approved by a regulatory agency for the product which states that metaxalone affects activity of a cytochrome p450 isozyme.

Also disclosed herein is a method of using an active agent that is a known substrate, inhibitor, or inducer of a cytochrome P450 isozyme (CYP) selected from CYP1A2, CYP2C8, CYP2C9, CYP2C19, CYP2D6, CYP2E1, and CYP3A4 or a substrate of a cytochrome p450 isozyme.

In one embodiment, the method comprises informing a user that metaxalone affects activity of a cytochrome p450 isozyme and that administration of the active agent with metaxalone can affect the plasma concentration, bioavailability, safety, efficacy, or a combination comprising at least one of the foregoing of the active agent or metaxalone.

In another embodiment, the method comprises obtaining an active agent that is a known substrate, inhibitor, or inducer of a cytochrome P450 isozyme (CYP) selected from CYP1A2, CYP2C8, CYP2C9, CYP2C19, CYP2D6, CYP2E1, and CYP3A4 or a substrate of a cytochrome p450 isozyme from a container providing information that metaxalone affects activity of a cytochrome p450 isozyme and that administration of the active agent with metaxalone can affect plasma concentration, bioavailability, safety, efficacy, or a combination comprising at least one of the foregoing of the active agent or metaxalone.

Also disclosed herein is a method of manufacturing a pharmaceutical product comprising an active agent that is a known substrate, inhibitor, or inducer of a cytochrome P450 isozyme (CYP) selected from CYP1A2, CYP2C8, CYP2C9, CYP2C19, CYP2D6, CYP2E1, and CYP3A4 or a substrate of a cytochrome p450 isozyme.

In one embodiment, the method comprises packaging a dosage form of the active agent that is a known substrate, inhibitor, or inducer of a cytochrome P450 isozyme (CYP) selected from CYP1A2, CYP2C8, CYP2C9, CYP2C19, CYP2D6, CYP2E1, and CYP3A4 or a substrate of a cytochrome p450 isozyme with information that metaxalone affects activity of a cytochrome p450 isozyme and that administration of the active agent with metaxalone can affect plasma concentration, bioavailability, safety, efficacy, or a combination comprising at least one of the foregoing of the active agent or metaxalone.

Also disclosed herein is an article of manufacture comprising a container containing a dosage form of an active agent that is a known substrate, inhibitor, or inducer of a cytochrome P450 isozyme (CYP) selected from CYP1A2, CYP2C8, CYP2C9, CYP2C19, CYP2D6, CYP2E1, and CYP3A4 or a substrate of a cytochrome p450 isozyme. The container is associated with published material informing that metaxalone affects activity of a cytochrome p450 isozyme and that administration to a patient of the active agent and metaxalone can affect plasma concentration, bioavailability, safety, efficacy, or a combination comprising at least one of the foregoing of the active agent or metaxalone.

These and other embodiments, advantages and features of the present invention become clear when detailed description and examples are provided in subsequent sections.

DETAILED DESCRIPTION

Disclosed herein are methods of using metaxalone and metaxalone products. The inventors have determined that metaxalone is metabolized by several cytochrome P450 isozymes and identified risks associated with administration of metaxalone with a substance which is an inhibitor or an inducer of this isozyme. With the knowledge of the particular information, a medical care worker can better avoid or safely manage an active agent interaction in a patient between metaxalone and the substance, and its resultant effects on efficacy or safety of metaxalone. Specifically, knowledge that metaxalone is metabolized by the particular cytochrome P450 isozymes permits the administration of metaxalone and a substance which is an inhibitor or an inducer of this isozyme to a patient to be optimized for the patient by a medical care worker to provide safe use of metaxalone, while oftentimes reducing or minimizing side effects or adverse events resulting from interactions with the substance. Knowledge of the particular information permits a medical care worker to use metaxalone to treat a patient that is taking another substance which is an inhibitor or an inducer of the particular cytochrome P450 isozymes such that a side effect, an adverse reaction, or an active agent interaction between metaxalone and the substance can be avoided in the patient. Knowledge of the particular information allows proper dosing, dispensing, and administration of metaxalone or the substance to the patient by the patient's medical care worker to avoid, or reduce risk of occurrence of a sub-therapeutic effect, a side effect, an adverse reaction, or an active agent interaction between metaxalone and the substance and alerts the patient and the patient's medical care worker to the need to monitor the patient for symptoms of a sub-therapeutic effect, a side effect, an adverse reaction, or an active agent interaction between metaxalone and the substance.

Metaxalone therapy can be considered optimal when effective plasma levels are reached when required. In addition, peak plasma values ($C_{max}$) should be as low as possible so as to reduce the incidence and severity of possible side effects.

The terms "a" and "an" do not denote a limitation of quantity, but rather denote the presence of at least one of the referenced item. The term "or" means "and/or". The terms "comprising", "having", "including", and "containing" are to be construed as open-ended terms (i.e., meaning "including, but not limited to"). Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

An "active agent" means a compound (including metaxalone), element, or mixture that when administered to a patient, alone or in combination with another compound, element, or mixture, confers, directly or indirectly, a physiological effect on the patient. The indirect physiological effect may occur via a metabolite or other indirect mechanism. When the active agent is a compound, then salts, solvates (including hydrates) of the free compound or salt, crystalline forms, non-crystalline forms, and any polymorphs of the compound are included. Compounds may contain one or more asymmetric elements such as stereogenic centers, stereogenic axes and the like, e.g., asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, all optical isomers in pure form and mixtures thereof are encompassed. In addition, compounds with carbon-carbon double bonds may occur in Z- and E-forms, with all isomeric forms of the compounds. In these situations, the single enantiomers, i.e., optically active forms can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column All forms are contemplated herein regardless of the methods used to obtain them.

All forms (for example solvates, optical isomers, enantiomeric forms, polymorphs, free compound and salts of an active agent) of metaxalone or other active agent may be employed either alone or in combination.

"Active agent interaction" refers to a change in the metabolism of an active agent in a patient that can occur with co-administration of a second active agent. A "potential active agent interaction" refers to an active agent interaction between two active agents that is theoretically possible based on knowledge that one of the active agents is metabolized by a given cytochrome p450 isozyme and that the second of the active agents is a substrate, inhibitor, or inducer of that cytochrome p450 isozyme.

"Administering metaxalone with a substance", "administering metaxalone and a substance", or "co-administering metaxalone and a substance" means metaxalone and the substance are administered simultaneously in a single dosage form, administered concomitantly in separate dosage forms, or administered in separate dosage forms separated by some amount of time that is within the time in which both metaxalone and the substance are within the blood stream of a patient. The metaxalone and the substance need not be prescribed for a patient by the same medical care worker. The substance need not require a prescription. Administration of metaxalone or the substance can occur via any appropriate route, for example, oral tablets, oral capsules, oral liquids, inhalation, injection, suppositories or topical contact.

"Adverse event" means any untoward medical occurrence in a patient administered an active agent and which does not necessarily have to have a causal relationship with this treatment. An adverse event (AE) can therefore be any unfavorable and unintended sign (including an abnormal laboratory finding, for example), symptom, or disease temporally associated with the use of the active agent, whether or not considered related to the active agent.

"Adverse reaction" means a response to an active agent which is noxious and unintended and which occurs at doses normally used in humans for prophylaxis, diagnosis, or therapy of disease or for modification of physiological function. The unintended response can be an unexpected diminished or enhanced pharmacologic activity or toxicity of the active agent, e.g., a carisoprodol-associated toxicity. An adverse reaction also includes any undesirable or unexpected event requiring discontinuation of the active agent, modification of the dose, prolonged hospitalization, or the administration of supportive treatment.

"Affects" includes an increase or decrease in degree, level, or intensity; a change in time of onset or duration; a change in type, kind, or effect, or a combination comprising at least one of the foregoing.

As used herein, "allelic variant" means one of the alternative forms at a genetic locus on a single chromosome. For loci in most of the human genome, a human has two chromosomes, which may carry the same or two different allelic variants.

"Adjusting administration of an active agent", "altering administration of an active agent", "adjusting dosing of an active agent", or "altering dosing of an active agent" are all equivalent and mean making no change in the dose or dosing regimen of the active agent; tapering off, reducing, or increasing the dose or the dosing interval of the active agent; ceasing to administer the active agent to the patient; or substituting a different active agent for the active agent.

"Dosing regimen" means the dose of an active agent taken at a first time by a patient and the interval (time or symptomatic) at which any subsequent doses of the active agent are taken by the patient. The additional doses of the active agent can be different from the dose taken at the first time. For metaxalone, the standard dosing regimen for adults and children over 12 years of age is 800 mg, three or four times daily.

A "dose" means the measured quantity of an active agent to be taken at one time by a patient.

"Bioavailability" means the extent or rate at which an active agent is absorbed into a living system or is made available at the site of physiological activity. For active agents that are intended to be absorbed into the bloodstream, bioavailability data for a given formulation may provide an estimate of the relative fraction of the administered dose that is absorbed into the systemic circulation. "Bioavailability" can be characterized by one or more pharmacokinetic parameters.

A "dosage form" means a unit of administration of an active agent. Examples of dosage forms include tablets, capsules, injections, suspensions, liquids, emulsions, creams, ointments, suppositories, inhalable forms, transdermal forms, and the like.

The term "effective amount" or "therapeutically effective amount" means an amount effective, when administered to a patient, to provide any therapeutic benefit. A therapeutic benefit may be an amelioration of symptoms, e.g., an amount effective to decrease the symptoms of an acute musculoskeletal condition, such as muscle spasms. The amount that is "effective" will vary from subject to subject, depending on the age and general condition of the individual, the particular active agent, and the like. Thus, it is not always possible to specify an exact "effective amount." However, an appropriate "effective" amount in any individual case may be determined by one of ordinary skill in the art using routine experimentation. In certain circumstances a patient may not present symptoms of a condition for which the patient is being treated. A therapeutically effective amount of an active agent may also be an amount sufficient to provide a significant positive effect on any indicium of a disease, disorder, or condition, e.g. an amount sufficient to significantly reduce the frequency and severity of muscle spasms. A significant effect on an indicium of a disease, disorder, or condition is statistically significant in a standard parametric test of statistical significance, for example Student's T-test, where $p \leq 0.05$. An "effective amount" or "therapeutically effective amount" of metaxalone may also be an amount of about 3600 mg per day or less, about 3200 mg per day or less, about 50 mg to about 3600 mg per day, or of any dosage amount approved by a governmental authority such as the US FDA, for use in treatment. In some embodiments amounts of 3200 mg metaxalone per day, 800 mg metaxalone per unit dosage form, or 400 mg metaxalone or less per unit dosage form is an "effective amount" or "therapeutically effective amount" of metaxalone.

"Efficacy" means the ability of an active agent administered to a patient to produce a therapeutic effect in the patient.

As used herein "food" means a solid food with sufficient bulk and fat content that it is not rapidly dissolved and absorbed in the stomach. More specifically, the food is a meal, such as breakfast, lunch, or dinner. A dosage of metaxalone administered to a patient "with food" or in a "fed" state is administered to the patient between about 30 minutes prior to about 2 hours after eating a meal; more specifically, the dosage is administered within 15 minutes of eating a meal. The terms "without food" or "fasted" are defined to mean the condition of not having consumed solid food for about one hour prior to until about 2 hours after such consumption.

"Head pain" includes any painful conditions of the head, but particularly includes headaches, such as migraines, cluster headaches, tension headaches, or tension related migraines. Head pain further includes painful facial conditions such as TMJ (temporomandibular joint) disorders.

"Informing" means referring to or providing, published material, for example, providing an active agent with published material to a user; or presenting information orally, for example, by presentation at a seminar, conference, or other educational presentation, by conversation between a pharmaceutical sales representative and a medical care worker, or by conversation between a medical care worker and a patient; or demonstrating the intended information to a user for the purpose of comprehension.

"Labeling" means all labels or other means of written, printed, graphic, electronic, verbal, or demonstrative communication that is upon a pharmaceutical product or a dosage form or that accompanies such pharmaceutical product or dosage form.

As used herein, an enzyme "metabolizing" a substance means the enzyme can chemically transform the substance.

A "medical care worker" means a worker in the health care field who may need or utilize information regarding an active agent, including a dosage form thereof, including information on safety, efficacy, dosing, administration, or pharmacokinetics. Examples of medical workers include physicians, pharmacists, physician's assistants, nurses, aides, caretakers (which can include family members or guardians), emergency medical workers, and veterinarians.

As used herein, "metaxalone therapy" refers to medical treatment of a symptom, disorder, or condition by administration of metaxalone.

The term "musculoskeletal condition" includes any condition affecting the muscles, tendons, ligaments, bones, joints, and associated tissues that move the body and maintain its form. Such conditions include conditions that originate in the muscles, tendons, ligaments, or bones and associated tissues or conditions that originate elsewhere in the body, for example in the central or peripheral nervous system, that are manifested in the muscles, tendons, ligaments, bones, joints or associated tissues.

A substance having a "narrow therapeutic index" (NTI) means a substance falling within any definition of narrow therapeutic index as promulgated by the U.S. Food and Drug Administration or any successor agency thereof, for example, a substance having a less than 2-fold difference in median lethal dose (LD50) and median effective dose (ED50) values, or having a less than 2-fold difference in the minimum toxic concentration and minimum effective concentration in the blood; and for which safe and effective use of the substance requires careful titration and patient monitoring.

"Oral dosage form" includes a dosage form for oral administration.

A "patient" means a human or non-human animal in need of medical treatment. Medical treatment can include treatment of an existing condition, such as a disease or disorder, prophylactic or preventative treatment, or diagnostic treatment. In some embodiments the patient is a human patient.

A "pharmaceutical supplier" means a person (other than a medical care worker), business, charitable organization, governmental organization, or other entity involved in the transfer of active agent, including a dosage form thereof, between entities, for profit or not. Examples of pharmaceutical suppliers include pharmaceutical distributors, pharmaceutical wholesalers, pharmaceutical benefits managers, pharmacy chains, pharmacies (online or physical), hospitals, HMOs, supermarkets, the Veterans Administration, or foreign businesses or individuals importing active agent into the United States.

"Pharmacokinetic parameters" describe the in vivo characteristics of an active agent (or surrogate marker for the active agent) over time, such as plasma concentration (C), $C_{max}$, $C_n$, $C_{24}$, $T_{max}$, and AUC. "$C_{max}$" is the measured concentration of the active agent in the plasma at the point of maximum concentration. "$C_n$" is the measured concentration of an active agent in the plasma at about n hours after administration. "$C_{24}$" is the measured concentration of an active agent in the plasma at about 24 hours after administration. The term "$T_{max}$" refers to the time at which the measured concentration of an active agent in the plasma is the highest after administration of the active agent. "AUC" is the area under the curve of a graph of the measured concentration of an active agent (typically plasma concentration) vs. time, measured from one time point to another time point. For example $AUC_{0-t}$ is the area under the curve of plasma concentration versus time from time 0 to time t. The $AUC_{0-\infty}$ or $AUC_{0-INF}$ is the calculated area under the curve of plasma concentration versus time from time 0 to time infinity.

"Phenotype" means an observable trait of an organism resulting from the interplay of environment and genetics. Examples include apparent rate of metabolism of substrates by a cytochrome p450 isozyme of an organism, such as the "poor metabolizer" (PM) or "ultrarapid metabolizer" (UM) phenotypes identified in humans for metabolism of substrates metabolized by CYP2D6.

"Polymorphism" means the differences in DNA sequences that occur naturally in a population. Single nucleotide substitutions, insertions, and deletions of nucleotides and repetitive sequences (microsatellites) are all examples of a polymorphism.

A "product" or "pharmaceutical product" means a dosage form of an active agent plus published material, and optionally packaging.

"Providing" means giving, administering, selling, distributing, transferring (for profit or not), manufacturing, compounding, or dispensing.

"Published material" means a medium providing information, including printed, audio, visual, or electronic medium, for example a flyer, an advertisement, a product insert, printed labeling, an internet web site, an internet web page, an internet pop-up window, a radio or television broadcast, a compact disk, a DVD, an audio recording, or other recording or electronic medium.

"Product insert" means the professional labeling (prescribing information) for a pharmaceutical product, a patient package insert for the pharmaceutical product, or a medication guide for the pharmaceutical product.

"Professional labeling" or "prescribing information" means the official description of a pharmaceutical product approved by a regulatory agency (e.g., FDA or EMEA) regulating marketing of the pharmaceutical product, which includes a summary of the essential scientific information needed for the safe and effective use of the drug, such as, for example indication and usage; dosage and administration; who should take it; adverse events (side effects); instructions for use in special populations (pregnant women, children, geriatric, etc.); safety information for the patient, and the like.

"Patient package insert" means information for patients on how to safely use a pharmaceutical product that is part of the FDA-approved labeling. It is an extension of the professional labeling for a pharmaceutical product that may be distributed to a patient when the product is dispensed which provides consumer-oriented information about the product in lay language, for example it may describe benefits, risks, how to recognize risks, dosage, or administration.

"Medication Guide" means an FDA-approved patient labeling for a pharmaceutical product conforming to the specifications set forth in 21 CFR 208 and other applicable regulations which contains information for patients on how to safely use a pharmaceutical product. A medication guide is scientifically accurate and is based on, and does not conflict with, the approved professional labeling for the pharmaceutical product under 21 CFR 201.57, but the language need not be identical to the sections of approved labeling to which it corresponds. A medication guide is typically available for a pharmaceutical product with special risk management information.

"Risk" means the probability or chance of adverse reaction, injury, or other undesirable outcome arising from a medical treatment. An "acceptable risk" of an adverse reaction means that individuals or groups in society are willing to take or be subjected to the risk that the adverse reaction might occur since the adverse reaction is one whose probability of occurrence is small, or whose consequences are so slight, or the benefits (perceived or real) of the active agent are so great. An "unacceptable risk" of an adverse reaction means that individuals or groups in society are unwilling to take or be subjected to the risk that the adverse reaction might occur upon weighing the probability of occurrence of the adverse reaction, the consequences of the adverse reaction, and the benefits (perceived or real) of the active agent. "At risk" means in a state or condition marked by a high level of risk or susceptibility.

Herein, an "acceptable risk" means a measure of the risk of harm, injury, or disease arising from a medical treatment that will be tolerated by a person or group. Whether a risk is "acceptable" will depend upon the advantages that the person or group perceives to be obtainable in return for taking the risk, whether they accept whatever scientific and other advice is offered about the magnitude of the risk, and numerous other factors, both political and social.

Risk assessment consists of identifying and characterizing the nature, frequency, and severity of the risks associated with the use of a product.

"Safety" means the incidence or severity of adverse events associated with administration of an active agent, including adverse effects associated with patient-related factors (e.g., age, gender, ethnicity, race, target illness, abnormalities of renal or hepatic function, co-morbid illnesses, genetic characteristics such as metabolic status, or environment) and active agent-related factors (e.g., dose, plasma level, duration of exposure, or concomitant medication).

"Salts" as used herein describes "pharmaceutically acceptable salts" of metaxalone and other active agents discussed herein and also includes solvates and hydrates of such active agents. The active agent may be modified by making non-toxic acid or base addition salts thereof Examples of pharmaceutically acceptable salts include mineral or organic acid addition salts of basic residues such as amines; alkali or organic addition salts of acidic residues; and the like, and combinations comprising one or more of the foregoing salts. The pharmaceutically acceptable salts include non-toxic salts and the quaternary ammonium salts of the metaxalone. For example, non-toxic acid salts include those derived from inorganic acids such as hydrochloric, hydrobromic, sulfuric, sulfamic, phosphoric, nitric and the like; other acceptable inorganic salts include metal salts such as sodium salt, potassium salt, cesium salt, and the like; and alkaline earth metal salts, such as calcium salt, magnesium salt, and the like, and combinations comprising one or more of the foregoing salts. Pharmaceutically acceptable organic salts includes salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—(CH2)n-COOH where n is 0-4, and the like; organic amine salts such as triethylamine salt, pyridine salt, picoline salt, ethanolamine salt, triethanolamine salt, dicyclohexylamine salt, N,N'-dibenzylethylenediamine salt, and the like; and amino acid salts such as arginate, aspartinate, glutamate, and the like; and combinations comprising one or more of the foregoing salts.

A "sensitive plasma concentration profile active agent" means an active agent for which a moderate change in plasma concentration can have a deleterious effect on the prescribed therapeutic intent.

"Side effect" means a secondary effect resulting from taking an active agent. The secondary effect can be a negative (unfavorable) effect or a positive (favorable) effect.

Solid dosage forms of metaxalone comprise up to about 3600 mg metaxalone, specifically about 50 to about 3200 mg metaxalone, more specifically about 100 to about 800 mg metaxalone. In one embodiment, the solid dosage form is an oral dosage form, for example, a tablet. In some embodiments, the tablets comprise about 400 mg, about 450 mg, or about 800 mg metaxalone. Amounts in dosage forms are given for metaxalone free base, however equivalent amounts of other forms of metaxalone can be used.

A "substance" taken or administered with metaxalone means a substance that affects the safety, bioavailability, plasma concentration, efficacy, or a combination comprising at least one of the foregoing of metaxalone or the substance. A "substance" can be an active agent, an herbal supplement, a nutritional supplement, a vitamin, a xenobiotic, or an environmental contaminant.

A substance is a "substrate" of enzyme activity when it can be chemically transformed by action of the enzyme on the substance. "Enzyme activity" refers broadly to the specific activity of the enzyme (i.e., the rate at which the enzyme transforms a substrate per mg or mole of enzyme) as well as the metabolic effect of such transformations. Thus, a substance is an "inhibitor" of enzyme activity when the specific activity or the metabolic effect of the specific activity of the enzyme can be decreased by the presence of the substance, without reference to the precise mechanism of such decrease. For example a substance can be an inhibitor of enzyme activity by competitive, non-competitive, allosteric or other type of enzyme inhibition, by decreasing expression of the enzyme, or other direct or indirect mechanisms. Similarly, a substance is an "inducer" of enzyme activity when the specific activity or the metabolic effect of the specific activity of the enzyme can be increased by the presence of the substance, without reference to the precise mechanism of such increase. For example a substance can be an inducer of enzyme activity by increasing reaction rate, by increasing expression of the enzyme, by allosteric activation or other direct or indirect mechanisms. It is possible for a substance to be a substrate, inhibitor, or inducer of an enzyme activity. For example, the substance can be an inhibitor of enzyme activity by one mechanism and an inducer of enzyme activity by another mechanism. The function (substrate, inhibitor, or inducer) of the substance with respect to activity of an enzyme can depend on environmental conditions.

"Subtherapeutic outcome" means a response to an active agent that is less than that anticipated from a dosing regimen of the active agent used for treatment of disease or for modification of physiological function.

The terms "treating" and "treatment" mean implementation of therapy with the intention of reducing in severity or frequency symptoms, elimination of symptoms or underlying cause, prevention of the occurrence of symptoms or their underlying cause, and improvement or remediation of damage.

A "user" means a patient, a medical care worker, or a pharmaceutical supplier.

The cytochrome p450 enzymes are a highly diverse superfamily of enzymes. Each cytochrome p450 enzyme is termed an "isoform" or "isozyme" since each derives from a different gene. Cytochrome p450 enzymes are categorized into families and subfamilies by amino acid sequence similarities. These enzymes are designated by the letters "CYP" followed by an Arabic numeral representing the family, a letter representing the sub-family and another Arabic numeral representing a specific gene (e.g., CYP2D6). Particular isozymes discussed herein are named as per the recommendations of the P450 Gene Superfamily Nomenclature Committee (see e.g., "P450 superfamily: Update on new sequences, gene mapping, accession numbers, and nomenclature" Pharmacogenetics 6, 1-42 1996, part A pp. 1-21.). Herein, the designation for a cytochrome p450 isozyme may encompass the homolog from any species identified as having such an isozyme. For example, CYP1A2 genes are known in at least rat, human, rabbit, hamster, dog, guinea pig, mouse and chicken and the designation "CYP1A2" includes the CYP1A2 protein from each species known to have a CYP1A2 gene. In some embodiments, the designation for a cytochrome p450 isozyme is the human isozyme.

In one embodiment, CYP1A2 is human CYP1A2 (Entrez Gene ID: 1544; reference protein sequence Genbank NP_000752), and includes any allelic variants. Specifically, CYP1A2 includes any allelic variants included in the list of human CYP1A2 allelic variants maintained by the Human Cytochrome P450 (CYP) Allele Nomenclature Committee; more specifically it includes any of the *1 through *16 alleles. Additional reference amino acid sequences for human CYP1A2 include Genbank AAK25728, AAY26399, AAA35738, AAA52163, AAA52163, AAF13599, AAH67424, AAH67425, AAH67426, AAH67427, AAH67428, AAH67429, AAA52154, AAA52146, CAA77335, P05177, Q6NWU3, Q6NWU5, Q9BXX7, and Q9UK49.

In one embodiment, CYP2A6 is human CYP2A6 (Entrez Gene ID: 1548; reference protein sequence Genbank NP_000753), and includes any CYP2A6 allelic variants. Specifically, CYP2A6 includes any allelic variants included in the list of human CYP2A6 allelic variants maintained by the Human Cytochrome P450 (CYP) Allele Nomenclature Committee; more specifically it includes any of the *1 through *22 alleles. Additional reference amino acid sequences for human CYP2A6 include Genbank AAG45229, AAB40518, AAF13600, AAH96253, AAH96254, AAH96255, AAH96256, AAA52067, CAA32097, CAA32117, P11509, Q13120, and Q4VAU0.

In one embodiment, CYP2B6 is human CYP2B6 (Entrez Gene ID: 1555; reference protein sequence Genbank NP_000758), and includes any CYP2B6 allelic variants. Specifically, CYP2B6 includes any allelic variants included in the list of human CYP2B6 allelic variants maintained by the Human Cytochrome P450 (CYP) Allele Nomenclature Committee; more specifically it includes any of the *1 through *25 alleles. Additional reference amino acid sequences for human CYP2B6 include Genbank AAF32444, AAD25924, ABB84469, AAF13602, AAH67430, AAH67431, AAA52144, P20813, Q6NWU1, Q6NWU2, and Q9UNX8.

In one embodiment, CYP2C8 is human CYP2C8 (Entrez Gene ID: 1558; reference protein sequence Genbank NP_110518), and includes any CYP2C8 allelic variants. Specifically, CYP2B8 includes any allelic variants included in the list of human CYP2C8 allelic variants maintained by the Human Cytochrome P450 (CYP) Allele Nomenclature Committee; more specifically it includes any of the *1 through *10 alleles. Additional reference amino acid sequences for human CYP2C8 include Genbank CAH71307, AAR89907, CAA38578, AAH20596, AAA35739, AAA35740, AAA52160, AAA52161, CAA35915, CAA68550, P10632, Q5VX93, Q8WWB1, and Q9UCZ9.

In one embodiment, CYP2C9 is human CYP2C9 (Entrez Gene ID: 1559; reference protein sequence Genbank NP_000762), and includes any CYP2C9 allelic variants. Specifically, CYP2CP includes any allelic variants included in the list of human CYP2C9 allelic variants maintained by the Human Cytochrome P450 (CYP) Allele Nomenclature Committee; more specifically it includes any of the *1 through *24 alleles. Additional reference amino acid sequences for human CYP2C9 include Genbank CAH71303, AAP88931, AAT94065, AAW83816, AAD13466, AAD13467, AAH20754, AAH70317, BAA00123, AAA52159, AAB23864, P11712, Q5EDC5, Q5VX92, Q6IRV8, Q8WW80, Q9UEH3, and Q9UQ59.

In one embodiment, CYP2C19 is human CYP2C19 (Entrez Gene ID: 1557; reference protein sequence Genbank NP_000760), and includes any CYP2C19 allelic variants. Specifically, CYP2C19 includes any allelic variants included in the list of human CYP2C19 allelic variants maintained by the Human Cytochrome P450 (CYP) Allele Nomenclature Committee; more specifically it includes any of the *1 through *21 alleles. Additional reference amino acid sequences for human CYP2C19 include Genbank BAD02827, CAH73444, CAH74068, AAV41877, AAL31347, AAL31348, AAA36660, AAB59426, CAA46778, P33261, Q16743, Q767A3, Q8WZB1, and Q8WZB2.

In one embodiment, CYP2D6 is human CYP2D6 (Entrez Gene ID: 1565; reference protein sequence Genbank NP_000097), and includes any CYP2D6 allelic variants. Specifically, it CYP2D6 includes any allelic variants included in the list of human CYP2D6 allelic variants maintained by the Human Cytochrome P450 (CYP) Allele Nomenclature Committee; more specifically it includes any of the *1 through *58 alleles. Additional reference amino acid sequences for human CYP2D6 include Genbank AAS55001, ABB01370, ABB01371, ABB01372, ABB01373, AAA35737, AAA53500, BAD92729, AAU87043, AAH66877, AAH67432, AAH75023, AAH75024, AAI06758, AAI06759, CAG30316, AAA52153, AAA36403, CAA30807, and P10635.

In one embodiment, CYP2E1 is human CYP2E1 (Entrez Gene ID: 1571; reference protein sequence Genbank NP_000764), and includes any CYP2E1 allelic variants. Specifically, CYP2E1 includes any allelic variants included in the list of human CYP2E1 allelic variants maintained by the Human Cytochrome P450 (CYP) Allele Nomenclature Committee; more specifically it includes any of the *1 through *7 alleles. Additional reference amino acid sequences for human CYP2E1 include Genbank CAH70047, BAA00902, BAA08796, AAA52155, AAD13753, AAF13601, CAI47002, AAH67433, AAH67435, AAZ77710, AAA35743, AAD14267, P05181, Q16868, Q5VZD5, Q6LER5, Q6NWT7, and Q6NWT9.

In one embodiment, CYP3A4 is human CYP3A4 (Entrez Gene ID: 1576; reference protein sequence Genbank NP_059488), and includes any CYP3A4 allelic variants. Specifically, CYP3A4 includes any allelic variants included in the list of human CYP3A4 allelic variants maintained by the Human Cytochrome P450 (CYP) Allele Nomenclature Committee; more specifically it includes any of the *1 through *20 alleles. Additional reference amino acid sequences for human CYP3A4 include Genbank AAF21034, AAG32290, AAG53948, EAL23866, AAF13598, CAD91343, CAD91645, CAD91345, AAH69418, AAI01632, BAA00001, AAA35747, AAA35742, AAA35744, AAA35745, CAA30944, P05184, P08684, Q6GRK0, Q7Z448, Q86SK2, Q86SK3, and Q9BZM0.

The ability of metaxalone to act as a substrate, inhibitor, or inducer of various cytochrome p450 isozymes was determined in studies described below. A summary of the findings of the studies is provided in Table 1.

TABLE 1

Summary of metaxalone effects on cytochrome p450 isozymes.

| CYP isozyme | Substrate | Inhibitor | Inducer/Inhibitor |
| --- | --- | --- | --- |
| 1A2 | + | + | + |
| 2A6 | 0 | 0 | 0 |
| 2B6 | 0 | + | 0 |
| 2C8 | + | 0 | ND |
| 2C9 | + | 0 | − |
| 2C19 | + | + | 0 |
| 2D6 | + | + | − |
| 2E1 | + | + | 0 |
| 3A4 | + | + | + |

For each possible function of metaxalone (i.e., substrate, inhibitor, or inducer), there is a column in the table. A "+" in a particular column and row indicates that the study found that metaxalone functioned in that capacity with respect to the cytochrome p450 isozyme represented in that row, while a "0" indicates that the results did not support that metaxalone functioned in that capacity with respect to the cytochrome p450 isozyme represented in that row. In the column labeled Inducer/Inhibitor, a "+" denotes that the metaxalone functioned as an inducer of the CYP isozyme, while a "−" denotes that metaxalone functioned as an inhibitor of the CYP isozyme. For example, metaxalone was found to be a substrate, inhibitor, and inducer of CYP1A2 activity, and was found to be an inhibitor of CYP2C9 activity. The symbol "ND" indicates that no experiment was performed.

As summarized in Table 1, metaxalone was found to be a substrate for CYP1A2, CYP2C8, CYP2C9, CYP2C19, CYP2D6, CYP2E1, and CYP3A4, and therefore can also act as a competitor of other substrates for these isozymes. Additionally, metaxalone was determined to be an inhibitor of the cytochrome p450 isozymes CYP1A2, CYP2B6, CYP2C9, CYP2C19, CYP2D6, CYP2E1, and CYP3A4 and an inducer of CYP1A2 and CYP3A4.

Enzymes involved in Phase I and Phase II active agent metabolism, such as the cytochrome p450 isozymes, respond to the constantly changing types and amounts of substrate active agents they encounter. For example, changes in active agent metabolism due to competition for the same cytochrome p450 isoform can change the clinical effectiveness or safety of an active agent by altering the plasma concentration of the active agent or its metabolite(s). Similarly, inhibition or induction of the cytochrome p450 isoform that metabolizes a particular active agent can change the clinical effectiveness or safety of that active agent. Therefore, for any cytochrome p450 for which metaxalone acts as a substrate, inhibitor, or inducer, the administration of metaxalone with a substance that is a substrate, inhibitor, or inducer of that cytochrome p450 can affect the metabolism of the metaxalone or the substance. For the case in which the substance is a narrow therapeutic index active agent, such as warfarin or phenytoin, too little of the active agent in the blood stream can lead to insufficient therapeutic activity, while a too large dose of the active agent can lead to excessive therapeutic activity or toxicity, both of which can be detrimental.

The invention provides methods of using metaxalone. These methods include using metaxalone in the treatment of various diseases or conditions, including, for example, musculoskeletal conditions, specifically acute and painful musculoskeletal conditions, muscle sprains, muscle spasms, spasticity, low back pain and stiffness, acute lumbosacral pain, cervical stiffness or torticohis; as well as head pain, including migraines, cluster headaches, tension headaches, or tension related migraines. Using metaxalone in the treatment or prevention of a disease or condition in a patient can include administering metaxalone to a patient, dispensing metaxalone to a patient, or dispensing metaxalone to a medical care worker for administering to a patient.

In one embodiment, the method comprises informing a user that metaxalone affects activity of a cytochrome p450 isozyme. The cytochrome p450 isozyme may be any cytochrome p450 isozyme. For example the cytochrome p450 isozyme may be CYP1A2 CYP2B6, CYP2C9, CYP2C19, CYP2D6, CYP2E1, or CYP3A4. In some embodiments the cytochrome p450 isozyme is CYP1A2, CYP3A4, or CYP2C19. In certain embodiments the cytochrome p450 isozyme is a human enzyme. In some embodiments, the method further comprises providing the user with metaxalone. If the user is a patient, the method can further comprise dosing the patient to improve safety or efficacy of metaxalone such that the dosing minimizes adverse events or side effects of metaxalone, specifically when metaxalone is co-administered to the patient with another substance, such as another active agent.

Informing the user that metaxalone affects the activity of a cytochrome p450 isozyme includes providing a user with information about any effect of metaxalone on the activity of any cytochrome p450 isozyme. Informing the user that metaxalone affects the activity of a cytochrome p450 isozyme includes informing a user of any of the following: that metaxalone is metabolized by a cytochrome p450 isozyme; that metaxalone is an inducer of activity of a cytochrome p450 isozyme; that a cytochrome p450 isozyme metabolizing metaxalone is CYP1A2, CYP2C8, CYP2C9, CYP2C19, CYP2D6, CYP2E1, or CYP3A4; that metaxalone is metabolized by CYP1A2, CYP2E1, or CYP3A4; that metaxalone is a competitive inhibitor of CYP1A2, CYP2C9, CYP2C19, CYP2D6, CYP2E1, or CYP3A4; that metaxalone is a substrate of CYP1A2, CYP2C8, CYP2C9, CYP2C19, CYP2D6, CYP2E1, and CYP3A4; that there is a potential active agent interaction between metaxalone and an active agent that is a substrate, inhibitor, or inducer of CYP1A2, CYP2C8, CYP2C9, CYP2C19, CYP2D6, CYP2E1, and CYP3A4; that metaxalone is an inhibitor of a cytochrome p450 isozyme; that caution is recommended when metaxalone and a substrate of CYP2B6, CYP2C9, CYP2C19, or CYP2D6 are administered to a patient known to have a poor metabolizer phenotype for or that has reduced activity of CYP2B6, CYP2C9, CYP2C19, or CYP2D6; that caution is recommended when administering metaxalone with the substance when the substance is an active agent having a narrow therapeutic index; that the allelic variants of CYP2B6, CYP2C9, CYP2C19, or CYP2D6 present in the patient can further affect the potential active agent interaction between metaxalone and an active agent; that there is a potential active agent interaction of metaxalone with an active agent that is a substrate of the cytochrome p450 isozyme; that there is a potential active agent interaction of metaxalone with warfarin; that metaxalone affects the activity of CYP1A2, CYP2B6, CYP2C9, CYP2C19, CYP2D6, CYP2E1, or CYP3A4; that there is a potential active agent interaction of metaxalone with a substance that is a substrate of CYP1A2, CYP2B6, CYP2C9, CYP2C19, CYP2D6, CYP2E1, or CYP3A4; that metaxalone is an inhibitor of CYP1A2, CYP2B6, CYP2C9, CYP2C19, CYP2D6, CYP2E1, or CYP3A4; and that metaxalone is an inducer of CYP1A2 or CYP3A4 activity; that there is a potential active agent interaction of metaxalone with a substance that is a substrate of CYP1A2 or CYP3A4.

The method can further comprise informing the user that administration of metaxalone with a substance can affect the plasma concentration, bioavailability, safety, efficacy, or a combination comprising at least one of the foregoing of metaxalone or the substance. In some embodiments, the method further comprises providing the user with the substance.

The effect of coadministration of metaxalone and the substance can be determined by comparison of the plasma concentration, bioavailability, safety, efficacy, or a combination comprising at least one of the foregoing of the substance with and without coadministration of metaxalone or by comparison of the plasma concentration, bioavailability, safety, efficacy, or a combination comprising at least one of the foregoing of metaxalone with and without coadministration of the substance.

Informing the user that administration of metaxalone with a substance can affect the plasma concentration, bioavailability, safety, efficacy, or a combination comprising at least one of the foregoing of metaxalone or the substance includes providing a user with information about any effect of metaxalone on plasma concentration, bioavailability, safety, efficacy, or a combination comprising at least one of the foregoing of metaxalone or the substance. This includes informing a user of any of the following: that taking metaxalone with an active agent can affect the bioavailability, safety, or efficacy of the active agent or metaxalone; that administration of metaxalone and a substance that is a substrate, inhibitor, or inducer of CYP1A2, CYP2C8, CYP2C9, CYP2C19, CYP2D6, CYP2E1, or CYP3A4 can affect plasma concentration, bioavailability, safety, efficacy, or a combination comprising at least one of the foregoing of metaxalone or the substance; that administration of metaxalone with a substance that is a CYP1A2, CYP2C9, CYP2C19, CYP2D6, CYP2E1, and CYP3A4 substrate can increase the plasma concentration of the substance; that taking metaxalone with an active agent that is a substrate, inhibitor, or inducer of CYP1A2, CYP2C8, CYP2C9, CYP2C19, CYP2D6, CYP2E1, or CYP3A4 can affect the plasma concentration, bioavailability, safety, efficacy, or a combination comprising at least one of the foregoing of metaxalone or the active agent; that administration of metaxalone with an active agent that is a cytochrome p450 isozyme substrate having a narrow therapeutic index can affect plasma concentration, bioavailability, safety, efficacy, or a combination comprising at least one of the foregoing of the active agent; that administration of metaxalone with an active agent that is a CYP1A2, CYP2C8, CYP2C9, CYP2C19, CYP2D6, CYP2E1, or CYP3A4 substrate having a narrow therapeutic index can affect plasma concentration, bioavailability, safety, efficacy, or a combination comprising at least one of the foregoing of the active agent; that metaxalone can affect the plasma concentration, bioavailability, safety, efficacy, or a combination comprising at least one of the foregoing of an active agent that is a substrate of the cytochrome p450 isozyme; that administration of metaxalone with an active agent that is a substrate of the cytochrome p450 isozyme and that has a narrow therapeutic index can increase plasma concentration of the active agent; that a substance that induces CYP1A2, CYP2C8, CYP2C9, CYP2C19, CYP2D6, CYP2E1, or CYP3A4 activity can decrease metaxalone plasma concentration; that co-administration of metaxalone and a substance that inhibits CYP1A2, CYP2C8, CYP2C9, CYP2C19, CYP2D6, CYP2E1, or CYP3A4 may result in an increase in metaxalone plasma concentration, whereas co-administration of metaxalone and a substance that induces CYP1A2, CYP2C8, CYP2C9, CYP2C19, CYP2D6, CYP2E1, or CYP3A4 may decrease metaxalone plasma concentration; that a substance that inhibits CYP1A2, CYP2C8, CYP2C9, CYP2C19, CYP2D6, CYP2E1, or CYP3A4 activity can increase metaxalone plasma concentration; that a substance that is a substrate of CYP1A2, CYP2C8, CYP2C9, CYP2C19, CYP2D6, CYP2E1, or CYP3A4 can increase plasma concentration of metaxalone or the substance; that administration of metaxalone with warfarin can affect the plasma concentration, bioavailability, safety, efficacy, or a combination comprising at least one of the foregoing of metaxalone or warfarin; that administration of metaxalone with an active agent that is a known substrate, inhibitor, or inducer of YP1A2, CYP2C8, CYP2C9, CYP2C19, CYP2D6, CYP2E1, or CYP3A4 or that is a substrate of CYP2B6, CYP2C9, CYP2D6, CYP2E1, or CYP3A4 can affect plasma concentration, bioavailability, safety, efficacy, or a combination comprising at least one of the foregoing of the active agent or metaxalone; that the plasma concentration of a substance that is a substrate of CYP1A2, CYP2B6, CYP2C9, CYP2C19, CYP2D6, CYP2E1, or CYP3A4 can decrease when the substance is administered with metaxalone; that administration of metaxalone with a substance that is a substrate of CYP1A2, CYP2B6, CYP2C9, CYP2C19, CYP2D6, CYP2E1, or CYP3A4 can affect plasma concentration, bioavailability, safety, efficacy, or a combination comprising at least one of the foregoing of the substance; that administration of metaxalone with an active agent that is a CYP1A2, CYP2B6, CYP2C9, CYP2C19, CYP2D6, CYP2E1, or CYP3A4 substrate having a narrow therapeutic index can affect plasma concentration, bioavailability, safety, efficacy, or a combination comprising at least one of the foregoing of the active agent; that the plasma concentration of a substance that is a substrate of CYP1A2 or CYP3A4 can decrease when the substance is administered with metaxalone; that administration of metaxalone and a substance that is a substrate of CYP1A2 or CYP3A4 activity can affect plasma concentration, bioavailability, safety, efficacy, or a combination comprising at least one of the foregoing of the substance.

In another embodiment, the method comprises informing a user that metaxalone is metabolized by a cytochrome p450 isozyme. The cytochrome p450 isozyme metabolizing metaxalone is CYP1A2, CYP2C8, CYP2C9, CYP2C19, CYP2D6, CYP2E1, or CYP3A4; specifically the cytochrome p450 isozyme metabolizing metaxalone is CYP1A2, CYP2E1, or CYP3A4. In some embodiments, the method further comprises informing the user that administration of metaxalone and a substance that is a substrate, inhibitor, or inducer of CYP1A2, CYP2C8, CYP2C9, CYP2C19, CYP2D6, CYP2E1, or CYP3A4 can affect plasma concentration, bioavailability, safety, efficacy, or a combination comprising at least one of the foregoing of metaxalone or the substance. Methods provided herein include informing a user that the substance or metaxalone is a substrate, inhibitor, or inducer of CYP1A2, CYP2C8, CYP2C9, CYP2C19, CYP2D6, CYP2E1, or CYP3A4. The substance can inhibit CYP1A2, CYP2C8, CYP2C9, CYP2C19, CYP2D6, CYP2E1, or CYP3A4 activity and the effect can be an increase in metaxalone plasma concentration, or the substance can induce CYP1A2, CYP2C8, CYP2C9, CYP2C19, CYP2D6, CYP2E1, or CYP3A4 activity and the effect can be a decrease in metaxalone plasma concentration. In yet another embodiment, the user is informed that the substance is a substrate of CYP1A2, CYP2C8, CYP2C9, CYP2C19, CYP2D6, CYP2E1, or CYP3A4 and plasma concentration of the substance or metaxalone can increase. In yet another embodiment, the method comprises informing the user that taking metaxalone and a substance that is a substrate of CYP1A2, CYP2C8, CYP2C9, CYP2C19, CYP2D6, CYP2E1, or CYP3A4 can increase plasma concentration of metaxalone or the substance.

The method also comprises informing a user that metaxalone is an inhibitor or an inducer of a cytochrome p450 isozyme. Cytochrome p450 isozymes inhibited by metaxalone include CYP1A2, CYP2B6, CYP2C9, CYP2C19, CYP2D6, CYP2E1, and CYP3A4. Cytochrome p450 isozymes that are induced by metaxalone include CYP1A2 and CYP3A4. In some embodiments the method further comprises informing a user that administration of metaxalone and a substance that is a substrate of the cytochrome p450 isozyme can affect plasma concentration, bioavailability, safety, efficacy, or a combination comprising at least one of the foregoing of the substance. In some embodiments, the method can further comprise informing that metaxalone is an inhibitor of the cytochrome p450 isozyme or that the effect on the substance can be an increase in plasma concentration. In other embodiments, the method can further comprise informing that metaxalone is an inducer of CYP1A2 or CYP3A4 or that the effect on the substance can be a decrease in plasma concentration.

In some embodiments, the method can further comprise providing the user with metaxalone. Other embodiments include administering metaxalone or another substance. Administration may be to a patient by the patient, a medical worker, or other user. Metaxalone can be administered in a therapeutically effective amount. In some embodiments, the method can further comprise providing the user with metaxalone or informing the user that caution is recommended when administering metaxalone with the substance when the substance is an active agent having a narrow therapeutic index.

In an embodiment, the method includes informing a user that there is a potential active agent interaction between metaxalone and a substance that is a substrate, an inhibitor, or an inducer of CYP1A2, CYP2C8, CYP2C9, CYP2C19, CYP2D6, CYP2E1, or CYP3A4; administering metaxalone to a patient, wherein the patient is receiving a substance that is a substrate, an inhibitor, or an inducer of CYP1A2, CYP2C8, CYP2C9, CYP2C19, CYP2D6, CYP2E1, and CYP3A4; and monitoring the patient. Monitoring the patient can be monitoring the patient's blood plasma level of metaxalone or the substance; monitoring the patient for a symptom of an active agent interaction between the substance and metaxalone; monitoring the patient for an adverse reaction or side effect resulting from coadministration of the substance and metaxalone; monitoring the patient for an adverse reaction or side effect associated with metaxalone; monitoring the patient for a subtherapeutic outcome associated with a reduced plasma concentration of metaxalone, or monitoring the patient for an adverse reaction or side effect associated with an elevated or reduced plasma concentration of metaxalone. The method can further include adjusting administration of metaxalone or the substance in response to the monitoring. The substance can be an active agent.

In some embodiments, the method of using metaxalone can further comprise administering metaxalone or a substance. Administration may be to a patient by the patient, a medical care worker, or other user. Metaxalone can be administered in a therapeutically effective amount. The substance can be an active agent. The active agent can have a sensitive plasma concentration profile or a narrow therapeutic index. The method can also comprise monitoring a patient, for example, monitoring the patient for an adverse reaction, a side effect, a subtherapeutic outcome, or a symptom of an active agent interaction or monitoring a patient's plasma concentration of metaxalone or the substance. The method can also comprise adjusting administration or dosing of the substance or metaxalone for the patient based on the results of monitoring, for example a determined plasma concentration of the active agent or metaxalone.

In all of the embodiments herein, a medical care worker can determine the plasma concentration of a substance such as an active agent, including metaxalone, by performing or ordering the performance of any suitable method. For example, the medical care worker could order a test using blood drawn from the patient for determining the plasma concentration of metaxalone or the substance.

The information provided to a user can comprise any combination of information disclosed herein concerning the effects of metaxalone on the activity of a cytochrome p450 isozyme or on the plasma concentration, bioavailability, safety, efficacy, or a combination comprising at least one of the foregoing of metaxalone or a substance. The information may also comprise any combination of information disclosed herein concerning the effects of a substance on the activity of a cytochrome p450 isozyme or on the plasma concentration, bioavailability, safety, efficacy, or a combination comprising at least one of the foregoing of metaxalone or a substance when the substance is used with metaxalone.

Medical information provided in any of the methods described herein concerning the effects of administering metaxalone with an additional substance may alternatively be provided in layman's terms, so as to be better understood by patients or non-medical professionals. Those of skill in the medical art are familiar with the various layman's terms that can be used to describe the effects of active agent interactions.

In yet another embodiment, the method of using metaxalone comprises obtaining metaxalone from a container providing information that metaxalone affects activity of a cytochrome p450. Information can also be provided that administering metaxalone with a substance can affect plasma concentration, bioavailability, safety, efficacy, or a combination comprising at least one of the foregoing of the substance or metaxalone. The method also comprises providing metaxalone in the container providing such information. The method may also comprise providing a substance, such as an active agent, in a container providing information that metaxalone affects activity of a cytochrome p450 or that administering metaxalone with the substance may affect plasma concentration, bioavailability, safety, efficacy, or a combination comprising at least one of the foregoing of the substance or metaxalone. The provided information may be any information disclosed herein concerning the effects of metaxalone or a substance on the activity of a cytochrome p450 isozyme or any information disclosed herein concerning the effects of metaxalone when administered with a substance on the plasma concentration, bioavailability, safety, efficacy, or a combination comprising at least one of the foregoing of the substance or metaxalone. The method can further comprise ingesting the metaxalone or the substance.

The method may also comprise informing the user or providing information that, when an active agent and metaxalone are administered to a patient, that it is recommended that a medical care worker determine the patient's plasma concentration of the active agent; and alter dosing of the active agent for the patient based on the determined active agent plasma concentration. Additionally, the method can comprise determining the metabolizer phenotype of the patient or the allelic variant of the patient for a cytochrome p450 isozyme; specifically the cytochrome p450 isozyme is CYP2B6, CYP2C9, CYP2C19, or CYP2D6.

Also disclosed herein are methods of administering metaxalone.

In an embodiment, the method comprises determining for a patient to whom metaxalone is going to be administered or is being administered whether a substance that is currently being or will be administered to the patient is an inhibitor of a cytochrome P450 isozyme (CYP), wherein the CYP is CYP1A2, CYP2C8, CYP2C9, CYP2C19, CYP2D6, CYP2E1, and CYP3A4; and determining risk for the patient of a metaxalone-associated toxicity resulting from inhibition of metaxalone metabolism by the CYP during coadministration of metaxalone and the substance.

In an embodiment, the method comprises determining for a patient to whom metaxalone is going to be administered or is being administered whether a substance that is currently being or will be administered to the patient is an inducer of a cytochrome P450 isozyme (CYP), wherein the CYP is CYP1A2, CYP2C8, CYP2C9, CYP2C19, CYP2D6, CYP2E1, and CYP3A4; and determining risk for the patient of a subtherapeutic outcome for metaxalone resulting from induction of metaxalone metabolism by the CYP during coadministration of metaxalone and the substance.

Depending on the determined risk of a metaxalone-related toxicity or a subtherapeutic outcome, the methods can further comprise administering metaxalone or the substance to the patient. For example, if there is no risk of metaxalone-associated toxicity or of a subtherapeutic outcome for the metaxalone treatment, or if the risk is determined to be acceptable, metaxalone and the substance can be administered to the patient. Alternatively, if there is a risk of metaxalone-associated toxicity or of a subtherapeutic outcome for the metaxalone treatment, or if the risk is determined to be unacceptable, metaxalone can be administered to the patient, but not the substance.

The method can further comprise determining that the patient has a poor metabolizer phenotype for CYP2C9, CYP2C19, or CYP2D6; or that the patient belongs to an Asiatic or Oceanic ethnic group.

Determining risk of an adverse reaction, such as a toxicity or a subtherapeutic outcome, for metaxalone and a substance with which it may be administered is based on an appropriate set of risk parameters. As will be evident to those of skill in the art, the risk parameters to be considered will be based upon factors which influence the risk that a known or suspected adverse reaction will occur if the patient receives metaxalone with or without the substance, and will vary depending upon the substance in question for coadministration with metaxalone. Factors that may define the relevant risk parameters include effect of the substance on activity of the relevant cytochrome P450 isozyme(s), e.g. CY3A4 or CYP2C19; the likelihood that certain preexisting conditions may exist in the patient; information collected from the patient including information relating to the patient's conduct; the patient's past or ongoing medical treatment, such as other procedures or medication which the patient may have received or is still receiving; results of certain diagnostic tests which have been performed; and the like. Information collected from the patient for determining risk may be obtained prior to the initial dispensation of metaxalone or the substance to the patient or may be obtained from the patient on a periodic basis. For example, after treatment with metaxalone and the substance is begun, information on the onset of certain symptoms which may be indicative of the need for changes in the patient's treatment regimen may be obtained from the patient on a periodic basis.

Diagnostic tests may be probative of the concentration of one or more active agents, including a prescribed active agent, to assure that appropriate dosing is maintained in the patient. Such diagnostic testing may be conducted on any bodily fluid or waste product of the patient, including the blood, serum, plasma, saliva, semen or urine, as well as the feces. Diagnostic testing may also be performed on a biopsy of any tissue of the patient or may include genetic testing, which may be indicative of a genetic predisposition to a particular adverse side effect. Other forms of diagnostic testing, such as diagnostic imaging, or tests which may be probative of the proper functioning of any tissue, organ, or system are also contemplated. Preferably, appropriate information or diagnostic test results are obtained and considered in determining risk.

Where the relevant risk parameters indicate that the risk of the adverse reaction occurring outweighs the potential benefit of metaxalone or the substance, the risk can be deemed unacceptable.

Determining risk can comprise accessing a computer-hosted database. The database may be in the form of a look-up table, or similar structure, that provides output information based on the input of information.

Alternatively, determining risk can comprise obtaining information from standard treatment guidelines, textbooks, compendial literature, journals, drug manufacturer guidelines, internet websites providing information on active agent interactions (e.g., "Drug Interaction Checker" at the MEDScape website or the drug interaction website maintained by Dr. D. Flockhart, Indiana University School of Medicine); or FDA labeling for particular active agents.

In an embodiment, the method comprises informing a patient receiving an active agent or the patient's medical care worker that metaxalone is a substrate of CYP1A2, CYP2C8, CYP2C9, CYP2C19, CYP2D6, CYP2E1, or CYP3A4; and adjusting administration of metaxalone or the active agent to the patient as a result of the informing to avoid an adverse event associated with metaxalone, to avoid a subtherapeutic outcome for metaxalone in the patient, or to produce a treatment response in the patient. The active agent is a known substrate, inhibitor, or inducer of CYP1A2, CYP2C8, CYP2C9, CYP2C19, CYP2D6, CYP2E1, or CYP3A4.

In an embodiment, the method comprises administering metaxalone to a patient; and monitoring the patient during administration of metaxalone if the patient is taking a substance that is a known substrate, inhibitor, or inducer of activity of CYP1A2, CYP2C8, CYP2C9, CYP2C19, CYP2D6, CYP2E1, or CYP3A4.

In an embodiment, the method comprises determining that a substance that is a known substrate, inhibitor, or inducer of activity of CYP1A2, CYP2C8, CYP2C9, CYP2C19, CYP2D6, CYP2E1, or CYP3A4 is administered to the patient; and adjusting administration of metaxalone or the substance to the patient to avoid a metaxalone-related adverse reaction or subtherapeutic outcome.

In an embodiment, the method comprises determining that metaxalone is a substrate of a cytochrome P450, wherein the CYP is CYP1A2, CYP2C8, CYP2C9, CYP2C19, CYP2D6, CYP2E1, or CYP3A4; administering metaxalone to a patient; and monitoring the patient during administration of metaxalone if a substance that is a known substrate, inhibitor, or inducer of activity of the CYP is coadministered to the patient. The method can further comprise determining that a substance that is a known substrate, inhibitor, or inducer of activity of the CYP is administered to the patient.

Such methods can include informing a user that metaxalone is a substrate of the CYP. The method can include informing the user that administration of metaxalone with a substance can affect the plasma concentration, bioavailability, safety, efficacy, or a combination comprising at least one of the foregoing of metaxalone or the substance. The method can include informing the user of any information disclosed herein about metaxalone metabolism and any information disclosed herein about the effect of metaxalone or the substance on the plasma concentration, bioavailability, safety, efficacy, or a combination comprising at least one of the foregoing of metaxalone or the substance when metaxalone is used with the substance.

Determining that a substance that is a known substrate, inhibitor, or inducer of CYP1A2, CYP2C8, CYP2C9, CYP2C19, CYP2D6, CYP2E1, or CYP3A4 is administered to a patient in need of metaxalone therapy can be performed by consulting with the patient regarding substances, e.g., medications, taken in by the patient, a medical care worker administering medications to the patient, a prescription database including medications prescribed to the patient, or by any other method known in the art.

Determining that metaxalone is a substrate of a cytochrome p450 isozyme or determining that co-administration of metaxalone and a substance that inhibits that cytochrome P450 may result in an increased metaxalone plasma concentration, or that co-administration of metaxalone and a substance that induces that cytochrome P450 may result in a decreased metaxalone plasma concentration can be performed by consulting the package insert for the metaxalone product administered to the patient or consulting a database including prescribing information and potential risks for metaxalone, or by any other method known in the art.

Monitoring the patient can comprise monitoring the patient's plasma concentration of metaxalone or the substance; monitoring the patient for symptoms of an active agent interaction between the substance and metaxalone; monitoring the patient for an adverse reaction (e.g., a toxicity or a subtherapeutic outcome) resulting from administration of the substance and metaxalone; monitoring the patient for an adverse reaction (e.g., a toxicity or a subtherapeutic outcome) associated with metaxalone; or monitoring the patient for decreased efficacy of metaxalone.

Monitoring the patient can be monitoring any appropriate patient-specific, disease-specific, or substance-specific parameter appropriate to avoid or safely manage an active agent interaction. Monitoring the patient can be, for example, monitoring the patient for an adverse reaction, a subtherapeutic outcome, a side effect, or a symptom of an active agent interaction for example by physical examination or visual identification; monitoring the blood level of metaxalone or the substance in the patient; monitoring clinical laboratory tests appropriate for metaxalone, the substance, or a medical diagnosis for the patient; monitoring therapeutic effect of metaxalone or the substance on the patient's condition; monitoring occurrence in the patient of a known side effect or adverse reaction of metaxalone or the substance; monitoring the patient for occurrence of an unexpected response during treatment; monitoring changes in control, signs, or symptoms of a condition of the patient, or determining a complete list of medical diagnoses for the patient. Monitoring the patient can be performed by the patient or by a medical care worker.

For metaxalone, the most frequently reported adverse reactions include CNS reactions: drowsiness, dizziness, headache, and nervousness or "irritability"; and digestive reactions: nausea, vomiting, and gastrointestinal upset. Other possible adverse reactions include immune system reactions such as hypersensitivity reaction and rash with or without pruritus; hematologic reactions such as leukopenia and hemolytic anemia; and hepatobiliary reactions such as jaundice. Though rare, anaphylactoid reactions have been reported with metaxalone. Examples of metaxalone-associated toxicities include drowsiness, dizziness, impairment of a mental activity, impairment of a physical activity, central nervous system depression, respiratory depression, or coma.

Determining that a patient experiences an adverse reaction, such as a metaxalone-associated toxicity or a subtherapeutic outcome, can be performed by obtaining information from the patient regarding onset of certain symptoms which may be indicative of the adverse reaction, results of diagnostic tests indicative of the adverse reaction, and the like.

Determining the level of metabolism of metaxalone in a subject may be performed for example by determining plasma concentrations of metaxalone or appropriate metaxalone metabolites, and any other methods known in the art.

Adjusting administration of metaxalone or the substance to the patient to avoid an adverse reaction or a subtherapeutic outcome, or adjusting dosing regimens can be performed by one of ordinary skill in the art, taking into consideration the physiology of the patient, including such factors as the age, sex, and health of the patient, as well as active agents the patient may be taking at the time. Optionally, the patient can be monitored at the initial, or a subsequent, stage of treatment to ensure therapeutic plasma levels of metaxalone or the substance are achieved or maintained.

Various laboratory methods are known, including ones that are commercially available, for detecting the presence of allelic variants of cytochrome p450 isozymes in an individual or determining the metabolizer phenotype of an individual for a particular cytochrome p450 isozyme. Any suitable method known in the art may be used. Methods include analyzing a blood sample from the individual to determine the allelic variant of a particular cytochrome p450 isozyme gene present in the individual (for example by genotyping or haplotyping DNA or RNA from the gene using mass spectrometry, gel electrophoresis, or TAQMAN assays; or analyzing the protein sequence expressed by the gene). The metabolizer phenotype of the individual can be inferred based on the known properties of the allelic variants determined to be present in the individual. Alternatively, the blood sample can be used to measure enzyme activity of the cytochrome p450 isozyme using a suitable assay and isozyme-selective substrate. Among suitable isozyme-selective substrates are those used in the studies herein, or those suggested in FDA guidelines directed to collecting cytochrome p450 isozyme data for regulatory submissions relating to an active agent.

Food may alter the release of an active agent from a dosage form, the solubilization of the active agent, and the transport of the active agent across the intestinal wall. According to U.S. Pat. No. 6,407,128, pharmacokinetic studies of metaxalone indicate that food increases the rate and extent of absorption of a 400 mg oral dosage form in humans. In that study, food increased peak plasma concentrations ($C_{max}$), and extent of absorption ($AUC_{0-t}$, $AUC_{0-inf}$) relative to a fasted treatment with observed increases of 177.5%, 123.5%, and 115.4%. Based on that study, administration of metaxalone with food increases the bioavailability of metaxalone and therefore a particular oral dose given with food may physiologically correspond to a higher plasma concentration of metaxalone than the same oral dose given in a fasted state. Consequently, any effect on plasma concentration, bioavailability, safety, efficacy, or a combination comprising at least one of the foregoing of administration of metaxalone with an additional substance which is a substrate, inhibitor, or inducer of a cytochrome p450 isozyme for which metaxalone is a substrate, inhibitor, or inducer can be further affected by whether or not the metaxalone was administered with food.

Methods of using metaxalone comprise informing a user that metaxalone affects the activity of a cytochrome p450; that administration of metaxalone with a substance can affect the plasma concentration, bioavailability, safety, efficacy, or a combination comprising at least one of the foregoing of metaxalone or the substance; and that any effect on the plasma concentration, bioavailability, safety, efficacy, or a combination comprising at least one of the foregoing of metaxalone or the substance can vary with administration of metaxalone with or without food.

In another embodiment, the method of using metaxalone comprises obtaining metaxalone from a container providing information that metaxalone affects activity of a cytochrome p450; that administration of metaxalone with a substance can affect the plasma concentration, bioavailability, safety, or efficacy of metaxalone or the substance; and that any effect on the plasma concentration, bioavailability, safety, or efficacy of metaxalone or the substance can vary with administration of metaxalone with or without food. The method also includes providing metaxalone in the container providing information.

In one embodiment, the metaxalone is always administered with food. In another embodiment, the metaxalone is always administered without food. In yet another embodiment, the metaxalone is sometimes administered with food and sometimes administered without food.

Also disclosed herein are methods of manufacturing a metaxalone pharmaceutical product.

In one embodiment, the method comprises packaging a metaxalone dosage form with information that metaxalone affects activity of a cytochrome p450 isozyme. The information may also advise that administration of metaxalone with a substance can affect the plasma concentration, bioavailability, safety, efficacy, or a combination comprising at least one of the foregoing of metaxalone or the substance. The information may also include any information disclosed herein about the effect of metaxalone or a substance on the activity of a cytochrome p450 isozyme and any information disclosed herein about the effect of metaxalone or a substance on the plasma concentration, bioavailability, safety, efficacy, or a combination comprising at least one of the foregoing of metaxalone or the substance.

In an embodiment, the method comprises packaging a metaxalone dosage form with information that metaxalone is metabolized by a cytochrome p450 isozyme. The cytochrome p450 isozyme metabolizing metaxalone is CYP1A2, CYP2C8, CYP2C9, CYP2C19, CYP2D6, CYP2E1, or CYP3A4. The information may also advise that administration of metaxalone and a substance that is a substrate, inhibitor, or inducer of CYP1A2, CYP2C8, CYP2C9, CYP2C19, CYP2D6, CYP2E1, or CYP3A4 can affect plasma concentration, bioavailability, safety, efficacy, or a combination comprising at least one of the foregoing of metaxalone or the substance.

In an embodiment, the method comprises packaging a metaxalone dosage form with information that administration of metaxalone with an active agent that is a CYP1A2, CYP2C8, CYP2C9, CYP2C19, CYP2D6, CYP2E1, or CYP3A4 substrate having a narrow therapeutic index can affect plasma concentration, bioavailability, safety, efficacy, or a combination comprising at least one of the foregoing of the active agent.

In another embodiment, the method comprises packaging a metaxalone dosage form with information that metaxalone is an inhibitor or an inducer of a cytochrome p450 isozyme. The information may further advise that administration of metaxalone with an active agent that is a substrate of the cytochrome p450 isozyme can affect the plasma concentration, bioavailability, safety, efficacy, or a combination comprising at least one of the foregoing of the active agent. The cytochrome p450 isozyme is CYP1A2, CYP2B6, CYP2C9, CYP2C19, CYP2D6, CYP2E1, or CYP3A4. In some embodiments, the active agent is a substrate of the cytochrome p450 isozyme inhibited by metaxalone and the plasma concentration of the active agent can increase; in other embodiments, the active agent is a substrate of the cytochrome p450 isozyme induced by metaxalone and the plasma concentration of the active agent can decrease.

In yet another embodiment, the method comprises packaging a metaxalone dosage form with information that metaxalone affects activity of a cytochrome p450 isozyme and that administration of metaxalone with a substance can affect the plasma concentration, bioavailability, safety, efficacy, or a combination comprising at least one of the foregoing of the metaxalone or the substance; and that any effect on the plasma concentration, bioavailability, safety, efficacy, or a combination comprising at least one of the foregoing of metaxalone or the substance can vary with administration of metaxalone with or without food. In one embodiment, the metaxalone is always administered with food. In another embodiment, the metaxalone is always administered without food. In yet another embodiment, the metaxalone is sometimes administered with food and sometimes administered without food.

Another aspect of the invention is a method of using an active agent that is a known substrate, inhibitor, or inducer of CYP1A2, CYP2C8, CYP2C9, CYP2C19, CYP2D6, CYP2E1, or CYP3A4 or that is a substrate of a cytochrome p450 isozyme.

In one embodiment, the method comprises informing a user that metaxalone affects activity of a cytochrome p450 isozyme and that administration of the active agent and metaxalone can affect the plasma concentration, bioavailability, safety, efficacy, or a combination comprising at least one of the foregoing of the active agent or the metaxalone. The cytochrome p450 isozyme is CYP1A2, CYP2B6, CYP2C8, CYP2C9, CYP2C19, CYP2D6, CYP2E1, or CYP3A4. In some embodiments, the method further comprises providing the user with the active agent or metaxalone.

In another embodiment, the method comprises obtaining an active agent that is a known substrate, inhibitor, or inducer of CYP1A2, CYP2C8, CYP2C9, CYP2C19, CYP2D6, CYP2E1, or CYP3A49 or that is a substrate of a cytochrome p450 isozyme from a container providing information that metaxalone affects activity of a cytochrome p450 isozyme and that the administration of the active agent with metaxalone can affect plasma concentration, bioavailability, safety, efficacy, or a combination comprising at least one of the foregoing of the active agent or the metaxalone. The method may also comprise providing the active agent in the container providing information.

Also disclosed herein is a method of manufacturing a pharmaceutical product of an active agent that is a known substrate, inhibitor, or inducer of CYP1A2, CYP2C8, CYP2C9, CYP2C19, CYP2D6, CYP2E1, or CYP3A4 or that is a substrate of a cytochrome p450 isozyme.

In one embodiment, the method comprises packaging a dosage form of an active agent that is a known substrate, inhibitor, or inducer of CYP1A2, CYP2C8, CYP2C9, CYP2C19, CYP2D6, CYP2E1, or CYP3A4 or that is a substrate of a cytochrome p450 isozyme with information that metaxalone affects activity of a cytochrome p450 isozyme.

In each of the methods for using an active agent that is a known substrate, inhibitor, or inducer of CYP1A2, CYP2C8, CYP2C9, CYP2C19, CYP2D6, CYP2E1, or CYP3A4 or that is a substrate of a cytochrome p450 isozyme or the methods of manufacturing a pharmaceutical product of such an active agent, the information provided to the user or with the dosage form may include any information disclosed herein about the effect of metaxalone or the active agent on the activity of a cytochrome p450 isozyme and any information disclosed herein about the effect of metaxalone or the active agent on the plasma concentration, bioavailability, safety, efficacy, or a combination comprising at least one of the foregoing of metaxalone or the active agent.

The invention provides articles of manufacture.

In some embodiments, the article of manufacture comprises a container containing a dosage form of metaxalone.

Metaxalone can be formulated as a dosage form for administration where the formulation generally contains metaxalone and a pharmaceutically acceptable excipient. As used herein, "pharmaceutically acceptable excipient" means any other component added to the pharmaceutical formulation other than the active agent. Excipients may be added to facilitate manufacture, enhance stability, control release, enhance product characteristics, enhance bioavailability, enhance patient acceptability, etc. Pharmaceutical excipients include carriers, fillers, binders, disintegrants, lubricants, glidants, compression aids, colors, sweeteners, preservatives, suspending agents, dispersing agents, film formers, flavors, printing inks, buffer agents, pH adjusters, preservatives etc.

In one embodiment, the container is associated with published material informing that metaxalone affects activity of a cytochrome p450 isozyme. The published material can further inform that administration of metaxalone with a substance that is a substrate, inhibitor, or inducer of the cytochrome p450 isozyme can affect plasma concentration, bioavailability, safety, efficacy, or a combination comprising at least one of the foregoing of metaxalone or the substance. The published material may be in the form of printed labeling, or in some other form. The cytochrome p450 can be CYP1A2, CYP2B6, CYP2C8, CYP2C9, CYP2C19, CYP2D6, CYP2E1, or CYP3A4. The published material comprising the article of manufacture may also include any information disclosed herein about the effect of metaxalone or a substance on the activity of a cytochrome p450 isozyme and any information disclosed herein about the effect of metaxalone or a substance on the plasma concentration, bioavailability, safety, efficacy, or a combination comprising at least one of the foregoing of metaxalone or the substance.

In another embodiment, the container is associated with published material informing that metaxalone is metabolized by a cytochrome p450 isozyme. The cytochrome p450 isozyme metabolizing metaxalone is CYP1A2, CYP2C8, CYP2C9, CYP2C19, CYP2D6, CYP2E1, or CYP3A4. In some embodiments, the published material further informs that administration of metaxalone with a substance that is a substrate, inhibitor, or inducer of CYP1A2, CYP2C8, CYP2C9, CYP2C19, CYP2D6, CYP2E1, or CYP3A4 can affect plasma concentration, bioavailability, safety, efficacy, or a combination comprising at least one of the foregoing of metaxalone or the substance. In other embodiments, the published material further informs that a substance that induces CYP1A2, CYP2C8, CYP2C9, CYP2C19, CYP2D6, CYP2E1, or CYP3A49 activity can decrease metaxalone plasma concentration, that a substance that inhibits CYP1A2, CYP2C8, CYP2C9, CYP2C19, CYP2D6, CYP2E1, or CYP3A4 activity can increase metaxalone plasma concentration, or that a substance that is a substrate of CYP1A2, CYP2C8, CYP2C9, CYP2C19, CYP2D6, CYP2E1, or CYP3A4 can increase plasma concentration of metaxalone or the substance.

In yet another embodiment, the container is associated with published material informing that metaxalone is an inhibitor or an inducer of a cytochrome p450 isozyme. The published material may further inform that administration of metaxalone can affect the plasma concentration, bioavailability, safety, efficacy, or a combination comprising at least one of the foregoing of substances that are substrates of the cytochrome p450 isozyme. The cytochrome p450 isozyme is CYP1A2, CYP2B6, CYP2C9, CYP2C19, CYP2D6, CYP2E1, or CYP3A4.

In another embodiment, the container is associated with published material that includes information that caution is recommended when administering metaxalone with the substrate, wherein the substrate has a narrow therapeutic index.

In yet another embodiment, the container is associated with published material informing that metaxalone affects activity of a cytochrome p450 isozyme; that administration to a patient of metaxalone with a substance can affect plasma concentration, bioavailability, safety, efficacy, or a combination comprising at least one of the foregoing of metaxalone or the substance; and that any effect on the plasma concentration, bioavailability, safety, efficacy, or a combination comprising at least one of the foregoing of metaxalone or the substance can vary with administration of metaxalone with or without food.

In yet another embodiment, the article comprises a container comprising a dosage form of metaxalone, and published material. In one embodiment, the published material provides information that there is a potential active agent interaction with warfarin; or that administration with warfarin can affect the bioavailability, safety, or efficacy of metaxalone or warfarin. In another embodiment, the published material informs that metaxalone affects activity of CYP1A2, CYP2B6, CYP2C9, CYP2C19, CYP2D6, CYP2E1, or CYP3A4. The published material may further inform that there is a potential active agent interaction with a substance that is a substrate of CYP1A2, CYP2B6, CYP2C9, CYP2C19, CYP2D6, CYP2E1, or CYP3A4 or that administration of metaxalone with a substance that is a substrate of CYP1A2, CYP2B6, CYP2C9, CYP2C19, CYP2D6, CYP2E1, or CYP3A4 can affect plasma concentration, bioavailability, safety, efficacy, or a combination comprising at least one of the foregoing of the substance. In another embodiment, the published material informs that metaxalone is a substrate of CYP1A2, CYP2C8, CYP2C9, CYP2C19, CYP2D6, CYP2E1, or CYP3A4. The published material may also inform that there is a potential active agent interaction with a substance that is a substrate, inhibitor, or inducer of CYP1A2, CYP2C8, CYP2C9, CYP2C19, CYP2D6, CYP2E1, or CYP3A4 or that administration of metaxalone with a substance that is a substrate, inhibitor, or inducer of CYP1A2, CYP2C8, CYP2C9, CYP2C19, CYP2D6, CYP2E1, or CYP3A4 can affect plasma concentration, bioavailability, safety, efficacy, or a combination comprising at least one of the foregoing of metaxalone or the substance. In yet another embodiment, the published material informs that metaxalone is an inhibitor of activity of CYP1A2, CYP2B6, CYP2C9, CYP2C19, CYP2D6, CYP2E1, or CYP3A4. In yet another embodiment, the published material informs that metaxalone is an inducer of activity of CYP1A2 or CYP3A4. In each of these latter embodiments, the published material may further inform that there is a potential active agent interaction with a substance that is a substrate of CYP1A2, CYP2B6, CYP2C9, CYP2C19, CYP2D6, CYP2E1, or CYP3A4 or that administration of metaxalone with a substance that is a substrate of CYP1A2, CYP2B6, CYP2C9, CYP2C19, CYP2D6, CYP2E1, or CYP3A4 can affect plasma concentration, bioavailability, safety, efficacy, or a combination comprising at least one of the foregoing of the substance. In some embodiments, the published material can be printed labeling.

Also disclosed herein is an article of manufacture comprising packaging material and a dosage form contained within the packaging material, wherein the dosage form comprises, as at least one active ingredient, metaxalone, and wherein the packaging material comprises a label approved by a regulatory agency for the product. The label may inform that metaxalone affects activity of a cytochrome p450 isozyme; that a cytochrome p450 isozyme metabolizing metaxalone is CYP1A2, CYP2C8, CYP2C9, CYP2C19, CYP2D6, CYP2E1, or CYP3A4; that metaxalone is an inhibitor of activity of CYP1A2, CYP2B6, CYP2C9, CYP2C19, CYP2D6, CYP2E1, or CYP3A4; or that metaxalone is an inducer of activity of CYP1A2 or CYP3A4. Examples of regulatory agencies are the US FDA or the European Agency for the Evaluation of Medicinal Products (EMEA).

The invention further includes an article of manufacture comprising a container holding a dosage form of metaxalone associated with published material informing that there is a potential active agent interaction with warfarin, or that administration with warfarin can affect the bioavailability, safety, or efficacy of the metaxalone or the warfarin. The published material may further comprise instructions regarding measuring the Prothrombin Time/International Normalized Ratio daily, every other day, weekly, every other week, monthly, or according to another schedule or time criteria, or instructions to monitor the blood levels of warfarin as $AUC_{0-t}$, $AUC_{0-INF}$, $C_{MAX}$, or a combination comprising one or more of the foregoing pharmacokinetic parameters.

The invention includes articles of manufacture in which the substance administered with metaxalone is phenytoin. In one embodiment, the article of manufacture comprises a container holding a dosage form of metaxalone associated with published material informing that there is a potential active agent interaction with phenytoin, or that administration of metaxalone with phenytoin can affect the bioavailability, safety, efficacy or a combination comprising at least one of the foregoing of the metaxalone or the phenytoin. The published material may further comprise instructions to monitor the blood levels of phenytoin as $AUC_{0-t}$, $AUC_{0-INF}$, $C_{MAX}$, or a combination comprising one or more of the foregoing pharmacokinetic parameters.

Also disclosed herein is an article of manufacture comprising a container containing a dosage form of an active agent that is a known substrate, inhibitor, or inducer of CYP1A2, CYP2C8, CYP2C9, CYP2C19, CYP2D6, CYP2E1, or CYP3A or that is a substrate of a cytochrome p450 isozyme. The container is associated with published material informing that metaxalone affects activity of a cytochrome p450 isozyme and administration to a patient of the active agent and metaxalone can affect plasma concentration, bioavailability, safety, efficacy, or a combination comprising at least one of the foregoing of the active agent or metaxalone. In one embodiment of any of these methods or articles involving an active agent that is a known substrate, inhibitor or inducer of CYP1A2, CYP2C8, CYP2C9, CYP2C19, CYP2D6, CYP2E1, or CYP3A or that is a substrate of a cytochrome p450 isozyme, the active agent is an inducer of CYP1A2, CYP2C8, CYP2C9, CYP2C19, CYP2D6, CYP2E1, or CYP3A and plasma concentration of metaxalone can decrease. In another embodiment the active agent is an inhibitor of CYP1A2, CYP2C8, CYP2C9, CYP2C19, CYP2D6, CYP2E1, or CYP3A and plasma concentration of metaxalone can increase. In yet another embodiment, the active agent is a substrate of CYP1A2, CYP2C8, CYP2C9, CYP2C19, CYP2D6, CYP2E1, or CYP3A and plasma concentration of the active agent or metaxalone can increase. In yet another embodiment, the active agent is a substrate of CYP1A2, CYP2B6, CYP2C9, CYP2C19, CYP2D6, CYP2E1, or CYP3A4 and plasma concentration of the active agent can increase. In yet another embodiment, the active agent is a substrate of CYP1A2 or CYP3A4 and plasma concentration of the active agent can decrease. In any of these embodiments, the active agent can have a narrow therapeutic index. The published material comprising the article of manufacture may also include any information disclosed herein about the effect of metaxalone or the active agent on the activity of a cytochrome p450 isozyme and any information disclosed herein about the effect of metaxalone or the active agent on the plasma concentration, bioavailability, safety, efficacy, or a combination comprising at least one of the foregoing of metaxalone or the active agent.

In embodiments of the articles of manufacture, the dosage form will typically be contained in a suitable container capable of holding and dispensing the dosage form and which will not significantly interact with the active agent(s) in the dosage form. Further, the container will be in physical relation with the published material. The published material may be associated with the container by any means that maintains physical proximity of the two. By way of example, the container and the published material can both be contained in a packaging material such as a box or plastic shrink wrap. Alternatively, the published material can be bonded to the container, such as with glue that does not obscure the published material, or with other bonding or holding means. Yet another alternative is that the published material is placed within the container with the dosage form.

In other embodiments of the article, someone hands the published material to the patient, for example a pharmacist can hand a product insert to a patient in conjunction with dispensing the dosage form. The published material may be a product insert, flyer, brochure, or a packaging material for the dosage form such as a bag, or the like.

In any of the embodiments disclosed herein the published material or information associated with or provided by a container can be contained in any fixed and tangible medium. For example, the information can be part of a leaflet, brochure, or other printed material provided with a container or separate from a container. The information can also take the form of a flyer, advertisement, or the label for marketing the active agent approved by a regulatory agency. The information can also be recorded on a compact disk, DVD or any other recording or electronic medium.

The container can be in the form of bubble or blister pack cards, optionally arranged in a desired order for a particular dosing regimen. Suitable blister packs that can be arranged in a variety of configurations to accommodate a particular dosing regimen are well known in the art or easily ascertained by one of ordinary skill in the art.

Metaxalone dosage forms existing as liquids, solutions, emulsions, or suspensions can be packaged in a container for convenient dosing of pediatric or geriatric patients. For example, prefilled droppers (such as eye droppers or the like), prefilled syringes, and similar containers housing the liquid, solution, emulsion, or suspension form are contemplated.

The substance used with metaxalone in the methods and articles of manufactures described herein may have certain effects, direct or indirect, on the activity of a cytochrome p450 enzyme. The substance or metaxalone can be a substrate, inhibitor, or inducer of a Phase I or Phase II metabolic enzyme; specifically, the substance or metaxalone is a substrate, inhibitor, or inducer of a cytochrome p450 isozyme. More specifically, the substance can be a substrate of CYP1A2, CYP2B6, CYP2C9, CYP2C19, CYP2D6, CYP2E1, or CYP3A4, or an inhibitor or inducer of CYP1A2, CYP2C8, CYP2C9, CYP2C19, CYP2D6, CYP2E1, or CYP3A. For example in certain embodiments the substance is: a substrate, inhibitor, or inducer of a cytochrome p450 isozyme; an active agent; a substrate, inhibitor, or inducer of CYP1A2, CYP2C8, CYP2C9, CYP2C19, CYP2D6, CYP2E1, or CYP3A activity; an active agent with a narrow therapeutic index; an inducer of CYP1A2, CYP2C8, CYP2C9, CYP2C19, CYP2D6, CYP2E1, or CYP3A activity and plasma concentration of metaxalone can decrease; an inhibitor of CYP1A2, CYP2C8, CYP2C9, CYP2C19, CYP2D6, CYP2E1, or CYP3A and plasma concentration of metaxalone can increase; a substrate of CYP1A2, CYP2C8, CYP2C9, CYP2C19, CYP2D6, CYP2E1, or CYP3A and plasma concentration of the substance or metaxalone can increase; a substrate of CYP1A2, CYP2B6, CYP2C9, CYP2C19, CYP2D6, CYP2E1, or CYP3A4 and plasma concentration of the substance can increase; or the substance is a substrate of CYP1A2 or CYP3A4 and plasma concentration of the substance can decrease when the substance is administered with metaxalone.

In any of the above methods or articles, the substance can be an active agent.

Examples of substrates of CYP1A2 include amitriptyline, caffeine, clomipramine, clozapine, cyclobenzaprine, estradiol, fluvoxamine, haloperidol, imipramine, mexiletine, naproxen, olanzapine, ondansetron, phenacetin, acetaminophen, propranolol, riluzole, ropivacaine, tacrine, theophylline, tizanidine, verapamil, (R)-warfarin, zileuton, and zolmitriptan. Examples of active agents that are inhibitors of CYP1A2 include amiodarone, cimetidine, a fluoroquinolone (e.g., ciprofloxacin, gatifloxacin, levofloxacin, lomefloxacin, moxifloxacin, norfloxacin, or ofloxacin), fluvoxamine, furafylline, interferon, methoxsalen, and mibefradil.

Examples of inducers of CYP1A2 include chemicals released from digestion of broccoli, brussel sprouts, and char-grilled meat; chemicals inhaled when smoking tobacco; insulin, methyl cholanthrene, modafinil, nafcillin, beta-naphthoflavone, and omeprazole.

Examples of substrates of CYP2C19 include the proton pump inhibitors: lansoprazole, omeprazole, pantoprazole, and E-3810; the anti-epileptics: diazepam, phenytoin, fosphenytoin, S-mephenytoin, and phenobarbitone (Phenobarbital); as well as amitriptyline, carisoprodol, citalopram, clomipramine, cyclophosphamide, hexobarbital, imipramine, indomethacin, R-mephobarbital, moclobemide, nelfinavir, nilutamide, primidone, progesterone, proguanil, propranolol, teniposide, and R-warfarin. Examples of inhibitors of CYP2C19 include chloramphenicol, cimetidine, felbamate, fluoxetine, fluvoxamine, indomethacin, ketoconazole, lansoprazole, modafinil, omeprazole, oxcarbazepine, probenicid, ticlopidine, and topiramate. Examples of inducers of CYP2C19 include carbamazepine, norethindrone, prednisone, and rifampin (rifampicin).

Examples of substrates of CYP2B6 include bupropion, cyclophosphamide, efavirenz, ifosfamide, and methadone.

Examples of inhibitors of CYP2C8 include quercetin, a glitazone (e.g., rosiglitazone or pioglitazone), gemfibrozil, montelukast, and trimethoprim. Examples of inducers of CYP2C8 include rifampin.

Examples of substrates of CYP2C9 include diclofenac, ibuprofen, meloxicam, S-naproxen, piroxicam, suprofen, tolbutamide, glipizide, losartan, irbesartan, glyburide (glibenclamide), glipizide, glimepiride, amitriptyline, celecoxib, fluoxetine, fluvastatin, nateglinide, phenytoin, rosiglitazone, tamoxifen, torsemide, and S-warfarin. Examples of inhibitors of CYP2C9 include amiodarone, fenofibrate, fluconazole, fluvastatin, fluvoxamine, isoniazid, lovastatin, phenylbutazone, probenicid, sertraline, sulfamethoxazole, sulfaphenazole, teniposide, voriconazole, and zafirlukast. Examples of inducers of CYP2C9 include rifampin and secobarbital.

Examples of substrates of CYP2D6 include carvedilol, S-metoprolol, propafenone, timolol; amitriptyline, clomipramine, desipramine, imipramine, paroxetine; haloperidol, perphenazine, risperidone, thioridazine; alprenolol, amphetamine, aripiprazole, atomoxetine, bufuralol, chlorpheniramine, chlorpromazine, codeine, debrisoquine, dexfenfluramine, dextromethorphan, duloxetine, encainide, flecainide, fluoxetine, fluvoxamine, lidocaine, metoclopramide, methoxyamphetamine, mexiletine, minaprine, nebivolol, nortriptyline, ondansetron, perhexiline, phenacetin, phenformin, propranolol, sparteine, tamoxifen, tramadol, and venlafaxine. Examples of inhibitors of CYP2D6 include amiodarone, bupropion, celecoxib, chlorpromazine, chlorpheniramine, cimetidine, citalopram, clomipramine, cocaine, doxepin, doxorubicin, duloxetine, escitalopram, fluoxetine, halofantrine, red-haloperidol, levomepromazine, metoclopramide, methadone, mibefradil, midodrine, moclobemide, paroxetine, quinidine, ranitidine, ritonavir, sertraline, terbinafine, ticlopidine, histamine H1 receptor antagonists, diphenhydramine, chlorpheniramine, clemastine, perphenazine, hydroxyzine, and tripelennamine. Examples of inducers of CYP2D6 include rifampicin and dexamethasone.

Examples of substrates of CYP2E1 include enflurane, halothane, isoflurane, methoxyflurane, sevoflurane; acetaminophen, aniline, benzene, chlorzoxazone, ethanol, N,N-dimethyl formamide, and theophylline. Examples of inhibitors of CYP2E1 include diethyl-dithiocarbamate and disulfiram. Examples of inducers of CYP2E1 include ethanol and isoniazid.

Examples of substrates of CYP3A4 include clarithromycin, erythromycin, telithromycin: quinidine; alprazolam, diazepam, midazolam, triazolam; cyclosporine, tacrolimus (FK506); indinavir, nelfinavir, ritonavir, saquinavir; cisapride; astemizole, chlorpheniramine, terfenadine; amlodipine, diltiazem, felodipine, lercanidipine, nifedipine, nisoldipine, nitrendipine, verapamil; atorvastatin, cerivastatin, lovastatin, simvastatin; estradiol, hydrocortisone, progesterone, testosterone; alfentanyl, aripiprazole, buspirone, cafergot, caffeine, cilostazol, cocaine, codeine, dapsone, dextromethorphan, docetaxel, domperidone, eplerenone, fentanyl, finasteride, gleevec, haloperidol, irinotecan, Levo-Alpha Acetyl Methadol (LAAM), lidocaine, methadone, nateglinide, odanestron, pimozide, propranolol, quinine, salmeterol, sildenafil, sirolimus, tamoxifen, taxol, terfenadine, trazodone, vincristine, zaleplon, and zolpidem. Examples of inhibitors of CYP3A4 include HIV Antivirals (e.g., delavirdine, indinavir, nelfinavir, and ritonavir); amiodarone, aprepitant, cinchloramphenicol, cimetidine, clarithromycin, diethyl-dithiocarbamate, diltiazem, erythromycin, fluconazole, fluvoxamine, gestodene, grapefruit juice, Seville orange juice, imatinib, itraconazole, ketoconazole, mifepristone, nefazodone, norfloxacin, norfluoxetine, mibefradil, star fruit, verapamil, and voriconazole. Examples of inducers of CYP3A4 include HIV Antivirals (e.g., efavirenz, and nevirapine); barbiturates (e.g., allobarbital, amobarbital, aprobarbital, alphenal, barbital, brallobarbital, mephobarbital, secobarbital, and phenobarbital), carbamazepine, efavirenz, glucocorticoids (e.g., prednisone, prednisilone, methylprednisilone, dexamethasone, and hydrocortisone), modafinil, nevirapine, phenytoin, rifampin, St. John's wort, troglitazone, oxcarbazepine, pioglitazone, and rifabutin.

In any of the embodiments described herein, the substance can be a sensitive plasma concentration profile active agent. Examples of a sensitive plasma concentration profile active agent include cyclophosphamide, efavirenz, fosphenytoin, glimepiride, mexiletine, phenytoin, progesterone, tamoxifen, theophylline, warfarin, and any active agent having a narrow therapeutic index.

In any of the embodiments described herein, the substance can be an active agent having a narrow therapeutic index. Examples of narrow therapeutic index active agents include warfarin, phenytoin, fosphenytoin, thioridazine, theophylline, cyclosporine, and pimozide.

In some embodiments, the active agent comprises warfarin. Warfarin, 3-(α-acetonylbenzyl)-4-hydroxycoumarin, is an anticoagulant, which is eliminated by metabolism by cytochrome p450 isoforms including CYP2C9, CYP2C19, CYP2C8, CYP2C18, CYP1A2, and CYP3A4. Warfarin has a narrow therapeutic index such that too little can lead to excessive clotting, while excessive warfarin can lead to excessive bleeding. The dosing of warfarin is individualized according to the patient's sensitivity to the active agent as indicated, for example, by the Prothrombin Time/International Normalized Ratio (PT/INR). The PT/INR gives an indication of how fast blood is clotting. The recommended initial dose is 2-5 mg/day, with 2-10 mg/day as the maintenance dose. Warfarin tablets for oral administration include tablets comprising 1, 2, 2.5, 3, 4, 5, 6, 7.5, and 10 mg of warfarin. The INR may be adjusted to 2.0-4.5, or 2.0-3.0 or 2.5-3.5 depending on whether the warfarin is being administered to treat venous thromboembolism, non-valvular atrial fibrillation, post-myocardial infarction, heart valve prophylaxis, or recurrent systemic embolism.

In the PT test, a reagent which induces coagulation is added to a sample of the patient's plasma. The reagent typically primarily comprises thromboplastin and calcium chloride. Many commercially available PT reagents contain crude thromboplastin extracted from natural sources, e.g., rabbit brain, rabbit brain/lung mixtures, human placenta, or bovine brain, although recombinant thromboplastin may also be employed. Prothrombin time assays are performed by mixing the plasma sample and reagent at a constant temperature such as 37° C., and monitoring the progress of the reaction until a perceptible clot (or "gel clot") is detected. The development of a gel clot is the end point of the reaction. This end point may be detected in various ways such as by viscosity change, by electrode reaction, and, most commonly, by photometric means. The test result is generally compared to a result using a normal (control) plasma and converted to an INR.

The International Normalized Ratio, or INR, was developed to standardize PT values, so that test results from different thromboplastins and coagulation analyzers become equivalent. Under the INR system, a thromboplastin is assigned an International Sensitivity Index (ISI) value. The ISI indicates the relative sensitivity of the thromboplastin compared to an international reference thromboplastin. If a thromboplastin has the same sensitivity as the reference thromboplastin, then its ISI is 1.0. A higher ISI value indicates that a thromboplastin is less sensitive than the reference thromboplastin. The ISI is used in the following formula to calculate an INR value from a PT value: INR=(patient PT/mean normal PT)$^{ISI}$. The ISI is usually determined by the thromboplastin manufacturer. Different ISI values are assigned for different models or classes of coagulation analyzers.

In another embodiment, the active agent comprises phenytoin. Phenytoin, 5,5-diphenylhydantoin, is an antiepileptic active agent useful in the treatment of epilepsy which is eliminated by metabolism by cytochrome p450 isoforms including CYP1A2, CYP2C9, CYP2C19, and CYP3A4. Phenytoin has a narrow therapeutic index such that too little can lead to insufficient results and excessive phenytoin can lead to phenytoin toxicity. The typical clinically effective serum level is about 10 to about 20 μg/mL. The recommended initial dose is one 100 mg capsule 3 to 4 times per day, with 300 mg/day dose in three divided doses or one single dose per day. The dosing of phenytoin can be individualized according to the patient's sensitivity to the active agent by measuring plasma concentration of phenytoin.

Methods of treating a musculoskeletal condition or head pain with metaxalone are provided herein. Such methods include informing a user that metaxalone affects the activity of a cytochrome p450 isozyme. The method may further include informing the user that administration of metaxalone with a substance can affect the plasma concentration, bioavailability, safety, efficacy, or a combination comprising at least one of the foregoing of metaxalone or the substance. The method may also include informing the user of any information disclosed herein about the effect of metaxalone or the substance on the activity of a cytochrome p450 isozyme and any information disclosed herein about the effect of metaxalone or the substance on the plasma concentration, bioavailability, safety, efficacy, or a combination comprising at least one of the foregoing of metaxalone or the substance. Methods of treatment may also include providing a user with metaxalone or administering metaxalone to a patient.

Methods of treatment include methods in which the user is a patient and additionally comprising administering metaxalone and an active agent to the patient. The patient may be, for example, a human patient, a patient in need of treatment of a musculoskeletal condition or head pain, a patient receiving prophylactic metaxalone treatment, or a patient undergoing metaxalone therapy. The amount of metaxalone administered may be a therapeutically effective amount.

Methods of treatment may additionally include monitoring the patient's plasma concentration of the active agent as $AUC_{0-INF}$, $AUC_{0-t}$, $C_{MAX}$, or a combination of any of the foregoing pharmacokinetic parameters. When metaxalone is administered together with another active agent, methods of treatment can include determining the plasma concentration of the active agent and altering dosing of the active agent for the patient based on the determined active agent plasma concentration.

In another embodiment, a method of treatment comprises administering to a patient in need of both a skeletal muscle relaxant and an anticoagulant, for example, metaxalone and warfarin, and monitoring the Prothrombin Time/International Normalized Ratio. Monitoring the Prothrombin Time/International Normalized Ratio may be performed for example daily, every other day, weekly, every other week, monthly, or according to another schedule or time criteria. The method may further comprise providing to the patient or medical care worker instructions regarding measuring the Prothrombin Time/International Normalized Ratio.

When the substance administered with metaxalone is an NTI active agent, methods using a blood test to monitor plasma levels of the NTI active agent comprise administering to a patient metaxalone and the NTI active agent, and monitoring the blood levels of the NTI active agent as $AUC_{0-t}$, $AUC_{0-INF}$, $C_{MAX}$, or a combination comprising one or more of the foregoing pharmacokinetic parameters.

In one embodiment, a method of using a blood test to monitor warfarin levels comprises administering to a patient in need of both a skeletal muscle relaxant and an anticoagulant both metaxalone and warfarin, and monitoring the blood levels of warfarin as $AUC_{0-t}$, $AUC_{0-INF}$, $C_{MAX}$, or a combination comprising one or more of the foregoing pharmacokinetic parameters.

In another embodiment, the substance is phenytoin, and a method using a blood test to monitor plasma levels of phenytoin comprise administering to a patient metaxalone and phenytoin, and monitoring the blood levels of phenytoin as $AUC_{0-t}$, $AUC_{0-INF}$, $C_{MAX}$, or a combination comprising one or more of the foregoing pharmacokinetic parameters.

In all of the embodiments herein, a medical care worker can determine the plasma concentration of an active agent by performing or ordering the performance of any suitable method. For example, the medical care worker could order a test using blood drawn from the patient for determining the plasma concentration of the active agent.

The invention is further illustrated by the following examples.

Example 1

Determination of Human Cytochrome p450 Isozymes Using Metaxalone as a Substrate

The study of this example was performed to determine the metabolism of metaxalone by human cytochrome p450 isoforms CYP1A2, CYP2A6, CYP2C9, CYP2C19, CYP2D6, CYP2E1, and CYP3A4. Microsomes containing singly-expressed human CYP isoforms were incubated in the presence of metaxalone. The metabolism of metaxalone was evaluated by measuring the disappearance of metaxalone by high-performance liquid chromatography (HPLC).

Commercially available microsomes from baculovirus-infected insect cells containing singly-expressed recombinant wild-type (*1 allele) human CYP enzymes and cDNA-expressed human cytochrome p450 oxidoreductase [BD SUPERSOMES Enzymes; BD Biosciences Discovery Labware (Woburn, Mass.)] were used. For CYP2A6, CYP2C9, CYP2C19, and CYP2E1, the SUPERSOMES also expressed human cytochrome b5 in addition to human cytochrome p450 oxidoreductase and the human CYP isozyme.

Metaxalone stock solutions were prepared in methanol at 100 times (100×) the final concentration. The stock solutions were added to incubation mixtures to obtain final concentrations of 0.5, 2.5, and 25 µM (corresponding to 111, 552, and 5530 ng metaxalone/mL, respectively), each containing 1% methanol. All incubations were conducted at 37±1° C. in a shaking water bath with a sample size of N=3 replicates for each experimental group. Incubation mixtures of microsomes (corresponding to 10 pmol p450) and metaxalone were prepared in 0.1 M Tris buffer. After a 5-minute pre-incubation, an NADPH regenerating system (NRS) was added to the incubation mixtures to initiate reactions, with a final incubation volume of 0.5 mL. Incubations were continued for 30 minutes, and then terminated, except for those for CYP2C19, which were incubated for 36 minutes prior to termination. Samples were then analyzed for metaxalone.

Positive controls with a suitable isoform-selective substrate were performed for each CYP isoform to verify metabolic activity. Concentration of metabolites formed from CYP isoform-selective substrates in the positive control samples was analyzed using liquid chromatography/mass spectrometry (LC/MS) or HPLC, as appropriate. A table of the substrate, substrate concentration, solvent, metabolite formed, and metabolite assay method for each CYP isozyme studied is below.

| CYP isoform | Isoform-selective substrate | Substrate concentration | Solvent | Metabolite formed | Metabolite Assay |
|---|---|---|---|---|---|
| CYP1A2 | Phenacetin | 50 µM | ACN | Acetaminophen | LC/MS |
| CYP2A6 | Coumarin | 8 µM | ACN | 7-hydroxy coumarin | HPLC-UV |
| CYP2C9 | Tolbutamide | 150 µM | ACN | 4'-methylhydroxy tolbutamide | LC/MS |
| CYP2C19 | S-Mephenytoin | 50 µM | ACN | 4'-hydroxy mephenytoin | LC/MS |
| CYP2D6 | Dextromethorphan | 5 µM | Water | dextrorphan | LC/MS |
| CYP2E1 | Chlorzoxazone | 50 µM | ACN | 6-hydroxy chlorzoxazone | LC/MS |
| CYP3A4 | Testosterone | 100 µM | ACN | 6β-hydroxy testosterone | HPLC-UV |

Matrix controls were performed to determine the background signal from the matrix components (microsomes (10 pmol p450), 0.1N Tris buffer, NRS, and 1% methanol). Additionally metabolic negative controls were performed to distinguish potential nonenzymatic metabolism of metaxalone from p450-mediated metabolism. Incubation mixtures were prepared in 0.1 M Tris buffer with SUPERSOMES (10 pmol P450) and metaxalone (at each concentration). After a 5-minute pre-incubation, 2% sodium bicarbonate solution was added to the incubation mixtures. Incubation was for 30 minutes at a final volume of 0.5 mL. Matrix and metabolic negative controls were terminated by adding an equal volume of methanol. The matrix control and metabolic negative control samples were analyzed for metaxalone by HPLC. Analysis of samples was subsequent to storage at −70° C.

Results are presented for each studied human cytochrome p450 isozyme in Tables 2-8.

TABLE 2

Metabolism of Metaxalone by Expressed Recombinant Human CYP1A2

| Metaxalone Concentration ($\mu$M) | Metaxalone Present | | | Percent of Metabolic Negative Control | |
|---|---|---|---|---|---|
| | Raw ($\mu$M) | Adjusted ($\mu$M) | | | |
| | | Individual | Mean ± SD | Individual | Mean ± SD |
| MNC (0.5) | 0.20195 | 0.404 | 0.391 ± 0.0113 | 103 | 100 ± 2.88 |
| | 0.19430 | 0.389 | | 99.3 | |
| | 0.19097 | 0.382 | | 97.6 | |
| 0.5 | 0.15087 | 0.302 | 0.352 ± 0.0761 | 77.1 | 89.9 ± 19.4 |
| | 0.21975 | 0.440 | | 112 | |
| | 0.15734 | 0.315 | | 80.4 | |
| MNC (2.5) | 0.65183 | 1.30 | 1.33 ± 0.0221 | 98.3 | 100 ± 1.67 |
| | 0.66350 | 1.33 | | 100 | |
| | 0.67394 | 1.35 | | 102 | |
| 2.5 | 0.52700 | 1.05 | 1.07 ± 0.0167 | 79.5 | 80.4 ± 1.26 |
| | 0.52908 | 1.06 | | 79.8 | |
| | 0.54235 | 1.08 | | 81.8 | |
| MNC (25) | 10.11453 | 20.2 | 19.8 ± 0.360 | 102 | 100 ± 1.82 |
| | 9.76568 | 19.5 | | 98.5 | |
| | 9.86156 | 19.7 | | 99.5 | |
| 25 | 8.20521 | 16.4 | 16.6 ± 0.337 | 82.8 | 83.7 ± 1.70 |
| | 8.19232 | 16.4 | | 82.6 | |
| | 8.49030 | 17.0 | | 85.6 | |
| MXC (0) | 0.00000[a] | N/A | N/A ± N/A | N/A | N/A ± N/A |
| | 0.00000[a] | N/A | | N/A | |
| | 0.00000[a] | N/A | | N/A | |

Abbreviations:
SD, standard deviation;
MNC, metabolic negative control;
MXC, matrix control;
N/A, not applicable
[a]The Raw value ($\mu$M) was below the lowest concentration on the standard curve (0.05 $\mu$M).
Note:
For all calculations above, the resulting values are shown with at least three significant figures for display purposes only.

TABLE 3

Metabolism of Metaxalone by Expressed Recombinant Human CYP2A6

| Metaxalone Concentration ($\mu$M) | Metaxalone Present | | | Percent of Metabolic Negative Control | |
|---|---|---|---|---|---|
| | Raw ($\mu$M) | Adjusted ($\mu$M) | | | |
| | | Individual | Mean ± SD | Individual | Mean ± SD |
| MNC (0.5) | 0.15455 | 0.309 | 0.311 ± 0.00446 | 99.4 | 100 ± 1.43 |
| | 0.15795 | 0.316 | | 102 | |
| | 0.15375 | 0.308 | | 98.9 | |
| 0.5 | 0.15457 | 0.309 | 0.299 ± 0.0124 | 99.5 | 96.1 ± 3.99 |
| | 0.15112 | 0.302 | | 97.2 | |
| | 0.14253 | 0.285 | | 91.7 | |
| MNC (2.5) | 0.74261 | 1.49 | 1.52 ± 0.0353 | 97.9 | 100 ± 2.33 |
| | 0.75568 | 1.51 | | 99.6 | |
| | 0.77755 | 1.56 | | 102 | |
| 2.5 | 0.79130 | 1.58 | 1.61 ± 0.0373 | 104 | 106 ± 2.46 |
| | 0.79791 | 1.60 | | 105 | |
| | 0.82642 | 1.65 | | 109 | |
| MNC (25) | 7.74594 | 15.5 | 15.3 ± 0.147 | 101 | 100 ± 0.959 |
| | 7.64948 | 15.3 | | 99.8 | |
| | 7.60163 | 15.2 | | 99.2 | |

TABLE 3-continued

Metabolism of Metaxalone by Expressed Recombinant Human CYP2A6

| Metaxalone Concentration (μM) | Raw (μM) | Metaxalone Present Adjusted (μM) | | Percent of Metabolic Negative Control | |
|---|---|---|---|---|---|
| | | Individual | Mean ± SD | Individual | Mean ± SD |
| 25 | 7.76399 | 15.5 | 15.6 ± 0.0975 | 101 | 102 ± 0.636 |
| | 7.85044 | 15.7 | | 102 | |
| | 7.84628 | 15.7 | | 102 | |
| MXC | 0.00000[a] | N/A | N/A ± N/A | N/A | N/A ± N/A |
| (0) | 0.00000[a] | N/A | | N/A | |
| | 0.00000[a] | N/A | | N/A | |

Abbreviations:
SD, standard deviation;
MNC, metabolic negative control;
MXC, matrix control;
N/A, not applicable

[a]The Raw value (μM) was below the lowest concentration on the standard curve (0.05 μM)

Note:
For all calculations above, the resulting values are shown with at least three significant figures for display purposes only.

TABLE 4

Metabolism of Metaxalone by Expressed Recombinant Human CYP2C9

| Metaxalone Concentration (μM) | Raw (μM) | Metaxalone Present Adjusted (μM) | | Percent of Metabolic Negative Control | |
|---|---|---|---|---|---|
| | | Individual | Mean ± SD | Individual | Mean ± SD |
| MNC | 0.17052 | 0.341 | 0.348 ± 0.00997 | 97.9 | 100 ± 2.86 |
| (0.5) | 0.17229 | 0.345 | | 98.9 | |
| | 0.17990 | 0.360 | | 103 | |
| 0.5 | 0.18004 | 0.360 | 0.355 ± 0.00608 | 103 | 102 ± 1.75 |
| | 0.17784 | 0.356 | | 102 | |
| | 0.17403 | 0.348 | | 99.9 | |
| MNC | 0.93197 | 1.86 | 1.93 ± 0.0605 | 96.8 | 100 ± 3.14 |
| (2.5) | 0.96526 | 1.93 | | 100 | |
| | 0.99235 | 1.98 | | 103 | |
| 2.5 | 0.96842 | 1.94 | 1.92 ± 0.0246 | 101 | 99.7 ± 1.28 |
| | 0.96593 | 1.93 | | 100 | |
| | 0.94597 | 1.89 | | 98.2 | |
| MNC | 10.31249 | 20.6 | 21.3 ± 0.620 | 97.1 | 100 ± 2.92 |
| (25) | 10.63201 | 21.3 | | 100 | |
| | 10.93245 | 21.9 | | 103 | |
| 25 | 10.66111 | 21.3 | 21.5 ± 0.144 | 100 | 101 ± 0.675 |
| | 10.80454 | 21.6 | | 102 | |
| | 10.72836 | 21.5 | | 101 | |
| MXC | 0.00000[a] | N/A | N/A ± N/A | N/A | N/A ± N/A |
| (0) | 0.00000[a] | N/A | | N/A | |
| | 0.00000[a] | N/A | | N/A | |

Abbreviations:
SD, standard deviation;
MNC, metabolic negative control;
MXC, matrix control;
N/A, not applicable

[a]The Raw value (μM) was below the lowest concentration on the standard curve (0.05 μM)

Note:
For all calculations above, the resulting values are shown with at least three significant figures for display purposes only.

TABLE 5

Metabolism of Metaxalone by Expressed Recombinant Human CYP2C19

| Metaxalone Concentration (µM) | Raw (µM) | Metaxalone Present Adjusted (µM) Individual | Mean ± SD | Percent of Metabolic Negative Control Individual | Mean ± SD |
|---|---|---|---|---|---|
| MNC (0.5) | 0.18718 | 0.374 | 0.370 ± 0.00898 | 101 | 100 ± 2.43 |
|  | 0.18763 | 0.375 |  | 102 |  |
|  | 0.17964 | 0.359 |  | 97.2 |  |
| 0.5 | 0.16773 | 0.335 | 0.345 ± 0.0104 | 90.8 | 93.4 ± 2.82 |
|  | 0.17180 | 0.344 |  | 93.0 |  |
|  | 0.17808 | 0.356 |  | 96.4 |  |
| MNC (2.5) | 0.72720 | 1.45 | 1.39 ± 0.0560 | 105 | 100 ± 4.03 |
|  | 0.67562 | 1.35 |  | 97.2 |  |
|  | 0.68261 | 1.37 |  | 98.2 |  |
| 2.5 | 0.67218 | 1.34 | 1.34 ± 0.00561 | 96.7 | 96.5 ± 0.404 |
|  | 0.67254 | 1.35 |  | 96.7 |  |
|  | 0.66751 | 1.34 |  | 96.0 |  |
| MNC (25) | 9.84488 | 19.7 | 20.1 ± 1.03 | 97.8 | 100 ± 5.13 |
|  | 9.69255 | 19.4 |  | 96.3 |  |
|  | 10.65287 | 21.3 |  | 106 |  |
| 25 | 9.34508 | 18.7 | 18.6 ± 0.120 | 92.9 | 92.6 ± 0.597 |
|  | 9.35948 | 18.7 |  | 93.0 |  |
|  | 9.24903 | 18.5 |  | 91.9 |  |
| MXC (0) | 0.00000[a] | N/A | N/A ± N/A | N/A | N/A ± N/A |
|  | 0.00000[a] | N/A |  | N/A |  |
|  | 0.06454 | N/A |  | N/A |  |

Abbreviations:
SD, standard deviation;
MNC, metabolic negative control;
MXC, matrix control;
N/A, not applicable
[a]The Raw value (µM) was below the lowest concentration on the standard curve (0.05 µM)
Note:
For all calculations above, the resulting values are shown with at least three significant figures for display purposes only.

TABLE 6

Metabolism of Metaxalone by Expressed Recombinant Human CYP2D6

| Metaxalone Concentration (µM) | Raw (µM) | Metaxalone Present Adjusted (µM) Individual | Mean ± SD | Percent of Metabolic Negative Control Individual | Mean ± SD |
|---|---|---|---|---|---|
| MNC (0.5) | 0.14509 | 0.290 | 0.292 ± 0.00220 | 99.4 | 100 ± 0.755 |
|  | 0.14716 | 0.294 |  | 101 |  |
|  | 0.14547 | 0.291 |  | 99.7 |  |
| 0.5 | 0.18683 | 0.374 | 0.319 ± 0.0477 | 128 | 109 ± 16.3 |
|  | 0.14857 | 0.297 |  | 102 |  |
|  | 0.14305 | 0.286 |  | 98.0 |  |
| MNC (2.5) | 0.79025 | 1.58 | 1.56 ± 0.0184 | 101 | 100 ± 1.18 |
|  | 0.78433 | 1.57 |  | 100 |  |
|  | 0.77221 | 1.54 |  | 98.7 |  |
| 2.5 | 0.75826 | 1.52 | 1.53 ± 0.0111 | 96.9 | 97.7 ± 0.707 |
|  | 0.76852 | 1.54 |  | 98.2 |  |
|  | 0.76697 | 1.53 |  | 98.0 |  |
| MNC (25) | 9.63762 | 19.3 | 19.2 ± 0.0994 | 100 | 100 ± 0.517 |
|  | 9.54788 | 19.1 |  | 99.4 |  |
|  | 9.62976 | 19.3 |  | 100 |  |
| 25 | 9.52577 | 19.1 | 19.2 ± 0.436 | 99.2 | 99.9 ± 2.27 |
|  | 9.84529 | 19.7 |  | 103 |  |
|  | 9.42917 | 18.9 |  | 98.2 |  |

TABLE 6-continued

Metabolism of Metaxalone by Expressed Recombinant Human CYP2D6

| Metaxalone Concentration (μM) | Metaxalone Present | | | Percent of Metabolic Negative Control | |
|---|---|---|---|---|---|
| | Raw (μM) | Adjusted (μM) | | | |
| | | Individual | Mean ± SD | Individual | Mean ± SD |
| MXC (0) | 0.00000[a] | N/A | N/A ± N/A | N/A | N/A ± N/A |
| | 0.00000[a] | N/A | | N/A | |
| | 0.00000[a] | N/A | | N/A | |

Abbreviations:
SD, standard deviation;
MNC, metabolic negative control;
MXC, matrix control;
N/A, not applicable

[a] The Raw value (μM) was below the lowest concentration on the standard curve (0.05 μM)

Note:
For all calculations above, the resulting values are shown with at least three significant figures for display purposes only.

TABLE 7

Metabolism of Metaxalone by Expressed Recombinant Human CYP2E1

| Metaxalone Concentration (μM) | Metaxalone Present | | | Percent of Metabolic Negative Control | |
|---|---|---|---|---|---|
| | Raw (μM) | Adjusted (μM) | | | |
| | | Individual | Mean ± SD | Individual | Mean ± SD |
| MNC (0.5) | 0.18358 | 0.367 | 0.355 ± 0.0104 | 103 | 100 ± 2.92 |
| | 0.17510 | 0.350 | | 98.6 | |
| | 0.17416 | 0.348 | | 98.1 | |
| 0.5 | 0.17871 | 0.357 | 0.352 ± 0.00648 | 101 | 99.0 ± 1.83 |
| | 0.17235 | 0.345 | | 97.0 | |
| | 0.17662 | 0.353 | | 99.4 | |
| MNC (2.5) | 0.89075 | 1.78 | 1.69 ± 0.117 | 105 | 100 ± 6.89 |
| | 0.77998 | 1.56 | | 92.2 | |
| | 0.86695 | 1.73 | | 102 | |
| 2.5 | 0.88299 | 1.77 | 1.76 ± 0.00318 | 104 | 104 ± 0.188 |
| | 0.87990 | 1.76 | | 104 | |
| | 0.88209 | 1.76 | | 104 | |
| MNC (25) | 9.11125 | 18.2 | 17.8 ± 0.410 | 103 | 100 ± 2.30 |
| | 8.70811 | 17.4 | | 98.0 | |
| | 8.84728 | 17.7 | | 99.5 | |
| 25 | 8.73183 | 17.5 | 19.2 ± 2.71 | 98.2 | 108 ± 15.3 |
| | 11.15149 | 22.3 | | 125 | |
| | 8.87878 | 17.8 | | 99.9 | |
| MXC (0) | 0.00000[a] | N/A | N/A ± N/A | N/A | N/A ± N/A |
| | 0.00000[a] | N/A | | N/A | |
| | 0.00000[a] | N/A | | N/A | |

Abbreviations:
SD, standard deviation;
MNC, metabolic negative control;
MXC, matrix control;
N/A, not applicable

[a] The Raw value (μM) was below the lowest concentration on the standard curve (0.05 μM)

Note:
For all calculations above, the resulting values are shown with at least three significant figures for display purposes only.

TABLE 8

Metabolism of Metaxalone by Expressed Recombinant Human CYP3A4

| Metaxalone Concentration (μM) | Raw (μM) | Adjusted (μM) Individual | Adjusted (μM) Mean ± SD | Percent of Metabolic Negative Control Individual | Percent of Metabolic Negative Control Mean ± SD |
|---|---|---|---|---|---|
| MNC (0.5) | 0.16014 | 0.320 | 0.318 ± 0.00502 | 101 | 100 ± 1.58 |
|  | 0.15592 | 0.312 |  | 98.2 |  |
|  | 0.16039 | 0.321 |  | 101 |  |
| 0.5 | 0.15978 | 0.320 | 0.320 ± 0.00333 | 101 | 101 ± 1.05 |
|  | 0.16159 | 0.323 |  | 102 |  |
|  | 0.15826 | 0.317 |  | 99.6 |  |
| MNC (2.5) | 0.85285 | 1.71 | 1.72 ± 0.0127 | 99.3 | 100 ± 0.741 |
|  | 0.86553 | 1.73 |  | 101 |  |
|  | 0.85828 | 1.72 |  | 99.9 |  |
| 2.5 | 0.85730 | 1.71 | 1.68 ± 0.0289 | 99.8 | 98.0 ± 1.68 |
|  | 0.82923 | 1.66 |  | 96.5 |  |
|  | 0.83738 | 1.67 |  | 97.5 |  |
| MNC (25) | 8.65154 | 17.3 | 17.4 ± 0.0906 | 99.4 | 100 ± 0.521 |
|  | 8.71767 | 17.4 |  | 100 |  |
|  | 8.73830 | 17.5 |  | 100 |  |
| 25 | 8.53809 | 17.1 | 17.1 ± 0.192 | 98.1 | 98.1 ± 1.10 |
|  | 8.44686 | 16.9 |  | 97.1 |  |
|  | 8.63905 | 17.3 |  | 99.3 |  |
| MXC (0) | 0.00000[a] | N/A | N/A ± N/A | N/A | N/A ± N/A |
|  | 0.00000[a] | N/A |  | N/A |  |
|  | 0.00000[a] | N/A |  | N/A |  |

Abbreviations:
SD, standard deviation;
MNC, metabolic negative control;
MXC, matrix control;
N/A, not applicable

[a] The Raw value (μM) was below the lowest concentration on the standard curve (0.05 μM)

Note:
For all calculations above, the resulting values are shown with at least three significant figures for display purposes only.

Tables 2 and 5 show the results for human CYP1A2 and CYP2C19, respectively. The results for these two cytochrome p450 isozymes show that metaxalone is a substrate for the enzymatic activity of both CYP1A2 and CYP2C19.

Disappearance of metaxalone was detected following incubation with CYP1A2 in the presence of the NADPH-regenerating system. Disappearance of metaxalone ranged from 10.1% to 19.6% (Table 2). The difference from the starting amount is statistically significant at 2.5 and 25 μM using an unpaired two-tailed t-test ($p \leq 0.05$). These results indicate that CYP1A2 is involved in the metabolism of metaxalone.

In the experiments with CYP2C19, metaxalone disappearance was evident following incubation with metaxalone at all three concentrations (Table 5). The mean disappearance of metaxalone was 6.6% for the reaction using 0.5 μM metaxalone; the reduction in the mean amount of metaxalone from the value for the corresponding metabolic negative control was statistically significant ($p \leq 0.05$) using an unpaired two-tailed t-test. The amount of the disappearance of metaxalone observed at 2.5 or 25 μM was not statistically significant ($p > 0.05$) compared to the mean values for the corresponding metabolic negative controls using a two-tailed t-test. These results indicate that CYP2C19 is also involved in the metabolism of metaxalone, though to a lesser extent than CYP1A2.

Experiments with the other tested cytochrome p450 isozymes (Tables 3-4 and 6-8) failed to show any statistically significant disappearance of metaxalone following incubation at the standard conditions, indicating that, within the limits of detection for these experiments, metaxalone was not used as a substrate by the other tested cytochrome p450 isozymes: CYP2A6, CYP2C9, CYP2D6, CYP2E1, and CYP3A4.

Example 2

Metaxalone Inhibition of Cytochrome p450 Isozymes in Human Microsomes

The study of this example was performed to determine the potential of metaxalone to inhibit the activities of cytochrome p450 (CYP) isoforms CYP1A2, CYP2A6, CYP2B6, CYP2C8, CYP2C9, CYP2C19, CYP2D6, CYP2E1, and CYP3A4 in human liver microsomes. Human liver microsomes were incubated in the presence of metaxalone and a substrate selective for each CYP isoform. A table of the substrate, substrate concentration, solvent, metabolite formed and metabolite assay method for each CYP isozyme studied is below.

| CYP isoform | Isoform-selective substrate | Substrate concentration | Solvent | Metabolite formed | Metabolite Assay |
|---|---|---|---|---|---|
| CYP1A2 | Phenacetin | 50 μM | ACN | acetaminophen | LC/MS |
| CYP2A6 | Coumarin | 8 μM | ACN | 7-hydroxy coumarin | HPLC-UV |
| CYP2B6 | S-Mephenytoin | 1 mM | ACN | nirvanol | LC/MS |
| CYP2C8 | Paclitaxel | 5 μM | ACN | 6-hydroxy paclitaxel | LC/MS |
| CYP2C9 | Tolbutamide | 150 μM | ACN | 4'-methylhydroxytolbutamide | LC/MS |
| CYP2C19 | S-Mephenytoin | 50 μM | ACN | 4'-hydroxy mephenytoin | LC/MS |
| CYP2D6 | Dextromethorphan | 5 μM | Water | dextrorphan | LC/MS |
| CYP2E1 | Chlorzoxazone | 50 μM | ACN | 6-hydroxy chlorzoxazone | LC/MS |
| CYP3A4 | Testosterone | 100 μM | ACN | 6β-hydroxy testosterone | HPLC-UV |

Metaxalone stock solutions were prepared in methanol at 100 times (100×) the final concentration and added to incubation mixtures to obtain final concentrations of 0.3, 1, 3, 30, and 100 μM (corresponding to 66.3, 221, 663, 6630 and 22,100 ng metaxalone/mL, respectively), each containing 1% methanol.

Microsomes were prepared by differential centrifugation of liver homogenates pooled from at least ten human donors.

All metaxalone incubations were conducted at 37±1° C. in a shaking water bath using a sample size of N=3 replicates for experimental groups. Incubation mixtures were prepared in 0.1 M Tris buffer and contained microsomes (0.25 mg protein/mL for CYP2C9, CYP2D6, CYP2E1, and CYP3A4; 0.5 mg protein/mL for CYP1A2, CYP2A6, CYP2B6, CYP2C8, and CYP2C19), metaxalone (at each concentration), and a CYP isoform-selective substrate. After a 5 minute preincubation, NADPH regenerating system (NRS) was added to initiate the reaction. CYP2A6 and CYP3A4 incubations were for 10 minutes. All other incubations were for 30 minutes.

Incubations for CYP2C8 were terminated by adding 1.0 mL of ACN, while all other incubations were terminated by adding 1.0 mL of methanol. Samples were transferred to cryovials and analyzed after storage at −70° C. Triplicate replicates were performed for each concentration of metaxalone for each cytochrome p450 isozyme.

To verify that the test system was responsive to inhibitors, a positive control using 1 μM ketoconazole, a selective inhibitor of CYP3A4, was added to CYP3A4 microsome incubations with 100 μM testosterone. Four replicates were performed. The test system was considered responsive to inhibitors since the mean specific activity of CYP3A4 in the positive control samples treated with ketoconazole was <14% of the mean specific activity in the corresponding vehicle control samples.

Vehicle control experiments were performed to establish a baseline value for enzyme activity. Incubation mixtures were prepared in 0.1 M Tris buffer with microsomes (0.25 mg protein/mL for CYP2C9, CYP2D6, CYP2E1, and CYP3A4; 0.5 mg protein/mL for CYP1A2, CYP2A6, CYP2B6, CYP2C8, and CYP2C19), 1% methanol, and a CYP isoform-selective substrate. Four replicates were performed.

Metaxalone interference control samples were also included to eliminate the possibility of interference by metaxalone or its metabolites in detection of the metabolite formed from an isoform-selective substrate. Two replicates were performed. Incubation mixtures containing microsomes (0.25 mg protein/mL for CYP2C9, CYP2D6, CYP2E1, and CYP3A4; 0.5 mg protein/mL for CYP1A2, CYP2A6, CYP2B6, CYP2C8, and CYP2C19), 100 μM metaxalone, and 1% substrate solvent were prepared in 0.1 M Tris buffer. No interference was detected in any of the metabolite assay methods used.

Results for each CYP isoform, in the presence and absence of metaxalone, are reported in Tables 9-17.

TABLE 9

CYP1A2 Activity in Pooled Human Microsomes

| Metaxalone (μM) | Acetaminophen formation | | | Specific Activity | | Percent of VC |
|---|---|---|---|---|---|---|
| | Raw (μM) | Adjusted (μM) | | (pmol/min/mg protein) | | |
| | | Individual | Mean ± SD | Individual | Mean ± SD | |
| 0 (VC) | 0.23653 | 0.237 | 0.216 ± 0.0138 | 31.5 | 28.8 ± 1.84 | 100 |
| | 0.21124 | 0.211 | | 28.2 | | |
| | 0.21156 | 0.212 | | 28.2 | | |
| | 0.20568 | 0.206 | | 27.4 | | |
| 0.3 | 0.21120 | 0.211 | 0.210 ± 0.00536 | 28.2 | 28.0 ± 0.715 | 97.2 |
| | 0.21487 | 0.215 | | 28.6 | | |
| | 0.20431 | 0.204 | | 27.2 | | |
| 1 | 0.19966 | 0.200 | 0.200 ± 0.00246 | 26.6 | 26.6 ± 0.327 | 92.3 |
| | 0.19709 | 0.197 | | 26.3 | | |
| | 0.20200 | 0.202 | | 26.9 | | |
| 3 | 0.19900 | 0.199 | 0.195 ± 0.00589 | 26.5 | 26.0 ± 0.785 | 90.3 |
| | 0.18839 | 0.188 | | 25.1 | | |
| | 0.19813 | 0.198 | | 26.4 | | |
| 30 | 0.18924 | 0.189 | 0.194 ± 0.00544 | 25.2 | 25.9 ± 0.725 | 89.8 |
| | 0.19323 | 0.193 | | 25.8 | | |
| | 0.20000 | 0.200 | | 26.7 | | |

TABLE 9-continued

CYP1A2 Activity in Pooled Human Microsomes

| Metaxalone (µM) | Acetaminophen formation | | | Specific Activity | | Percent of VC |
|---|---|---|---|---|---|---|
| | Raw (µM) | Adjusted (µM) | | (pmol/min/mg protein) | | |
| | | Individual | Mean ± SD | Individual | Mean ± SD | |
| 100 | 0.17757 | 0.178 | 0.177 ± 0.000206 | 23.7 | 23.6 ± 0.0275 | 82.0 |
| | 0.17733 | 0.177 | | 23.6 | | |
| | 0.17716 | 0.177 | | 23.6 | | |

Abbreviations:
SD, standard deviation;
VC, vehicle control (1% Methanol).
Note:
For all calculations above, the resulting values are shown with at least three significant figures for display purposes only.

TABLE 10

CYP2A6 Activity in Pooled Human Microsomes

| Metaxalone (µM) | 7-Hydroxycoumarin formation | | | Specific Activity | | Percent of VC |
|---|---|---|---|---|---|---|
| | Raw (µM) | Adjusted (µM) | | (pmol/min/mg protein) | | |
| | | Individual | Mean ± SD | Individual | Mean ± SD | |
| 0 (VC) | 1.03214 | 1.03 | 1.06 ± 0.0356 | 413 | 426 ± 14.2 | 100 |
| | 1.04464 | 1.04 | | 418 | | |
| | 1.06891 | 1.07 | | 428 | | |
| | 1.11282 | 1.11 | | 445 | | |
| 0.3 | 1.07439 | 1.07 | 1.03 ± 0.0399 | 430 | 413 ± 16.0 | 96.9 |
| | 0.99553 | 0.996 | | 398 | | |
| | 1.02457 | 1.02 | | 410 | | |
| 1 | 0.99854 | 0.999 | 1.02 ± 0.0184 | 399 | 407 ± 7.36 | 95.7 |
| | 1.02269 | 1.02 | | 409 | | |
| | 1.03468 | 1.03 | | 414 | | |
| 3 | 1.05100 | 1.05 | 1.09 ± 0.0402 | 420 | 436 ± 16.1 | 102 |
| | 1.13132 | 1.13 | | 453 | | |
| | 1.08822 | 1.09 | | 435 | | |
| 30 | 1.08205 | 1.08 | 1.14 ± 0.0493 | 433 | 455 ± 19.7 | 107 |
| | 1.15129 | 1.15 | | 461 | | |
| | 1.17736 | 1.18 | | 471 | | |
| 100 | 0.98864 | 0.989 | 1.01 ± 0.0416 | 395 | 404 ± 16.6 | 94.8 |
| | 0.98209 | 0.982 | | 393 | | |
| | 1.05713 | 1.06 | | 423 | | |

Abbreviations:
SD, standard deviation;
VC, vehicle control (1% Methanol)
Note:
For all calculations above, the resulting values are shown with at least three significant figures for display purposes only.

TABLE 11

CYP2B6 Activity in Pooled Human Microsomes

| Metaxalone (µM) | Nirvanol formation | | | Specific Activity | | Percent of VC |
|---|---|---|---|---|---|---|
| | Raw (µM) | Adjusted (µM) | | (pmol/min/mg protein) | | |
| | | Individual | Mean ± SD | Individual | Mean ± SD | |
| 0 (VC) | 0.23500 | 0.235 | 0.225 ± 0.0120 | 31.3 | 29.9 ± 1.60 | 100 |
| | 0.23266 | 0.233 | | 31.0 | | |
| | 0.22199 | 0.222 | | 29.6 | | |
| | 0.20877 | 0.209 | | 27.8 | | |
| 0.3 | 0.20942 | 0.209 | 0.203 ± 0.00904 | 27.9 | 27.0 ± 1.21 | 90.2 |
| | 0.19234 | 0.192 | | 25.6 | | |
| | 0.20601 | 0.206 | | 27.5 | | |
| 1 | 0.20438 | 0.204 | 0.223 ± 0.0201 | 27.3 | 29.8 ± 2.68 | 99.5 |
| | 0.22144 | 0.221 | | 29.5 | | |
| | 0.24442 | 0.244 | | 32.6 | | |

TABLE 11-continued

CYP2B6 Activity in Pooled Human Microsomes

| Metaxalone (μM) | Raw (μM) | Nirvanol formation Adjusted (μM) | | Specific Activity (pmol/min/mg protein) | | Percent of VC |
|---|---|---|---|---|---|---|
| | | Individual | Mean ± SD | Individual | Mean ± SD | |
| 3 | 0.19695 | 0.197 | 0.203 ± 0.00751 | 26.3 | 27.1 ± 1.00 | 90.6 |
| | 0.20166 | 0.202 | | 26.9 | | |
| | 0.21166 | 0.212 | | 28.2 | | |
| 30 | 0.21681 | 0.217 | 0.217 ± 0.00162 | 28.9 | 28.9 ± 0.216 | 96.6 |
| | 0.21548 | 0.215 | | 28.7 | | |
| | 0.21871 | 0.219 | | 29.2 | | |
| 100 | 0.18648 | 0.186 | 0.188 ± 0.00436 | 24.9 | 25.1 ± 0.581 | 83.7 |
| | 0.18463 | 0.185 | | 24.6 | | |
| | 0.19293 | 0.193 | | 25.7 | | |

Abbreviations:
SD, standard deviation;
VC, vehicle control (1% Methanol)
Note:
For all calculations above, the resulting values are shown with at least three significant figures for display purposes only.

TABLE 12

CYP2C8 Activity in Pooled Human Microsomes

| Metaxalone (μM) | Raw (μM) | 6-Hydroxypaclitaxel formation Adjusted (μM) | | Specific Activity (pmol/min/mg protein) | | Percent of VC |
|---|---|---|---|---|---|---|
| | | Individual | Mean ± SD | Individual | Mean ± SD | |
| 0 (VC) | 0.13462 | 0.135 | 0.136 ± 0.00522 | 17.9 | 18.2 ± 0.696 | 100 |
| | 0.14017 | 0.140 | | 18.7 | | |
| | 0.14074 | 0.141 | | 18.8 | | |
| | 0.12965 | 0.130 | | 17.3 | | |
| 0.3 | 0.14476 | 0.145 | 0.126 ± 0.0163 | 19.3 | 16.8 ± 2.18 | 92.7 |
| | 0.11377 | 0.114 | | 15.2 | | |
| | 0.12042 | 0.120 | | 16.1 | | |
| 1 | 0.13927 | 0.139 | 0.140 ± 0.00305 | 18.6 | 18.7 ± 0.406 | 103 |
| | 0.13749 | 0.137 | | 18.3 | | |
| | 0.14343 | 0.143 | | 19.1 | | |
| 3 | 0.15034 | 0.150 | 0.149 ± 0.00174 | 20.0 | 19.9 ± 0.232 | 109 |
| | 0.14945 | 0.149 | | 19.9 | | |
| | 0.14698 | 0.147 | | 19.6 | | |
| 30 | 0.14949 | 0.149 | 0.138 ± 0.0114 | 19.9 | 18.4 ± 1.52 | 101 |
| | 0.13724 | 0.137 | | 18.3 | | |
| | 0.12667 | 0.127 | | 16.9 | | |
| 100 | 0.13170 | 0.132 | 0.133 ± 0.0207 | 17.6 | 17.8 ± 2.76 | 97.8 |
| | 0.15467 | 0.155 | | 20.6 | | |
| | 0.11340 | 0.113 | | 15.1 | | |

Abbreviations:
SD, standard deviation;
VC, vehicle control (1% Methanol)
Note:
For all calculations above, the resulting values are shown with at least three significant figures for display purposes only.

TABLE 13

CYP2C9 Activity in Pooled Human Microsomes

| Metaxalone (μM) | 4'-Methylhydroxytolbutamide formation | | | Specific Activity | | Percent of VC |
|---|---|---|---|---|---|---|
| | Raw (μM) | Adjusted (μM) | | (pmol/min/mg protein) | | |
| | | Individual | Mean ± SD | Individual | Mean ± SD | |
| 0 (VC) | 0.17476 | 0.175 | 0.166 ± 0.0208 | 46.6 | 44.3 ± 5.54 | 100 |
| | 0.14904 | 0.149 | | 39.7 | | |
| | 0.14954 | 0.150 | | 39.9 | | |
| | 0.19164 | 0.192 | | 51.1 | | |
| 0.3 | 0.13620 | 0.136 | 0.135 ± 0.00106 | 36.3 | 36.1 ± 0.283 | 81.4 |
| | 0.13415 | 0.134 | | 35.8 | | |
| | 0.13565 | 0.136 | | 36.2 | | |
| 1 | 0.15107 | 0.151 | 0.136 ± 0.0187 | 40.3 | 36.2 ± 4.98 | 81.6 |
| | 0.14080 | 0.141 | | 37.5 | | |
| | 0.11485 | 0.115 | | 30.6 | | |
| 3 | 0.13051 | 0.131 | 0.135 ± 0.0103 | 34.8 | 36.0 ± 2.75 | 81.2 |
| | 0.12759 | 0.128 | | 34.0 | | |
| | 0.14670 | 0.147 | | 39.1 | | |
| 30 | 0.14975 | 0.150 | 0.151 ± 0.00841 | 39.9 | 40.3 ± 2.24 | 91.0 |
| | 0.14376 | 0.144 | | 38.3 | | |
| | 0.16037 | 0.160 | | 42.8 | | |
| 100 | 0.16269 | 0.163 | 0.145 ± 0.0150 | 43.4 | 38.8 ± 4.00 | 87.4 |
| | 0.13711 | 0.137 | | 36.6 | | |
| | 0.13627 | 0.136 | | 36.3 | | |

Abbreviations:
SD, standard deviation;
VC, vehicle control (1% Methanol)
Note:
For all calculations above, the resulting values are shown with at least three significant figures for display purposes only.

TABLE 14

CYP2C19 Activity in Pooled Human Microsomes

| Metaxalone (μM) | 4'-Hydroxymephenytoin formation | | | Specific Activity | | Percent of VC |
|---|---|---|---|---|---|---|
| | Raw (μM) | Adjusted (μM) | | (pmol/min/mg protein) | | |
| | | Individual | Mean ± SD | Individual | Mean ± SD | |
| 0 (VC) | 0.16904 | 0.169 | 0.168 ± 0.00550 | 22.5 | 22.4 ± 0.733 | 100 |
| | 0.17373 | 0.174 | | 23.2 | | |
| | 0.16915 | 0.169 | | 22.6 | | |
| | 0.16055 | 0.161 | | 21.4 | | |
| 0.3 | 0.13971 | 0.140 | 0.142 ± 0.00299 | 18.6 | 19.0 ± 0.399 | 84.6 |
| | 0.14558 | 0.146 | | 19.4 | | |
| | 0.14164 | 0.142 | | 18.9 | | |
| 1 | 0.11367 | 0.114 | 0.113 ± 0.00140 | 15.2 | 15.0 ± 0.186 | 67.0 |
| | 0.11336 | 0.113 | | 15.1 | | |
| | 0.11111 | 0.111 | | 14.8 | | |
| 3 | 0.11597 | 0.116 | 0.114 ± 0.00238 | 15.5 | 15.2 ± 0.317 | 67.7 |
| | 0.11127 | 0.111 | | 14.8 | | |
| | 0.11423 | 0.114 | | 15.2 | | |
| 30 | 0.08336 | 0.0834 | 0.107 ± 0.0211 | 11.1 | 14.3 ± 2.82 | 63.8 |
| | 0.12339 | 0.123 | | 16.5 | | |
| | 0.11502 | 0.115 | | 15.3 | | |
| 100 | 0.10857 | 0.109 | 0.109 ± 0.00205 | 14.5 | 14.5 ± 0.274 | 64.9 |
| | 0.11132 | 0.111 | | 14.8 | | |
| | 0.10730 | 0.107 | | 14.3 | | |

Abbreviations:
SD, standard deviation;
VC, vehicle control (1% Methanol)
Note:
For all calculations above, the resulting values are shown with at least three significant figures for display purposes only.

TABLE 15

CYP2D6 Activity in Pooled Human Microsomes

| Metaxalone (μM) | Raw (μM) | Dextrorphan formation Adjusted (μM) | | Specific Activity (pmol/min/mg protein) | | Percent of VC |
|---|---|---|---|---|---|---|
| | | Individual | Mean ± SD | Individual | Mean ± SD | |
| 0 (VC) | 0.18550 | 0.186 | 0.183 ± 0.00342 | 49.5 | 48.9 ± 0.911 | 100 |
| | 0.18569 | 0.186 | | 49.5 | | |
| | 0.18424 | 0.184 | | 49.1 | | |
| | 0.17843 | 0.178 | | 47.6 | | |
| 0.3 | 0.14820 | 0.148 | 0.149 ± 0.00258 | 39.5 | 39.8 ± 0.688 | 81.3 |
| | 0.14716 | 0.147 | | 39.2 | | |
| | 0.15206 | 0.152 | | 40.5 | | |
| 1 | 0.15910 | 0.159 | 0.154 ± 0.00482 | 42.4 | 41.2 ± 1.28 | 84.2 |
| | 0.14949 | 0.149 | | 39.9 | | |
| | 0.15485 | 0.155 | | 41.3 | | |
| 3 | 0.16116 | 0.161 | 0.164 ± 0.00353 | 43.0 | 43.7 ± 0.940 | 89.3 |
| | 0.16267 | 0.163 | | 43.4 | | |
| | 0.16788 | 0.168 | | 44.8 | | |
| 30 | 0.15533 | 0.155 | 0.156 ± 0.00335 | 41.4 | 41.6 ± 0.893 | 85.1 |
| | 0.15983 | 0.160 | | 42.6 | | |
| | 0.15328 | 0.153 | | 40.9 | | |
| 100 | 0.15992 | 0.160 | 0.158 ± 0.00255 | 42.6 | 42.0 ± 0.680 | 85.9 |
| | 0.15489 | 0.155 | | 41.3 | | |
| | 0.15813 | 0.158 | | 42.2 | | |

Abbreviations:
SD, standard deviation;
VC, vehicle control (1% Methanol)
Note:
For all calculations above, the resulting values are shown with at least three significant figures for display purposes only.

TABLE 16

CYP2E1 Activity in Pooled Human Microsomes

| Metaxalone (μM) | Raw (μM) | 6-Hydroxychlorzoxazone formation Adjusted (μM) | | Specific Activity (pmol/min/mg protein) | | Percent of VC |
|---|---|---|---|---|---|---|
| | | Individual | Mean ± SD | Individual | Mean ± SD | |
| 0 (VC) | 0.85346 | 0.853 | 0.852 ± 0.0127 | 228 | 227 ± 3.39 | 100 |
| | 0.86925 | 0.869 | | 232 | | |
| | 0.84615 | 0.846 | | 226 | | |
| | 0.83969 | 0.840 | | 224 | | |
| 0.3 | 0.73634 | 0.736 | 0.710 ± 0.0228 | 196 | 189 ± 6.08 | 83.3 |
| | 0.69947 | 0.699 | | 187 | | |
| | 0.69469 | 0.695 | | 185 | | |
| 1 | 0.72701 | 0.727 | 0.716 ± 0.0194 | 194 | 191 ± 5.18 | 84.0 |
| | 0.72685 | 0.727 | | 194 | | |
| | 0.69326 | 0.693 | | 185 | | |
| 3 | 0.76089 | 0.761 | 0.755 ± 0.0110 | 203 | 201 ± 2.94 | 88.6 |
| | 0.74221 | 0.742 | | 198 | | |
| | 0.76169 | 0.762 | | 203 | | |
| 30 | 0.71716 | 0.717 | 0.733 ± 0.0145 | 191 | 196 ± 3.88 | 86.1 |
| | 0.74538 | 0.745 | | 199 | | |
| | 0.73733 | 0.737 | | 197 | | |
| 100 | 0.74969 | 0.750 | 0.743 ± 0.0175 | 200 | 198 ± 4.66 | 87.2 |
| | 0.75620 | 0.756 | | 202 | | |
| | 0.72321 | 0.723 | | 193 | | |

Abbreviations:
SD, standard deviation;
VC, vehicle control (1% Methanol)
Note:
For all calculations above, the resulting values are shown with at least three significant figures for display purposes only.

TABLE 17

CYP3A4 Activity in Pooled Human Microsomes

| Metaxalone | 6β-Hydroxytestosterone formation | | | Specific Activity | | Percent |
|---|---|---|---|---|---|---|
| | Raw | Adjusted (μM) | | (pmol/min/mg protein) | | |
| (μM) | (μM) | Individual | Mean ± SD | Individual | Mean ± SD | of VC |
| 0 (VC) | 0.12662* | N/A | 0.742 ± 0.00679 | N/A | 594 ± 5.43 | 100 |
| | 0.74589 | 0.746 | | 597 | | |
| | 0.74640 | 0.746 | | 597 | | |
| | 0.73440 | 0.734 | | 588 | | |
| 0.3 | 0.64318 | 0.643 | 0.647 ± 0.0130 | 515 | 517 ± 10.4 | 87.1 |
| | 0.66083 | 0.661 | | 529 | | |
| | 0.63550 | 0.636 | | 508 | | |
| 1 | 0.65762 | 0.658 | 0.654 ± 0.00353 | 526 | 523 ± 2.83 | 88.1 |
| | 0.65446 | 0.654 | | 524 | | |
| | 0.65057 | 0.651 | | 520 | | |
| 3 | 0.67154 | 0.672 | 0.668 ± 0.00420 | 537 | 534 ± 3.36 | 90.0 |
| | 0.66336 | 0.663 | | 531 | | |
| | 0.66907 | 0.669 | | 535 | | |
| 30 | 0.62513 | 0.625 | 0.633 ± 0.0370 | 500 | 506 ± 29.6 | 85.2 |
| | 0.67282 | 0.673 | | 538 | | |
| | 0.59996 | 0.600 | | 480 | | |
| 100 | 0.63960 | 0.640 | 0.596 ± 0.0454 | 512 | 477 ± 36.3 | 80.3 |
| | 0.59940 | 0.599 | | 480 | | |
| | 0.54904 | 0.549 | | 439 | | |

Abbreviations:
SD, standard deviation;
VC, vehicle control (1% Methanol)
*Sample has been removed from all calculations due to the incorrect volume being added to the sample to stop the reaction.
Note:
For all calculations above, the resulting values are shown with at least three significant figures for display purposes only.

Under these experimental conditions, metaxalone inhibited activities of CYP1A2, CYP2B6, CYP2C19, CYP2D6, CYP2E1, and CYP3A4 in human liver microsomes at one or more of the tested metaxalone concentrations at a statistically significant level ($p \leq 0.05$ using an unpaired two-tailed t-test). The inhibition ranged from 12.8% (CYP2E1) to 35.1% (CYP2C19) at a metaxalone concentration of 100 μM.

Under these experimental conditions, no tested concentration of metaxalone inhibited activity of CYP2A6, CYP2C8, or CYP2C9 in human liver microsomes at a statistically significant level ($p > 0.05$ using an unpaired two-tailed t-test).

Example 3

Metaxalone Induction/Inhibition of Cytochrome p450 Isozymes

The study of this example was performed to determine if there is induction or inhibition by metaxalone of cytochrome p450 isozymes CYP1A2, CYP2A6, CYP2B6, CYP2C9, CYP2C19, CYP2D6, CYP2E1, and CYP3A4. These induction/inhibition studies used cryopreserved human hepatocytes and compared enzymatic activity levels for each of these cytochrome p450 isozymes, using an appropriate enzyme substrate, in the human hepatocytes following in vitro exposure for 48±3 hrs in the presence or absence of metaxalone.

Hepatocytes from three human donors were obtained from a cryopreserved hepatocyte bank (In Vitro Technologies, Inc., USA). After thawing, viable hepatocytes were transferred to collagen-coated 48-well plates for attachment in plating medium (DMEM stock (Dulbecco's modified Eagle's medium, supplemented with bovine serum albumin, fructose, N-(2-hydroxyethyl)piperazine-N'-(2-ethanesulfonate) (HEPES), and sodium bicarbonate), supplemented with antibiotics, bovine serum, hydrocortisone, insulin and minimum essential medium (MEM) nonessential amino acids). After attachment to the collagen matrix, plating medium was replaced with sandwich medium (plating medium supplemented with VITROGEN) and incubated until use. All incubations were conducted at 37±1° C., 95% air/5% $CO_2$ and saturating humidity.

After establishment of the hepatocyte culture, sandwich medium was removed and the hepatocytes were incubated with incubation solution (DMEM stock supplemented with antibiotics, hydrocortisone, insulin, and MEM non-essential amino acids) containing 0.4, 4.0, or 40 μM metaxalone for 24±1.5 hrs. Incubation solution was aspirated and replaced with incubation solution containing the same concentration of metaxalone and incubated for an additional 24±1.5 hrs. After the metaxalone treatment period, the incubation solution was replaced with 150 μL Krebs-Henseleit (KHB) buffer supplemented with antibiotics, calcium chloride, heptanoic acid, HEPES, and sodium bicarbonate (supplemented KHB) and incubated for 10 minutes. The supplemented KHB was replaced with 150 μL supplemented KHB containing the appropriate isoform-selective substrate and incubated for 4 hrs prior to termination by adding 150 μL ice-cold methanol, except for the CYP2C8 incubations which were terminated by adding 150 μL acetonitrile. Samples were transferred to cryovials and analyzed after storage at −70° C. Three induction replicates were performed at each metaxalone concentration for each cytochrome p450 isozyme.

A table of the substrate, substrate concentration, metabolite formed, and metabolite assay method for each CYP isozyme studied is provided below. All substrates were dissolved in acetonitrile.

| CYP isoform | Isoform-selective substrate | Substrate concentration | Metabolite formed | Metabolite Assay |
|---|---|---|---|---|
| CYP1A2 | Phenacetin | 100 μM | acetaminophen | LC/MS |
| CYP2A6 | Coumarin | 100 μM | 7-hydroxycoumarin, 7-hydroxycoumarin-glucuronide, 7-hydroxycoumarin sulfate | HPLC-UV |
| CYP2B6 | S-Mephenytoin | 1 mM | nirvanol | LC/MS |
| CYP2C9 | Tolbutamide | 50 μM | 4'-methylhydroxytolbutamide | LC/MS |
| CYP2C19 | S-Mephenytoin | 100 μM | 4'-hydroxy mephenytoin | LC/MS |
| CYP2D6 | Dextromethorphan | 16 μM | dextrorphan | LC/MS |
| CYP2E1 | Chlorzoxazone | 300 μM | 6-hydroxychlorzoxazone | LC/MS |
| CYP3A4 | Testosterone | 125 μM | 6β-hydroxy testosterone | HPLC-UV |

Metaxalone 100× stock solutions were prepared in methanol as described above and diluted with incubation medium to produce incubation solutions with 0.4, 4.0, and 40 μM metaxalone.

Replicate trials and controls were performed. Positive controls (n=4) were performed to verify that the test system was sensitive to known inducers by testing induction of CYP1A2 and CYP3A4 using 50 μM omeprazole and 25 μM rifampicin, respectively, as inducers with the appropriate isoform-selective substrate. Both positive control test systems showed ≧200% induction. Additionally, reference control samples were included to evaluate inducibility of CYP2B6, CYP2C9, and CYP2C19 in the test system. The reference controls included 1 mM Phenobarbital (CYP2B6) or 25 μM rifampicin as the reference inducer. The reference controls showed a statistically significant amount of induction for each hepatocyte donor for CYP2B6 and CYP2C9, although the amount of induction varied between the three hepatocyte donors for each isozyme. For CYP2C19, rifampin induced CYP2C19 activity in donor 1 and donor 3, but did not induce CYP2C19 activity in donor 2 at a statistically significant level (p<0.05 using an unpaired two-tailed t-test).

Results for each cytochrome p450 isozyme are shown in Tables 18-25. Significant induction was observed at these experimental conditions in all three donors for CYP1A2 and in one donor for CYP3A4 at the highest tested concentration. Additionally, significant inhibition in enzyme activity was observed in all three donors for CYP2C9 and in two donors for CYP2D6. Under these experimental conditions, no significant effects on activity of CYP2A6, CYP2B6, CYP2C19, or CYP2E1 were observed after exposure to any of the tested concentrations of metaxalone. Significance of a change in specific activity from that measured for the vehicle control (0 μM metaxalone) was determined using a two-tailed t-test. Mean specific activity values with associated p-values≦0.05 were deemed to be statistically significant.

TABLE 18

CYP1A2 Activity in Cryopreserved Human Hepatocytes

| Metaxalone (μM) | Acetaminophen formation | | | Specific Activity | | Percent of VC |
|---|---|---|---|---|---|---|
| | Raw (μM) | Adjusted (μM) | | (pmol/min/million cells) | | |
| | | Individual | Mean ± SD | Individual | Mean ± SD | |
| Donor 1 | | | | | | |
| 0 (VC) | 0.05388 | 0.0539 | 0.0487 ± 0.00543 | 0.481 | 0.435 ± 0.0485 | 100 |
| | 0.05227 | 0.0523 | | 0.467 | | |
| | 0.04658 | 0.0466 | | 0.416 | | |
| | 0.04203 | 0.0420 | | 0.375 | | |
| 0.4 | 0.05121 | 0.0512 | 0.0537 ± 0.00309 | 0.457 | 0.479 ± 0.0276 | 110 |
| | 0.05264 | 0.0526 | | 0.470 | | |
| | 0.05714 | 0.0571 | | 0.510 | | |
| 4 | 0.07410 | 0.0741 | 0.0638 ± 0.0193 | 0.662 | 0.570 ± 0.172 | 131 |
| | 0.07581 | 0.0758 | | 0.677 | | |
| | 0.04160 | 0.0416 | | 0.371 | | |
| 40 | 0.15156 | 0.152 | 0.161 ± 0.0133 | 1.35 | 1.44 ± 0.119 | 332 |
| | 0.15617 | 0.156 | | 1.39 | | |
| | 0.17659 | 0.177 | | 1.58 | | |
| Donor 2 | | | | | | |
| 0 (VC) | 0.03023 | 0.0302 | 0.0300 ± 0.00305 | 0.270 | 0.267 ± 0.0272 | 100 |
| | 0.03210 | 0.0321 | | 0.287 | | |
| | 0.03193 | 0.0319 | | 0.285 | | |
| | 0.02556 | 0.0256 | | 0.228 | | |
| 0.4 | 0.03165 | 0.0317 | 0.0323 ± 0.000850 | 0.283 | 0.289 ± 0.00759 | 108 |
| | 0.03208 | 0.0321 | | 0.286 | | |
| | 0.03329 | 0.0333 | | 0.297 | | |
| 4 | 0.03346 | 0.0335 | 0.0340 ± 0.00198 | 0.299 | 0.304 ± 0.0177 | 113 |
| | 0.03619 | 0.0362 | | 0.323 | | |
| | 0.03234 | 0.0323 | | 0.289 | | |

TABLE 18-continued

CYP1A2 Activity in Cryopreserved Human Hepatocytes

| Metaxalone (μM) | Acetaminophen formation | | | Specific Activity | | Percent of VC |
|---|---|---|---|---|---|---|
| | Raw (μM) | Adjusted (μM) | | (pmol/min/million cells) | | |
| | | Individual | Mean ± SD | Individual | Mean ± SD | |
| 40 | 0.06015 | 0.0602 | 0.0589 ± 0.00795 | 0.537 | 0.526 ± 0.0710 | 197 |
|    | 0.06616 | 0.0662 |                  | 0.591 |                 |     |
|    | 0.05040 | 0.0504 |                  | 0.450 |                 |     |
| Donor 3 | | | | | | |
| 0 (VC) | 0.04357 | 0.0436 | 0.0410 ± 0.00447 | 0.389 | 0.366 ± 0.0399 | 100 |
|        | 0.04576 | 0.0458 |                  | 0.409 |                |     |
|        | 0.03607 | 0.0361 |                  | 0.322 |                |     |
|        | 0.03849 | 0.0385 |                  | 0.344 |                |     |
| 0.4 | 0.04030 | 0.0403 | 0.0438 ± 0.00361 | 0.360 | 0.391 ± 0.0322 | 107 |
|     | 0.04347 | 0.0435 |                  | 0.388 |                |     |
|     | 0.04750 | 0.0475 |                  | 0.424 |                |     |
| 4   | 0.04411 | 0.0441 | 0.0443 ± 0.000214 | 0.394 | 0.396 ± 0.00191 | 108 |
|     | 0.04453 | 0.0445 |                   | 0.398 |                 |     |
|     | 0.04425 | 0.0443 |                   | 0.395 |                 |     |
| 40  | 0.12276 | 0.123  | 0.122 ± 0.00365  | 1.10 | 1.09 ± 0.0326 | 297 |
|     | 0.11776 | 0.118  |                  | 1.05 |               |     |
|     | 0.12487 | 0.125  |                  | 1.11 |               |     |

Abbreviations:
SD, standard deviation;
VC, vehicle control (1% Methanol)
Note:
For all calculations above, the resulting values are shown with at least three significant figures for display purposes only.

TABLE 19

CYP2A6 Activity in Cryopreserved Human Hepatocytes

| Metaxalone (μM) | Total Metabolite formation | | | Specific Activity | | Percent of VC |
|---|---|---|---|---|---|---|
| | Raw (μM) | Adjusted (μM) | | (pmol/min/million cells) | | |
| | | Individual | Mean ± SD | Individual | Mean ± SD | |
| Total Metabolite Formation: Donor 1 | | | | | | |
| 0 (VC) | 0.0171[d] | <0.300 | <0.300 ± 0.000 | <2.68 | <2.68 ± 0.000 | 100 |
|        | 0.000[d]  | <0.300 |                | <2.68 |               |     |
|        | 0.000[d]  | <0.300 |                | <2.68 |               |     |
|        | 0.000[d]  | <0.300 |                | <2.68 |               |     |
| 0.4 | 0.000[d] | <0.300 | <0.300 ± 0.000 | <2.68 | <2.68 ± 0.000 | 100 |
|     | 0.000[d] | <0.300 |                | <2.68 |               |     |
|     | 0.000[d] | <0.300 |                | <2.68 |               |     |
| 4   | 0.000[d] | <0.300 | <0.300 ± 0.000 | <2.68 | <2.68 ± 0.000 | 100 |
|     | 0.000[d] | <0.300 |                | <2.68 |               |     |
|     | 0.000[d] | <0.300 |                | <2.68 |               |     |
| 40  | 0.000[d] | <0.300 | <0.300 ± 0.000 | <2.68 | <2.68 ± 0.000 | 100 |
|     | 0.000[d] | <0.300 |                | <2.68 |               |     |
|     | 0.000[d] | <0.300 |                | <2.68 |               |     |
| Total Metabolite Formation: Donor 2 | | | | | | |
| 0 (VC) | 0.0381[d] | <0.300 | <0.300 ± 0.000 | <2.68 | <2.68 ± 0.000 | 100 |
|        | 0.0413[d] | <0.300 |                | <2.68 |               |     |
|        | 0.0365[d] | <0.300 |                | <2.68 |               |     |
|        | 0.0320[d] | <0.300 |                | <2.68 |               |     |
| 0.4 | 0.0225[d] | <0.300 | <0.300 ± 0.000 | <2.68 | <2.68 ± 0.000 | 100 |
|     | 0.0381[d] | <0.300 |                | <2.68 |               |     |
|     | 0.0381[d] | <0.300 |                | <2.68 |               |     |
| 4   | 0.0344[d] | <0.300 | <0.300 ± 0.000 | <2.68 | <2.68 ± 0.000 | 100 |
|     | 0.0353[d] | <0.300 |                | <2.68 |               |     |
|     | 0.0297[d] | <0.300 |                | <2.68 |               |     |
| 40  | 0.0293[d] | <0.300 | <0.300 ± 0.000 | <2.68 | <2.68 ± 0.000 | 100 |
|     | 0.0266[d] | <0.300 |                | <2.68 |               |     |
|     | 0.0333[d] | <0.300 |                | <2.68 |               |     |

TABLE 19-continued

CYP2A6 Activity in Cryopreserved Human Hepatocytes

| Metaxalone (µM) | Raw (µM) | Total Metabolite formation Adjusted (µM) | | Specific Activity (pmol/min/million cells) | | Percent of VC |
|---|---|---|---|---|---|---|
| | | Individual | Mean ± SD | Individual | Mean ± SD | |
| Total Metabolite Formation: Donor 3 | | | | | | |
| 0 (VC) | $0.000^d$ | <0.300 | <0.300 ± 0.000 | <2.68 | <2.68 ± 0.000 | 100 |
| | $0.0196^d$ | <0.300 | | <2.68 | | |
| | $0.0237^d$ | <0.300 | | <2.68 | | |
| 0.4 | $0.000^d$ | <0.300 | <0.300 ± 0.000 | <2.68 | <2.68 ± 0.000 | 100 |
| | $0.0216^d$ | <0.300 | | <2.68 | | |
| | $0.0182^d$ | <0.300 | | <2.68 | | |
| | $0.0182^d$ | <0.300 | | <2.68 | | |
| 4 | $0.000^d$ | <0.300 | <0.300 ± 0.000 | <2.68 | <2.68 ± 0.000 | 100 |
| | $0.0197^d$ | <0.300 | | <2.68 | | |
| | $0.0162^d$ | <0.300 | | <2.68 | | |
| 40 | $0.000^d$ | <0.300 | <0.300 ± 0.000 | <2.68 | <2.68 ± 0.000 | 100 |
| | $0.0188^d$ | <0.300 | | <2.68 | | |
| | $0.000^d$ | <0.300 | | <2.68 | | |

Abbreviations:
SD, standard deviation;
VC, vehicle control (1% Methanol)

$^d$The observed analyzed value (µM) for all metabolites were below the lowest concentration on the corresponding standard curve.

Note:
For all calculations above, the resulting values are shown with at least three significant figures for display purposes only.

TABLE 20

CYP2B6 Activity in Cryopreserved Human Hepatocytes

| Metaxalone (µM) | Raw (µM) | Nirvanol formation Adjusted (µM) | | Specific Activity (pmol/min/million cells) | | Percent of VC |
|---|---|---|---|---|---|---|
| | | Individual | Mean ± SD | Individual | Mean ± SD | |
| Donor 1 | | | | | | |
| 0 (VC) | 0.03230 | 0.0323 | 0.0319 ± 0.00156 | 0.288 | 0.285 ± 0.0139 | 100 |
| | 0.03384 | 0.0338 | | 0.302 | | |
| | 0.03014 | 0.0301 | | 0.269 | | |
| | 0.03141 | 0.0314 | | 0.280 | | |
| 0.4 | 0.03380 | 0.0338 | 0.0340 ± 0.000883 | 0.302 | 0.304 ± 0.00789 | 107 |
| | 0.03329 | 0.0333 | | 0.297 | | |
| | 0.03501 | 0.0350 | | 0.313 | | |
| 4 | 0.02742 | 0.0274 | 0.0305 ± 0.00272 | 0.245 | 0.273 ± 0.0243 | 95.7 |
| | 0.03241 | 0.0324 | | 0.289 | | |
| | 0.03178 | 0.0318 | | 0.284 | | |
| 40 | 0.03233 | 0.0323 | 0.0310 ± 0.00204 | 0.289 | 0.277 ± 0.0182 | 97.1 |
| | 0.03203 | 0.0320 | | 0.286 | | |
| | 0.02866 | 0.0287 | | 0.256 | | |
| Donor 2 | | | | | | |
| 0 (VC) | 0.02927 | 0.0293 | 0.0289 ± 0.00230 | 0.261 | 0.258 ± 0.0205 | 100 |
| | 0.02920 | 0.0292 | | 0.261 | | |
| | 0.03137 | 0.0314 | | 0.280 | | |
| | 0.02582 | 0.0258 | | 0.231 | | |
| 0.4 | 0.02544 | 0.0254 | 0.0306 ± 0.00559 | 0.227 | 0.273 ± 0.0499 | 106 |
| | 0.02986 | 0.0299 | | 0.267 | | |
| | 0.03654 | 0.0365 | | 0.326 | | |
| 4 | 0.02852 | 0.0285 | 0.0281 ± 0.000884 | 0.255 | 0.250 ± 0.00790 | 97.0 |
| | 0.02703 | 0.0270 | | 0.241 | | |
| | 0.02860 | 0.0286 | | 0.255 | | |
| 40 | $0.00341^a$ | <0.0250 | <0.0250 ± 0.000 | <0.223 | <0.223 ± 0.000 | <86.5 |
| | $0.00320^a$ | <0.0250 | | <0.223 | | |
| | $0.00330^a$ | <0.0250 | | <0.223 | | |

TABLE 20-continued

CYP2B6 Activity in Cryopreserved Human Hepatocytes

| Metaxalone (μM) | Raw (μM) | Nirvanol formation Adjusted (μM) Individual | Mean ± SD | Specific Activity (pmol/min/million cells) Individual | Mean ± SD | Percent of VC |
|---|---|---|---|---|---|---|
| | | Donor 3 | | | | |
| 0 (VC) | 0.02349[a] | <0.0250 | <0.0252 ± 0.000435 | <0.223 | <0.225 ± 0.00388 | 100 |
| | 0.02587 | 0.0259 | | 0.231 | | |
| | 0.02376[a] | <0.0250 | | <0.223 | | |
| | 0.02236[a] | <0.0250 | | <0.223 | | |
| 0.4 | 0.02177[a] | <0.0250 | <0.0250 ± 0.000 | <0.223 | <0.223 ± 0.000 | 99.1 |
| | 0.02343[a] | <0.0250 | | <0.223 | | |
| | 0.02326[a] | <0.0250 | | <0.223 | | |
| 4 | 0.02392[a] | <0.0250 | <0.0250 ± 0.000 | <0.223 | <0.223 ± 0.000 | 99.1 |
| | 0.02490[a] | <0.0250 | | <0.223 | | |
| | 0.02229[a] | <0.0250 | | <0.223 | | |
| 40 | 0.02005[a] | <0.0250 | <0.0250 ± 0.000 | <0.223 | <0.223 ± 0.000 | 99.1 |
| | 0.01976[a] | <0.0250 | | <0.223 | | |
| | 0.02169[a] | <0.0250 | | <0.223 | | |

Abbreviations:
SD, standard deviation;
VC, vehicle control (1% Methanol)
[a]The observed analyzed value (μM) was below the lowest concentration on the standard curve (0.025 μM).
Note:
For all calculations above, the resulting values are shown with at least three significant figures for display purposes only.

TABLE 21

CYP2C9 Activity in Cryopreserved Human Hepatocytes

| Metaxalone (μM) | Raw (μM) | 4'-Methylhydroxytolbutamide formation Adjusted (μM) Individual | Mean ± SD | Specific Activity (pmol/min/million cells) Individual | Mean ± SD | Percent of VC |
|---|---|---|---|---|---|---|
| | | Donor 1 | | | | |
| 0 (VC) | 0.01215 | 0.0122 | 0.0137 ± 0.00161 | 0.108 | 0.122 ± 0.0144 | 100 |
| | 0.01502 | 0.0150 | | 0.134 | | |
| | 0.01513 | 0.0151 | | 0.135 | | |
| | 0.01245 | 0.0125 | | 0.111 | | |
| 0.4 | 0.01557 | 0.0156 | 0.0147 ± 0.000753 | 0.139 | 0.132 ± 0.00672 | 108 |
| | 0.01410 | 0.0141 | | 0.126 | | |
| | 0.01455 | 0.0146 | | 0.130 | | |
| 4 | 0.01331 | 0.0133 | 0.0137 ± 0.00136 | 0.119 | 0.122 ± 0.0121 | 100 |
| | 0.01523 | 0.0152 | | 0.136 | | |
| | 0.01261 | 0.0126 | | 0.113 | | |
| 40 | 0.00931[a] | <0.0100 | <0.0100 ± 0.0000346 | <0.0893 | <0.0895 ± 0.000309 | <73.2 |
| | 0.00952[a] | <0.0100 | | <0.0893 | | |
| | 0.01006 | 0.0101 | | 0.0898 | | |
| | | Donor 2 | | | | |
| 0 (VC) | 0.05192 | 0.0519 | 0.0491 ± 0.00479 | 0.464 | 0.438 ± 0.0428 | 100 |
| | 0.04864 | 0.0486 | | 0.434 | | |
| | 0.05325 | 0.0533 | | 0.475 | | |
| | 0.04250 | 0.0425 | | 0.379 | | |
| 0.4 | 0.04819 | 0.0482 | 0.0474 ± 0.00223 | 0.430 | 0.423 ± 0.0200 | 96.6 |
| | 0.04489 | 0.0449 | | 0.401 | | |
| | 0.04915 | 0.0492 | | 0.439 | | |
| 4 | 0.04634 | 0.0463 | 0.0456 ± 0.000864 | 0.414 | 0.407 ± 0.00772 | 92.9 |
| | 0.04581 | 0.0458 | | 0.409 | | |
| | 0.04465 | 0.0447 | | 0.399 | | |
| 40 | 0.02917 | 0.0292 | 0.0296 ± 0.000651 | 0.260 | 0.265 ± 0.00581 | 60.4 |
| | 0.02936 | 0.0294 | | 0.262 | | |
| | 0.03038 | 0.0304 | | 0.271 | | |

TABLE 21-continued

CYP2C9 Activity in Cryopreserved Human Hepatocytes

| Metaxalone (µM) | Raw (µM) | 4'-Methylhydroxytolbutamide formation | | Specific Activity (pmol/min/million cells) | | Percent of VC |
|---|---|---|---|---|---|---|
| | | Adjusted (µM) | | | | |
| | | Individual | Mean ± SD | Individual | Mean ± SD | |
| Donor 3 | | | | | | |
| 0 | 0.02021 | 0.0202 | 0.0181 ± 0.00206 | 0.180 | 0.162 ± 0.0184 | 100 |
| (VC) | 0.01700 | 0.0170 | | 0.152 | | |
| | 0.01952 | 0.0195 | | 0.174 | | |
| | 0.01586 | 0.0159 | | 0.142 | | |
| 0.4 | 0.02067 | 0.0207 | 0.0201 ± 0.00125 | 0.185 | 0.179 ± 0.0111 | 111 |
| | 0.02096 | 0.0210 | | 0.187 | | |
| | 0.01867 | 0.0187 | | 0.167 | | |
| 4 | 0.01807 | 0.0181 | 0.0187 ± 0.00235 | 0.161 | 0.167 ± 0.0210 | 103 |
| | 0.02129 | 0.0213 | | 0.190 | | |
| | 0.01671 | 0.0167 | | 0.149 | | |
| 40 | 0.01364 | 0.0136 | 0.0142 ± 0.000560 | 0.122 | 0.127 ± 0.00500 | 78.4 |
| | 0.01432 | 0.0143 | | 0.128 | | |
| | 0.01475 | 0.0148 | | 0.132 | | |

Abbreviations:
SD, standard deviation;
VC, vehicle control (1% Methanol)
[a]The observed analyzed value (µM) was below the lowest concentration on the standard curve (0.01 µM).
Note:
For all calculations above, the resulting values are shown with at least three significant figures for display purposes only.

TABLE 22

CYP2C19 Activity in Cryopreserved Human Hepatocytes

| Metaxalone (µM) | Raw (µM) | 4'-Hydroxymephenytoin formation | | Specific Activity (pmol/min/million cells) | | Percent of VC |
|---|---|---|---|---|---|---|
| | | Adjusted (µM) | | | | |
| | | Individual | Mean ± SD | Individual | Mean ± SD | |
| Donor 1 | | | | | | |
| 0 | 0.00025[a] | <0.0500 | <0.0500 ± 0.000 | <0.446 | <0.446 ± 0.000 | 100 |
| (VC) | 0.00058[a] | <0.0500 | | <0.446 | | |
| | 0.00114[a] | <0.0500 | | <0.446 | | |
| | 0.00058[a] | <0.0500 | | <0.446 | | |
| 0.4 | 0.00708[a] | <0.0500 | <0.0500 ± 0.000 | <0.446 | <0.446 ± 0.000 | 100 |
| | 0.01319[a] | <0.0500 | | <0.446 | | |
| | 0.01861[a] | <0.0500 | | <0.446 | | |
| 4 | 0.01649[a] | <0.0500 | <0.0500 ± 0.000 | <0.446 | <0.446 ± 0.000 | 100 |
| | 0.00029[a] | <0.0500 | | <0.446 | | |
| | 0.00064[a] | <0.0500 | | <0.446 | | |
| 40 | 0.00057[a] | <0.0500 | <0.0500 ± 0.000 | <0.446 | <0.446 ± 0.000 | 100 |
| | 0.00031[a] | <0.0500 | | <0.446 | | |
| | 0.00037[a] | <0.0500 | | <0.446 | | |
| Donor 2 | | | | | | |
| 0 | N/A* | N/A | <0.0500 ± 0.000 | N/A | <0.446 ± 0.000 | 100 |
| (VC) | 0.01146[a] | <0.0500 | | <0.446 | | |
| | 0.01456[a] | <0.0500 | | <0.446 | | |
| | N/A* | N/A | | N/A | | |
| 0.4 | 0.00765[a] | <0.0500 | <0.0500 ± 0.000 | <0.446 | <0.446 ± 0.000 | 100 |
| | 0.00779[a] | <0.0500 | | <0.446 | | |
| | 0.00808[a] | <0.0500 | | <0.446 | | |
| 4 | 0.00775[a] | <0.0500 | <0.0500 ± 0.000 | <0.446 | <0.446 ± 0.000 | 100 |
| | 0.00744[a] | <0.0500 | | <0.446 | | |
| | 0.00773[a] | <0.0500 | | <0.446 | | |
| 40 | 0.00697[a] | <0.0500 | <0.0500 ± 0.000 | <0.446 | <0.446 ± 0.000 | 100 |
| | 0.00840[a] | <0.0500 | | <0.446 | | |
| | 0.00790[a] | <0.0500 | | <0.446 | | |
| Donor 3 | | | | | | |
| 0 | 0.00026[a] | <0.0500 | <0.0500 ± 0.000 | <0.446 | <0.446 ± 0.000 | 100 |
| (VC) | 0.00000[a] | <0.0500 | | <0.446 | | |
| | 0.00000[a] | <0.0500 | | <0.446 | | |
| | 0.00000[a] | <0.0500 | | <0.446 | | |

TABLE 22-continued

CYP2C19 Activity in Cryopreserved Human Hepatocytes

| Metaxalone (μM) | Raw (μM) | 4'-Hydroxymephenytoin formation Adjusted (μM) Individual | Adjusted (μM) Mean ± SD | Specific Activity (pmol/min/million cells) Individual | Specific Activity (pmol/min/million cells) Mean ± SD | Percent of VC |
|---|---|---|---|---|---|---|
| 0.4 | 0.00000[a] | <0.0500 | <0.0500 ± 0.000 | <0.446 | <0.446 ± 0.000 | 100 |
|  | 0.00000[a] | <0.0500 |  | <0.446 |  |  |
|  | 0.00023[a] | <0.0500 |  | <0.446 |  |  |
| 4 | 0.00000[a] | <0.0500 | <0.0500 ± 0.000 | <0.446 | <0.446 ± 0.000 | 100 |
|  | 0.00000[a] | <0.0500 |  | <0.446 |  |  |
|  | 0.00000[a] | <0.0500 |  | <0.446 |  |  |
| 40 | 0.00191[a] | <0.0500 | <0.0500 ± 0.000 | <0.446 | <0.446 ± 0.000 | 100 |
|  | 0.00000[a] | <0.0500 |  | <0.446 |  |  |
|  | 0.00000[a] | <0.0500 |  | <0.446 |  |  |

Abbreviations:
SD, standard deviation;
VC, vehicle control (1% Methanol)
[a] The observed analyzed value (μM) was below the lowest concentration on the standard curve (0.05 μM).
*Sample lost after preparation.
Note:
For all calculations above, the resulting values are shown with at least three significant figures for display purposes only.

TABLE 23

CYP2D6 Activity in Cryopreserved Human Hepatocytes

| Metaxalone (μM) | Raw (μM) | Dextrorphan formation Adjusted (μM) Individual | Adjusted (μM) Mean ± SD | Specific Activity (pmol/min/million cells) Individual | Specific Activity (pmol/min/million cells) Mean ± SD | Percent of VC |
|---|---|---|---|---|---|---|
| Donor 1 | | | | | | |
| 0 (VC) | 0.00772[a] | <0.0100 | <0.0100 ± 0.000 | <0.0893 | <0.0893 ± 0.000 | 100 |
|  | 0.00796[a] | <0.0100 |  | <0.0893 |  |  |
|  | 0.00736[a] | <0.0100 |  | <0.0893 |  |  |
|  | 0.00724[a] | <0.0100 |  | <0.0893 |  |  |
| 0.4 | 0.00809[a] | <0.0100 | <0.0100 ± 0.000 | <0.0893 | <0.0893 ± 0.000 | 100 |
|  | 0.00749[a] | <0.0100 |  | <0.0893 |  |  |
|  | 0.00853[a] | <0.0100 |  | <0.0893 |  |  |
| 4 | 0.00832[a] | <0.0100 | <0.0100 ± 0.000 | <0.0893 | <0.0893 ± 0.000 | 100 |
|  | 0.00721[a] | <0.0100 |  | <0.0893 |  |  |
|  | 0.00744[a] | <0.0100 |  | <0.0893 |  |  |
| 40 | 0.00398[a] | <0.0100 | <0.0100 ± 0.000 | <0.0893 | <0.0893 ± 0.000 | 100 |
|  | 0.00205[a] | <0.0100 |  | <0.0893 |  |  |
|  | 0.00520[a] | <0.0100 |  | <0.0893 |  |  |
| Donor 2 | | | | | | |
| 0 (VC) | 0.01286 | 0.0129 | 0.0139 ± 0.00152 | 0.115 | 0.124 ± 0.0136 | 100 |
|  | 0.01432 | 0.0143 |  | 0.128 |  |  |
|  | 0.01581 | 0.0158 |  | 0.141 |  |  |
|  | 0.01247 | 0.0125 |  | 0.111 |  |  |
| 0.4 | 0.01302 | 0.0130 | 0.0133 ± 0.000485 | 0.116 | 0.119 ± 0.00433 | 95.9 |
|  | 0.01302 | 0.0130 |  | 0.116 |  |  |
|  | 0.01386 | 0.0139 |  | 0.124 |  |  |
| 4 | 0.01361 | 0.0136 | 0.0143 ± 0.000589 | 0.122 | 0.128 ± 0.00526 | 103 |
|  | 0.01468 | 0.0147 |  | 0.131 |  |  |
|  | 0.01457 | 0.0146 |  | 0.130 |  |  |
| 40 | 0.00998[a] | <0.0100 | <0.0102 ± 0.000260 | <0.0893 | <0.0906 ± 0.00232 | <73.2 |
|  | 0.00956[a] | <0.0100 |  | <0.0893 |  |  |
|  | 0.01045 | 0.0105 |  | 0.0933 |  |  |
| Donor 3 | | | | | | |
| 0 (VC) | 0.07011 | 0.0701 | 0.0665 ± 0.00607 | 0.626 | 0.594 ± 0.0542 | 100 |
|  | 0.05856 | 0.0586 |  | 0.523 |  |  |
|  | 0.07219 | 0.0722 |  | 0.645 |  |  |
|  | 0.06505 | 0.0651 |  | 0.581 |  |  |
| 0.4 | 0.06218 | 0.0622 | 0.0657 ± 0.00305 | 0.555 | 0.586 ± 0.0272 | 98.8 |
|  | 0.06688 | 0.0669 |  | 0.597 |  |  |
|  | 0.06789 | 0.0679 |  | 0.606 |  |  |
| 4 | 0.06071 | 0.0607 | 0.0597 ± 0.00164 | 0.542 | 0.533 ± 0.0146 | 89.8 |
|  | 0.06060 | 0.0606 |  | 0.541 |  |  |
|  | 0.05782 | 0.0578 |  | 0.516 |  |  |

TABLE 23-continued

CYP2D6 Activity in Cryopreserved Human Hepatocytes

| Metaxalone | Raw | Dextrorphan formation | | Specific Activity | | Percent |
| | | Adjusted (µM) | | (pmol/min/million cells) | | |
| (µM) | (µM) | Individual | Mean ± SD | Individual | Mean ± SD | of VC |
|---|---|---|---|---|---|---|
| 40 | 0.05087 | 0.0509 | 0.0489 ± 0.00347 | 0.454 | 0.436 ± 0.0310 | 73.5 |
|  | 0.05088 | 0.0509 |  | 0.454 |  |  |
|  | 0.04486 | 0.0449 |  | 0.401 |  |  |

Abbreviations:

SD, standard deviation;

VC, vehicle control (1% Methanol)

[a] The observed analyzed value (µM) was below the lowest concentration on the standard curve (0.01 µM).

Note:

For all calculations above, the resulting values are shown with at least three significant figures for display purposes only.

TABLE 24

CYP2E1 Activity in Cryopreserved Human Hepatocytes

| Metaxalone | Raw | 6-Hydroxychlorzoxazone formation | | Specific Activity | | Percent |
| | | Adjusted (µM) | | (pmol/min/million cells) | | |
| (µM) | (µM) | Individual | Mean ± SD | Individual | Mean ± SD | of VC |
|---|---|---|---|---|---|---|
| \multicolumn{7}{c}{Donor 1} |
| 0 | 0.28067 | 0.281 | 0.283 ± 0.00460 | 2.51 | 2.53 ± 0.0411 | 100 |
| (VC) | 0.28793 | 0.288 |  | 2.57 |  |  |
|  | 0.28627 | 0.286 |  | 2.56 |  |  |
|  | 0.27817 | 0.278 |  | 2.48 |  |  |
| 0.4 | 0.28854 | 0.289 | 0.277 ± 0.0279 | 2.58 | 2.47 ± 0.249 | 97.8 |
|  | 0.29749 | 0.297 |  | 2.66 |  |  |
|  | 0.24529 | 0.245 |  | 2.19 |  |  |
| 4 | 0.28784 | 0.288 | 0.295 ± 0.0236 | 2.57 | 2.64 ± 0.210 | 104 |
|  | 0.27623 | 0.276 |  | 2.47 |  |  |
|  | 0.32160 | 0.322 |  | 2.87 |  |  |
| 40 | 0.28453 | 0.285 | 0.294 ± 0.00876 | 2.54 | 2.63 ± 0.0782 | 104 |
|  | 0.29753 | 0.298 |  | 2.66 |  |  |
|  | 0.30121 | 0.301 |  | 2.69 |  |  |
| \multicolumn{7}{c}{Donor 2} |
| 0 | 0.07385 | 0.0739 | 0.0748 ± 0.00211 | 0.659 | 0.668 ± 0.0188 | 100 |
| (VC) | 0.07610 | 0.0761 |  | 0.679 |  |  |
|  | 0.07690 | 0.0769 |  | 0.687 |  |  |
|  | 0.07229 | 0.0723 |  | 0.645 |  |  |
| 0.4 | 0.07071 | 0.0707 | 0.0776 ± 0.00753 | 0.631 | 0.693 ± 0.0673 | 104 |
|  | 0.07649 | 0.0765 |  | 0.683 |  |  |
|  | 0.08565 | 0.0857 |  | 0.765 |  |  |
| 4 | 0.06315 | 0.0632 | 0.0670 ± 0.00355 | 0.564 | 0.598 ± 0.0317 | 89.6 |
|  | 0.06775 | 0.0678 |  | 0.605 |  |  |
|  | 0.07013 | 0.0701 |  | 0.626 |  |  |
| 40 | 0.06247 | 0.0625 | 0.0745 ± 0.0141 | 0.558 | 0.665 ± 0.126 | 99.6 |
|  | 0.07091 | 0.0709 |  | 0.633 |  |  |
|  | 0.09003 | 0.0900 |  | 0.804 |  |  |
| \multicolumn{7}{c}{Donor 3} |
| 0 | 0.05899 | 0.0590 | 0.0570 ± 0.00420 | 0.527 | 0.509 ± 0.0375 | 100 |
| (VC) | 0.06077 | 0.0608 |  | 0.543 |  |  |
|  | 0.05718 | 0.0572 |  | 0.511 |  |  |
|  | 0.05110 | 0.0511 |  | 0.456 |  |  |
| 0.4 | 0.05031 | 0.0503 | 0.0517 ± 0.00140 | 0.449 | 0.462 ± 0.0125 | 90.7 |
|  | 0.05310 | 0.0531 |  | 0.474 |  |  |
|  | 0.05169 | 0.0517 |  | 0.462 |  |  |

TABLE 24-continued

CYP2E1 Activity in Cryopreserved Human Hepatocytes

| Metaxalone | 6-Hydroxychlorzoxazone formation | | | Specific Activity | | Percent |
|---|---|---|---|---|---|---|
| | Raw | Adjusted (µM) | | (pmol/min/million cells) | | |
| (µM) | (µM) | Individual | Mean ± SD | Individual | Mean ± SD | of VC |
| 4 | 0.05245 | 0.0525 | 0.0500 ± 0.00389 | 0.468 | 0.446 ± 0.0348 | 87.7 |
| | 0.05202 | 0.0520 | | 0.464 | | |
| | 0.04550 | 0.0455 | | 0.406 | | |
| 40 | 0.05260 | 0.0526 | 0.0535 ± 0.00164 | 0.470 | 0.478 ± 0.0146 | 93.9 |
| | 0.05541 | 0.0554 | | 0.495 | | |
| | 0.05254 | 0.0525 | | 0.469 | | |

Abbreviations:

SD, standard deviation;

VC, vehicle control (1% Methanol)

Note:

For all calculations above, the resulting values are shown with at least three significant figures for display purposes only.

TABLE 25

CYP3A4 Activity in Cryopreserved Human Hepatocytes

| Metaxalone | 6β-Hydroxytestosterone formation | | | Specific Activity | | Percent |
|---|---|---|---|---|---|---|
| | Raw | Adjusted (µM) | | (pmol/min/million cells) | | |
| (µM) | (µM) | Individual | Mean ± SD | Individual | Mean ± SD | of VC |
| Donor 1 | | | | | | |
| 0 | 0.05693[a] | <0.100 | <0.100 ± 0.000 | <0.893 | <0.893 ± 0.000 | 100 |
| (VC) | 0.05726[a] | <0.100 | | <0.893 | | |
| | 0.05367[a] | <0.100 | | <0.893 | | |
| | 0.04590[a] | <0.100 | | <0.893 | | |
| 0.4 | 0.05415[a] | <0.100 | <0.100 ± 0.000 | <0.893 | <0.893 ± 0.000 | 100 |
| | 0.06053[a] | <0.100 | | <0.893 | | |
| | 0.05911[a] | <0.100 | | <0.893 | | |
| 4 | 0.05783[a] | <0.100 | <0.100 ± 0.000 | <0.893 | <0.893 ± 0.000 | 100 |
| | 0.05948[a] | <0.100 | | <0.893 | | |
| | 0.05705[a] | <0.100 | | <0.893 | | |
| 40 | 0.06888[a] | <0.100 | <0.100 ± 0.000 | <0.893 | <0.893 ± 0.000 | 100 |
| | 0.06424[a] | <0.100 | | <0.893 | | |
| | 0.06511[a] | <0.100 | | <0.893 | | |
| Donor 2 | | | | | | |
| 0 | 0.12401 | 0.124 | <0.117 ± 0.0141 | 1.11 | <1.05 ± 0.126 | 100 |
| (VC) | 0.13222 | 0.132 | | 1.18 | | |
| | 0.07973[a] | <0.100 | | <0.893 | | |
| | 0.11219 | 0.112 | | 1.00 | | |
| 0.4 | 0.12083 | 0.121 | 0.134 ± 0.0122 | 1.08 | 1.20 ± 0.109 | >115 |
| | 0.14424 | 0.144 | | 1.29 | | |
| | 0.13828 | 0.138 | | 1.23 | | |
| 4 | 0.10953 | 0.110 | 0.116 ± 0.00524 | 0.978 | 1.03 ± 0.0468 | >98.7 |
| | 0.11883 | 0.119 | | 1.06 | | |
| | 0.11837 | 0.118 | | 1.06 | | |
| 40 | 0.14198 | 0.142 | 0.141 ± 0.00273 | 1.27 | 1.26 ± 0.0244 | >121 |
| | 0.14356 | 0.144 | | 1.28 | | |
| | 0.13824 | 0.138 | | 1.23 | | |
| Donor 3 | | | | | | |
| 0 | 0.06064[a] | <0.100 | <0.100 ± 0.000 | <0.893 | <0.893 ± 0.000 | 100 |
| (VC) | 0.05981[a] | <0.100 | | <0.893 | | |
| | 0.06402[a] | <0.100 | | <0.893 | | |
| | 0.08660[a] | <0.100 | | <0.893 | | |
| 0.4 | 0.05106[a] | <0.100 | <0.100 ± 0.000 | <0.893 | <0.893 ± 0.000 | 100 |
| | 0.08255[a] | <0.100 | | <0.893 | | |
| | 0.05998[a] | <0.100 | | <0.893 | | |
| 4 | 0.06298[a] | <0.100 | <0.100 ± 0.000 | <0.893 | <0.893 ± 0.000 | 100 |
| | 0.05381[a] | <0.100 | | <0.893 | | |
| | 0.07264[a] | <0.100 | | <0.893 | | |

TABLE 25-continued

CYP3A4 Activity in Cryopreserved Human Hepatocytes

| Metaxalone (μM) | 6β-Hydroxytestosterone formation | | | Specific Activity | | Percent of VC |
|---|---|---|---|---|---|---|
| | Raw (μM) | Adjusted (μM) | | (pmol/min/million cells) | | |
| | | Individual | Mean ± SD | Individual | Mean ± SD | |
| 40 | 0.05587[a] | <0.100 | <0.101 ± 0.00238 | <0.893 | <0.905 ± 0.0213 | 101 |
| | 0.10413 | 0.104 | | 0.930 | | |
| | 0.08088[a] | <0.100 | | <0.893 | | |

Abbreviations:
SD, standard deviation;
VC, vehicle control (1% Methanol);
[a]The observed analyzed value (μM) was below the lowest concentration on the standard curve (0.1 μM).
Note:
For all calculations above, the resulting values are shown with at least three significant figures for display purposes only.

Table 18 presents the results for CYP1A2. Under these experimental conditions, exposure to metaxalone at 40 μM induced CYP1A2 activity in human hepatocytes prepared from Donors 1, 2, and 3. For each of the three donors, the increases in CYP1A2 activity by metaxalone at 0.4 and 4 μM were not statistically significant (p>0.05; unpaired two-tailed t test).

Table 25 presents the results for CYP3A4. Metaxalone at the concentration of 40 μM induced CYP3A4 activity by about 21% in one of three donors tested, Donor 2. Therefore under these experimental conditions, exposure to metaxalone at 40 μM induced CYP3A4 activity in human hepatocytes prepared from Donor 2. The increase in CYP3A4 activity following treatment with metaxalone at 0.4 μM for Donor 2 was not statistically significant (p>0.05; unpaired two-tailed t test). CYP3A4 activity in the vehicle controls for Donor 1 and Donor 3 were below the lower limit of quantitation. Exposure of hepatocytes from Donors 1 and 3 to metaxalone at the concentrations tested did not induce CYP3A4 activity since the activity following treatment with metaxalone was still below the lower limit of quantitation at each tested concentration.

Table 21 presents the results for CYP2C9. Under these experimental conditions, exposure to metaxalone at 40 μM significantly reduced CYP2C9 activity in human hepatocytes prepared from Donors 1, 2, and 3. The observed changes in CYP2C9 activity following exposure to metaxalone at 0.4 and 4 μM were not statistically significant (p>0.05; two-tailed t test). Thus, under these experimental conditions, exposure to metaxalone at 40 μM inhibited CYP2C9 activity.

Table 23 presents the results for CYP2D6. CYP2D6 activity was below the lower limit of quantitation in the vehicle controls and for the metaxalone-exposed samples for Donor 1. However, under these experimental conditions, exposure to metaxalone at 40 μM significantly reduced CYP2D6 activity in human hepatocytes prepared from Donors 2 and 3. The observed changes in CYP2D6 activity following exposure to metaxalone at 0.4 and 4 μM were not statistically significant (p>0.05; two-tailed t test). Thus, under these experimental conditions, exposure to metaxalone at 40 μM inhibited CYP2D6 activity.

Example 4

Metabolic Phenotyping of Metaxalone

A follow-up metabolic phenotyping study was performed in light of the study of Example 1 to clarify the metabolic profile of metaxalone and the relative contribution of specific CYP isozymes to its overall metabolic clearance. Two complementary methodologies to determine metabolism of metaxalone were performed to corroborate results: determination of metabolism in pooled human liver microsomes in the presence of isozyme-selective enzyme inhibitors and a repeated determination of metabolism by singly expressed human recombinant CYP isozymes. The microsomal system approximates the in vivo distribution of hepatic enzymes. When the test compound is metabolized by multiple CYP isozymes, selective chemical inhibitors are used in human hepatic microsomes to identify the relative contribution of each isozyme. When combined with knowledge of the relative abundance of each P450 isoform in the pool of human liver microsomes being used, the relative contribution of different P450 enzymes in the metabolism of the compound of interest in human liver microsomes can be better evaluated Metaxalone (MW=221.26, Lot #P-1055-116A1, purity=99.8%) stock solutions at 1.875 mM were prepared in methanol and stored at −20° C. Stocks were diluted daily in the appropriate buffers such that the final organic solvent concentration was <1%.

Potassium phosphate monobasic, potassium phosphate dibasic, NADPH tetrasodium salts, and other reagents were purchased from Sigma Chemical Co. or equivalent vendors. Methanol (HPLC grade), water (HPLC grade), ethyl acetate, and other solvents were purchased from Fisher, Burdick & Jackson, J. T. Baker, Mallinckrodt, or equivalent vendors. All inhibitors were of the highest purity available. Furafylline, pilocarpine, thio-TEPA, quercetin, sulfaphenazole, ticlopidine, quinidine, clomethiazole, and ketoconazole were obtained from Sigma Chemical Co.

Human liver microsomes pooled from 15 individuals (male and female) (Pool HMMC-PL020; CellzDirect, Inc., In Vitro Products and Services Division) were used in some experiments of this study. This pool of human liver microsomes was characterized by CellzDirect, Inc with respect to donor medical history, major cytochrome P450 enzyme activities and kinetic parameters, as well as for polymorphic forms for CYP2C9, CYP2C19, and CYP2D6 present in the individual donors of the pool.

In these follow-up studies, metaxalone concentrations were chosen to be 0.75 and 7.5 μM, approximately 1× and 0.1× of $C_{max}$ based on the estimated clinical plasma concentrations of metaxalone provided on the August 2003 version of the package insert for SKELAXIN®.

An isocratic LC-MS/MS was developed to allow for chromatographic resolution and quantitation of metaxalone contained within an incubation matrix for this concentration range. The following LC-MS/MS method was used for metaxalone quantitation:

TABLE 26

LC/MS method for metaxalone quantitation.

Metaxalone

| | |
|---|---|
| Substrate: Metabolite: | Metaxalone |
| Standard Metabolite Range: | 0.078 to 10.0 µM |
| Mobile Phase A | 2% Methanol, 98% Water, and 0.1% Acetic Acid |
| Mobile Phase B | 80% Methanol, 20% Water, and 0.1% Acetic Acid |
| Gradient | 0.400 mL/min, initial: 50% Mobile Phase B, 0.01 min: 50% Mobile Phase B, 2.00 min: 80% Mobile Phase B, 2.10 min: 50% Mobile Phase B, and 4.00 min: Stop |
| Detection Method: | LC-MS/MS |
| HPLC Column: | WATERS AQ12 4 × 23 mm |
| Flow rate (approx.): | 0.400 mL/min |
| Source: | Electrospray (positive ion) |
| Run Time (approx.): | 4.0 minutes |
| MRM (Sulfamethoxazole): | 222.14 → 160.83 |
| Quantitation: | Least Squares Regression $1/X^2$ Weighting |

Micromass MASSLYNX® software (version 3.4, Manchester, UK) was used to collect and process chromatographic data. Data were graphed and analyzed using the software program Microsoft EXCEL® 2003 (Redmond, Wash.). Percent turnover of metaxalone was calculated using the following equation:

$$\% \text{ Turnover} = 100 - \{[TA(\text{final})]/[\text{mean of } TA(0 \text{ min})]\} \times 100,$$

where TA(sample group)=Test Article (i.e., metaxalone) and the particular sample group is noted within the parentheses. Percent inhibition of turnover of metaxalone was calculated using the following equation:

$$\% \text{ Inhibition of Turnover} = 100\{1 - ([TA(0 \text{ min})] - [TA(\text{final-inhibitor})])/([TA(0 \text{ min})] - [TA(\text{final-no inhibitor})])\}.$$

Pilot human liver microsomal incubations were performed in order to establish appropriate protein concentration and time points for linear reaction conditions for metaxalone turnover. Metaxalone at 0.75 or 7.5 µM was incubated with 0.1, 0.25, 0.5, and 1.0 mg/mL microsomal protein for 60 minutes at 37° C. Also, incubations of metaxalone at 0.75 or 7.5 µM with 0.5 mg/mL microsomal protein were run for 0, 15, 30, 45, and 60 minutes at 37° C. The reactions, in 0.1 M phosphate buffer, pH 7.4, were initiated by addition of 1 mM NADPH. Negative controls (no NADPH and heat-treated microsomes) were included to account for any non-enzymatic or non-NADPH dependent reactions. The reactions were terminated at the appropriate time points by addition of 1 volume (relative to total reaction volume) of methanol. The samples were centrifuged at approximately 3000 rpm and the clear supernatant was transferred to a clean tube and analyzed by the LC-MS/MS method described above.

Linear disappearance of metaxalone from the pooled human liver microsomal incubations was observed for both the time- and microsomal protein-dependence incubation series. A maximum turnover of 38.0% was determined at 60 minutes with 1 mg/mL protein. This turnover was NADPH-dependent, indicating that disappearance of metaxalone under these conditions was due to CYP450 enzymatic activity. Based on these results, all subsequent assays used a microsomal protein concentration of 1 mg/mL with an incubation time of 60 minutes to maximize the dynamic range of metaxalone turnover.

Selective chemical inhibitors were then used to evaluate the effects of individual CYP450s in human liver microsomes on the metabolism of metaxalone. The CYP isozyme-selective chemical inhibitors and concentrations used are shown in Table 27 below.

TABLE 27

Selective Chemical Inhibitors and Concentrations Used in Protocols for in vitro Assessment of Chemical Inhibition in Human Liver Microsomes.

| P450 Isozyme | Selective chemical inhibitor | Concentration |
|---|---|---|
| CYP1A2 | Furafylline | 50 µM |
| CYP2A6 | Pilocarpine | 100 µM |
| CYP2B6 | Thio-TEPA | 75 µM |
| CYP2C8 | Quercetin | 10 µM |
| CYP2C9 | Sulfaphenazole | 20 µM |
| CYP2C19 | Ticlopidine | 1 µM |
| CYP2D6 | Quinidine | 10 µM |
| CYP2E1 | Clomethiazole | 100 µM |
| CYP3A4 | Ketoconazole | 1 µM |

The inhibitors or vehicle control were incubated with the pooled human liver microsomes (1 mg/mL) and NADPH (1 mM) in 0.1 M phosphate buffer, pH 7.4. The reaction was initiated by addition of 0.75 or 7.5 µM metaxalone and incubated for 60 minutes. Incubations were conducted in triplicate and terminated by addition of organic solvent. Samples were extracted and analyzed by LC-MS/MS as described above. The rates of metaxalone depletion were compared to controls without inhibitors.

The data from these studies are provided in Tables 28 and 29, below.

TABLE 28

Chemical Inhibitor Data in Human Liver Microsomes with 0.75 μM Metaxalone

| Inhibitor | CYP | Sample ID | Conc. (μM) | Mean Conc. (μM) | % Turnover | Mean | Std. Error | % inhibition of turnover | Mean | Std Error |
|---|---|---|---|---|---|---|---|---|---|---|
| | | 0.75 uM-T0-P1.0-1 | 0.730 | | | | | | | |
| | | 0.75 uM-T0-P1.0-2 | 0.815 | | | | | | | |
| | 0 min. | 0.75 uM-T0-P1.0-3 | 0.770 | 0.772 | | | | | | |
| | | 0.75 uM-T60-P1.0-1 | 0.536 | | 30.5 | | | | | |
| | | 0.75 uM-T60-P1.0-2 | 0.561 | | 27.3 | | | | | |
| | 60 min. | 0.75 uM-T60-P1.0-3 | 0.529 | 0.542 | 31.5 | 29.8 | 1.3 | | | |
| | | 0.75 uM-T60-P1.0-F-1 | 0.924 | | −19.7 | | | 166 | | |
| | | 0.75 uM-T60-P1.0-F-2 | 0.767 | | 0.60 | | | 98.0 | | |
| Furafylline | CYP1A2 | 0.75 uM-T60-P1.0-F-3 | 0.701 | 0.797 | 9.2 | −3.29 | 8.57 | 69.1 | 111 | 29 |
| | | 0.75 uM-T60-P1.0-P-1 | 0.664 | | 13.9 | | | 53.2 | | |
| | | 0.75 uM-T60-P1.0-P-2 | 0.658 | | 14.7 | | | 50.6 | | |
| Pilocarpine | CYP2A6 | 0.75 uM-T60-P1.0-P-3 | 0.622 | 0.648 | 19.4 | 16.0 | 1.7 | 34.9 | 46.2 | 5.7 |
| | | 0.75 uM-T60-P1.0-TT-1 | 0.678 | | 12.1 | | | 59.3 | | |
| | | 0.75 uM-T60-P1.0-TT-2 | 0.684 | | 11.3 | | | 62.0 | | |
| Thio-TEPA | CYP2B6 | 0.75 uM-T60-P1.0-TT-3 | 0.665 | 0.676 | 13.8 | 12.4 | 0.7 | 53.7 | 58.3 | 2.4 |
| | | 0.75 uM-T60-P1.0-Qr-1 | 0.661 | | 14.3 | | | 51.9 | | |
| | | 0.75 uM-T60-P1.0-Qr-2 | 0.769 | | 0.39 | | | 98.7 | | |
| Quercetin | CYP2C8 | 0.75 uM-T60-P1.0-Qr-3 | 0.728 | 0.719 | 5.6 | 6.78 | 4.06 | 81.1 | 77.2 | 13.6 |
| | | 0.75 uM-T60-P1.0-S-1 | 0.730 | | 5.4 | | | 81.9 | | |
| | | 0.75 uM-T60-P1.0-S-2 | 0.728 | | 5.6 | | | 81.1 | | |
| Sulfaphenazole | CYP2C9 | 0.75 uM-T60-P1.0-S-3 | 0.729 | 0.729 | 5.6 | 5.53 | 0.08 | 81.3 | 81.4 | 0.3 |
| | | 0.75 uM-T60-P1.0-Ti-1 | 0.698 | | 9.6 | | | 67.9 | | |
| | | 0.75 uM-T60-P1.0-Ti-2 | 0.714 | | 7.5 | | | 74.7 | | |
| Ticlopidine | CYP2C19 | 0.75 uM-T60-P1.0-Ti-3 | 0.715 | 0.709 | 7.4 | 8.16 | 0.70 | 75.2 | 72.6 | 2.3 |
| | | 0.75 uM-T60-P1.0-Qi-1 | 0.694 | | 10.0 | | | 66.4 | | |
| | | 0.75 uM-T60-P1.0-Qi-2 | 0.920 | | −19.2 | | | 165 | | |
| Quinidine | CYP2D6 | 0.75 uM-T60-P1.0-Qi-3 | 0.692 | 0.769 | 10.3 | 0.376 | 9.796 | 65.4 | 98.7 | 32.9 |
| | | 0.75 uM-T60-P1.0-Clo-1 | 0.780 | | −1.1 | | | 104 | | |
| | | 0.75 uM-T60-P1.0-Clo-2 | 0.896 | | −16.1 | | | 154 | | |
| Clomethiazole | CYP2E1 | 0.75 uM-T60-P1.0-Clo-3 | 0.729 | 0.802 | 5.6 | −3.87 | 6.39 | 81.4 | 113 | 21 |
| | | 0.75 uM-T60-P1.0-K-1 | 0.844 | | −9.4 | | | 132 | | |
| | | 0.75 uM-T60-P1.0-K-2 | 0.807 | | −4.6 | | | 116 | | |
| Ketoconazole | CYP3A4 | 0.75 uM-T60-P1.0-K-3 | 0.842 | 0.831 | −9.1 | −7.71 | 1.54 | 130 | 126 | 5 |

TABLE 29

Chemical Inhibitor Data in Human Liver Microsomes with 7.5 μM Metaxalone

| Inhibitor | CYP | Sample ID | Conc. (μM) | Mean Conc. (μM) | % Turnover | Mean | Std. Error | % inhibition of turnover | Mean | Std Error |
|---|---|---|---|---|---|---|---|---|---|---|
| | | 7.5 uM-T0-P1.0-1 | 8.34 | | | | | | | |
| | | 7.5 uM-T0-P1.0-2 | 8.55 | | | | | | | |
| | 0 min. | 7.5 uM-T0-P1.0-3 | 8.65 | 8.51 | | | | | | |
| | | 7.5 uM-T60-P1.0-1 | 6.40 | | 24.8 | | | | | |
| | | 7.5 uM-T60-P1.0-2 | 6.48 | | 23.9 | | | | | |
| | 60 min. | 7.5 uM-T60-P1.0-3 | 6.38 | 6.42 | 25.1 | 24.6 | 0.3 | | | |
| | | 7.5 uM-T60-P1.0-F-1 | 8.07 | | 5.2 | | | 78.8 | | |
| | | 7.5 uM-T60-P1.0-F-2 | 8.21 | | 3.6 | | | 85.4 | | |
| Furafylline | CYP1A2 | 7.5 uM-T60-P1.0-F-3 | 8.05 | 8.11 | 5.5 | 4.77 | 0.59 | 77.7 | 80.6 | 2.4 |
| | | 7.5 uM-T60-P1.0-P-1 | 7.76 | | 8.8 | | | 64.2 | | |
| | | 7.5 uM-T60-P1.0-P-2 | 7.28 | | 14.5 | | | 41.2 | | |
| Pilocarpine | CYP2A6 | 7.5 uM-T60-P1.0-P-3 | 7.41 | 7.48 | 13.0 | 12.1 | 1.7 | 47.1 | 50.8 | 6.9 |
| | | 7.5 uM-T60-P1.0-TT-1 | 7.86 | | 7.7 | | | 68.7 | | |
| | | 7.5 uM-T60-P1.0-TT-2 | 7.26 | | 14.8 | | | 40.0 | | |
| Thio-TEPA | CYP2B6 | 7.5 uM-T60-P1.0-TT-3 | 6.86 | 7.33 | 19.4 | 14.0 | 3.4 | 21.1 | 43.3 | 13.8 |
| | | 7.5 uM-T60-P1.0-Qr-1 | 8.67 | | −1.8 | | | 107 | | |
| | | 7.5 uM-T60-P1.0-Qr-2 | 8.48 | | 0.45 | | | 98.2 | | |
| Quercetin | CYP2C8 | 7.5 uM-T60-P1.0-Qr-3 | 7.43 | 8.19 | 12.7 | 3.77 | 4.50 | 48.5 | 84.7 | 18.3 |
| | | 7.5 uM-T60-P1.0-S-1 | 7.49 | | 12.1 | | | 51.0 | | |
| | | 7.5 uM-T60-P1.0-S-2 | 7.65 | | 10.2 | | | 58.5 | | |

TABLE 29-continued

Chemical Inhibitor Data in Human Liver Microsomes with 7.5 µM Metaxalone

| Inhibitor | CYP | Sample ID | Conc. (µM) | Mean Conc. (µM) | % Turnover | Mean | Std. Error | % inhibition of turnover | Mean | Std Error |
|---|---|---|---|---|---|---|---|---|---|---|
| Sulfaphenazole | CYP2C9 | 7.5 uM-T60-P1.0-S-3 | 7.44 | 7.52 | 12.6 | 11.6 | 0.7 | 48.8 | 52.8 | 2.9 |
| | | 7.5 uM-T60-P1.0-Ti-1 | 8.02 | | 5.8 | | | 76.5 | | |
| | | 7.5 uM-T60-P1.0-Ti-2 | 7.58 | | 11.0 | | | 55.5 | | |
| Ticlopidine | CYP2C19 | 7.5 uM-T60-P1.0-Ti-3 | 9.50 | 8.37 | −11.6 | 1.71 | 6.83 | 147 | 93.1 | 27.7 |
| | | 7.5 uM-T60-P1.0-Qi-1 | 7.62 | | 10.5 | | | 57.5 | | |
| | | 7.5 uM-T60-P1.0-Qi-2 | 7.80 | | 8.4 | | | 65.9 | | |
| Quinidine | CYP2D6 | 7.5 uM-T60-P1.0-Qi-3 | 7.57 | 7.66 | 11.1 | 10.0 | 0.8 | 55.1 | 59.5 | 3.3 |
| | | 7.5 uM-T60-P1.0-Clo-1 | 8.29 | | 2.7 | | | 89.2 | | |
| | | 7.5 uM-T60-P1.0-Clo-2 | 8.54 | | −0.25 | | | 101 | | |
| Clomethiazole | CYP2E1 | 7.5 uM-T60-P1.0-Clo-3 | 8.63 | 8.48 | −1.3 | 0.356 | 1.197 | 105 | 98.6 | 4.9 |
| | | 7.5 uM-T60-P1.0-K-1 | 8.49 | | 0.28 | | | 98.8 | | |
| | | 7.5 uM-T60-P1.0-K-2 | 9.78 | | −14.9 | | | 161 | | |
| Ketoconazole | CYP3A4 | 7.5 uM-T60-P1.0-K-3 | 9.12 | 9.13 | −7.1 | −7.26 | 4.39 | 129 | 130 | 18 |

Mean metaxalone disappearance after 60 minutes of incubation with 1 mg/mL microsomal protein was observed to be 24.6±0.3% at 7.5 µM (Table 29) vs. 29.8±1.3% at 0.75 µM (Table 28) at the conditions examined.

Inhibition of metaxalone disappearance in human liver microsomes at either 0.75 or 7.5 µM metaxalone was observed upon addition of the CYP1A2 selective inhibitor furafylline (111±29% or 80.6±2.4%), the CYP3A4 inhibitor ketoconazole (126±5% or 130±18%), the CYP2E1 inhibitor clomethiazole (113±21% or 98.6±4.9%), the CYP2C19 inhibitor ticlopidine (72.6±2.3% or 93.1±27.7%), the CYP2D6 inhibitor quinidine (98.7±32.9% or 59.5±4.9%), the CYP2C9 inhibitor sulfaphenazole (81.4±0.3% or 52.8±2.9%), and the CYP2C8 inhibitor quercetin (77.2±13.6% or 84.7±18.3%) (See Tables 28-29). Smaller inhibition of turnover was also observed upon addition of the CYP2A6 inhibitor pilocarpine (46.2±5.7% or 50.8±6.9%) or the CYP2B6 inhibitor thio-TEPA (58.3±2.4% or 43.3±13.8%), however the observed inhibition of metaxalone metabolism by these two inhibitors in the pooled human liver microsomal system was not supported by the singly expressed recombinant CYP isozyme data.

Overall, this study in pooled human liver microsomes indicates that metaxalone can be metabolized to some extent by each of CYP1A2, CYP2C8, CYP2C9, CYP2C19, CYP2D6, CYP2E1, and CYP3A4, with CYP1A2, CYP2E1, and CYP3A4 appearing to be the major CYP450 enzymes involved.

An additional set of experiments using singly-expressed recombinant human CYP enzymes were conducted to corroborate which specific CYP450s are capable of metabolizing colchicines.

Commercially available microsomes from baculovirus-infected insect cells containing singly-expressed recombinant human CYP enzymes and cDNA-expressed human cytochrome p450 oxidoreductase [BD SUPERSOMES® Enzymes; BD Biosciences Discovery Labware (Woburn, Mass.)] were used. For CYP2A6, CYP2C9, CYP2C19, and CYP2E1, the SUPERSOMES® also expressed human cytochrome b5 in addition to human cytochrome p450 oxidoreductase and the human CYP isozyme. For CYP2C9 and CYP2D6, SUPERSOMES singly-expressing different allelic variants of the cytochrome p450 isozyme were commercially available. For each of CYP2C9 and CYP2D6, only the *1 allele was tested in these experiments.

Incubation mixtures containing CYP1A2, CYP2A6, CYP2B6, CYP2C8, CYP2C9, CYP2C19, CYP2D6, CYP2E1, and CYP3A4 singly-expressed enzymes at 5 and 20 pmol cytochrome P450 were incubated in 0.1 M phosphate buffer, pH 7.4 with 1 mM NADPH and 0.75 or 7.5 µM metaxalone for 60 minutes at 37° C. The incubations, performed in triplicate, were terminated by addition of 1 volume (relative to total reaction volume) of methanol. The samples were extracted and analyzed by LC-MS/MS, as described above. The amount of metaxalone depletion by the CYP were compared to the amount of depletion in a control for native activity (microsomes expressing no recombinant CYP450 enzyme).

An additional control for each isoform included verification that the isoform was active by incubating mixtures with the universal CYP substrate, phenanthrene, and monitoring turnover of phenanthrene fluorometrically at 254 nm (excitation) and 378 nm (emission). These controls confirmed that each recombinant enzyme microsomal preparation was active (data not shown).

The results measuring metaxalone disappearance at either 0.75 or 7.5 µM metaxalone in incubations containing either 5 or 20 pmol of a recombinant cytochrome P450 isozyme is summarized below in Tables 30-32.

TABLE 30

Metabolism of Metaxalone (0.75 µM) by Expressed Recombinant Human Cytochromes P450 at 5 or 20 pmol

| | | 5 pmol cyp | | | | | | 20 pmol cyp | | | | | |
|---|---|---|---|---|---|---|---|---|---|---|---|---|---|
| | | [metaxalone] | | | | % Turnover | | [metaxalone] | | | | % Turnover | |
| | µM | Mean | Std dev | p | % | Mean | Std Error | µM | Mean | Std dev | p | % | Mean | Std Error |
| control | 0.786 | | | | | | | 0.786 | | | | | | |
| control | 0.802 | | | | | | | 0.802 | | | | | | |

TABLE 30-continued

Metabolism of Metaxalone (0.75 μM) by Expressed Recombinant Human Cytochromes P450 at 5 or 20 pmol

| | 5 pmol cyp | | | | | | | 20 pmol cyp | | | | | | |
|---|---|---|---|---|---|---|---|---|---|---|---|---|---|---|
| | [metaxalone] | | | | % Turnover | | | [metaxalone] | | | | % Turnover | | |
| | μM | Mean | Std dev | p | % | Mean | Std Error | μM | Mean | Std dev | p | % | Mean | Std Error |
| control | 0.785 | 0.791 | 0.10 | | | | | 0.785 | 0.791 | 0.10 | | | | |
| 1A2 | 0.653 | | | | 17.5 | | | 0.540 | | | | 31.7 | | |
| 1A2 | 0.742 | | | | 6.2 | | | 0.511 | | | | 35.5 | | |
| 1A2 | 0.761 | 0.719 | 0.06 | 0.099 | 3.9 | 9.2 | 4.2 | 0.496 | 0.516 | 0.02 | <0.0001 | 37.3 | 34.8 | 1.6 |
| 2A6 | 0.777 | | | | 1.8 | | | 0.837 | | | | -5.7 | | |
| 2A6 | 0.824 | | | | -4.1 | | | 0.762 | | | | 3.7 | | |
| 2A6 | 0.769 | 0.790 | 0.03 | 0.96 | 2.8 | 0.14 | 2.16 | 0.753 | 0.784 | 0.05 | 0.81 | 4.8 | 0.91 | 3.33 |
| 2B6 | 0.878 | | | | -11.0 | | | 0.748 | | | | 5.5 | | |
| 2B6 | 0.813 | | | | -2.8 | | | 0.845 | | | | -6.7 | | |
| 2B6 | 0.843 | 0.845 | 0.03 | 0.052 | -6.6 | -6.8 | 2.4 | 0.823 | 0.805 | 0.05 | 0.66 | -4.0 | -1.8 | 3.7 |
| 2C8 | 0.812 | | | | -2.6 | | | 0.790 | | | | 0.19 | | |
| 2C8 | 0.877 | | | | -10.9 | | | 0.743 | | | | 6.1 | | |
| 2C8 | 0.905 | 0.865 | 0.05 | 0.059 | -14.3 | -9.3 | 3.5 | 0.771 | 0.768 | 0.02 | 0.19 | 2.5 | 2.9 | 1.7 |
| 2C9 | 0.743 | | | | 6.1 | | | 0.722 | | | | 8.7 | | |
| 2C9 | 0.749 | | | | 5.4 | | | 0.760 | | | | 4.0 | | |
| 2C9 | 0.845 | 0.779 | 0.06 | 0.74 | -6.8 | 1.6 | 4.2 | 0.834 | 0.772 | 0.06 | 0.60 | -5.4 | 2.4 | 4.2 |
| control | 0.738 | | | | | | | 0.738 | | | | | | |
| control | 0.697 | | | | | | | 0.697 | | | | | | |
| control | 0.701 | 0.712 | 0.023 | | | | | 0.701 | 0.712 | 0.023 | | | | |
| 2C19 | 0.696 | | | | 2.2 | | | 0.659 | | | | 7.4 | | |
| 2C19 | 0.658 | | | | 7.6 | | | 0.618 | | | | 13.3 | | |
| 2C19 | 0.634 | 0.662 | 0.031 | 0.091 | 11.0 | 6.9 | 2.5 | 0.591 | 0.623 | 0.034 | 0.020 | 16.9 | 12.5 | 2.8 |
| 2D6 | 0.649 | | | | 8.8 | | | 0.546 | | | | 23.3 | | |
| 2D6 | 0.629 | | | | 11.6 | | | 0.593 | | | | 16.7 | | |
| 2D6 | 0.647 | 0.642 | 0.011 | 0.0084 | 9.1 | 9.9 | 0.9 | 0.581 | 0.573 | 0.024 | 0.0020 | 18.5 | 19.5 | 2.0 |
| 2E1 | 0.693 | | | | 2.7 | | | 0.608 | | | | 14.6 | | |
| 2E1 | 0.604 | | | | 15.1 | | | 0.622 | | | | 12.6 | | |
| 2E1 | 0.596 | 0.631 | 0.054 | 0.074 | 16.3 | 11.3 | 4.4 | 0.560 | 0.597 | 0.033 | 0.0073 | 21.3 | 16.2 | 2.6 |
| 3A4 | 0.567 | | | | 20.3 | | | 0.486 | | | | 31.7 | | |
| 3A4 | 0.582 | | | | 18.3 | | | 0.434 | | | | 39.0 | | |
| 3A4 | 0.605 | 0.585 | 0.019 | 0.0017 | 15.0 | 17.9 | 1.6 | 0.488 | 0.470 | 0.031 | 0.0004 | 31.4 | 34.0 | 2.5 |

TABLE 31

Metabolism of Metaxalone (7.5 μM) by Expressed Recombinant Human Cytochromes P450 at 5 or 20 pmol

| | 5 pmol cyp | | | | | | | 20 pmol cyp | | | | | | |
|---|---|---|---|---|---|---|---|---|---|---|---|---|---|---|
| | [metaxalone] | | | | % Turnover | | | [metaxalone] | | | | % Turnover | | |
| | μM | Mean | Std dev | p | % | Mean | Std Error | μM | Mean | Std dev | p | % | Mean | Std Error |
| control | 8.52 | | | | | | | 8.52 | | | | | | |
| control | 8.41 | | | | | | | 8.41 | | | | | | |
| control | 8.40 | 8.44 | 0.07 | | | | | 8.40 | 8.45 | 0.07 | — | | | |
| 1A2 | 7.24 | | | | 14.3 | | | 5.63 | | | | 33.3 | | |
| 1A2 | NA | | | | NA | | | 5.72 | | | | 32.3 | | |
| 1A2 | 7.97 | 7.60 | — | — | 5.7 | 10.0 | 4.3 | 6.29 | 5.88 | 0.36 | 0.0003 | 25.5 | 30.4 | 2.4 |
| 2A6 | 7.69 | | | | 9.0 | | | 8.58 | | | | -1.6 | | |
| 2A6 | 8.08 | | | | 4.3 | | | 7.93 | | | | 6.1 | | |
| 2A6 | 8.64 | 8.14 | 0.48 | 0.16 | -2.3 | 3.7 | 3.3 | 9.27 | 8.59 | 0.67 | 0.72 | -9.8 | -1.8 | 4.6 |
| 2B6 | 8.56 | | | | -1.3 | | | 8.95 | | | | -6.0 | | |
| 2B6 | 8.19 | | | | 3.0 | | | 8.29 | | | | 1.8 | | |
| 2B6 | 7.84 | 8.20 | 0.36 | 0.31 | 7.2 | 3.0 | 2.5 | 8.14 | 8.46 | 0.43 | 0.95 | 3.6 | -0.20 | 2.93 |
| 2C8 | 7.58 | | | | 10.3 | | | 8.09 | | | | 4.3 | | |
| 2C8 | 8.43 | | | | 0.21 | | | 7.59 | | | | 10.2 | | |
| 2C8 | 8.58 | 8.20 | 0.54 | 0.48 | -1.6 | 3.0 | 3.7 | 7.31 | 7.66 | 0.40 | 0.028 | 13.4 | 9.3 | 2.7 |
| 2C9 | 7.24 | | | | 14.3 | | | 8.54 | | | | -1.1 | | |
| 2C9 | 8.20 | | | | 2.9 | | | 8.31 | | | | 1.6 | | |
| 2C9 | 7.90 | 7.78 | 0.49 | 0.08 | 6.4 | 7.9 | 3.4 | 7.54 | 8.13 | 0.52 | 0.36 | 10.7 | 3.7 | 3.6 |
| control | 7.36 | | | | | | | 7.36 | | | | | | |
| control | 7.85 | | | | | | | 7.85 | | | | | | |
| control | 7.93 | 7.71 | 0.31 | — | | | | 7.93 | 7.71 | | | | | |
| 2C19 | 7.69 | | | | 0.25 | | | 6.16 | | | | 20.2 | | |
| 2C19 | 7.17 | | | | 7.1 | | | 6.32 | | | | 18.0 | | |
| 2C19 | 6.82 | 7.23 | 0.44 | 0.19 | 11.6 | 6.3 | 3.3 | 6.34 | 6.27 | 0.10 | 0.0015 | 17.8 | 18.7 | 0.8 |
| 2D6 | 6.89 | | | | 10.7 | | | 5.87 | | | | 23.9 | | |

TABLE 31-continued

Metabolism of Metaxalone (7.5 μM) by Expressed Recombinant Human Cytochromes P450 at 5 or 20 pmol

| | 5 pmol cyp | | | | | | | 20 pmol cyp | | | | | | |
|---|---|---|---|---|---|---|---|---|---|---|---|---|---|---|
| | [metaxalone] | | | | % Turnover | | | [metaxalone] | | | | % Turnover | | |
| | μM | Mean | Std dev | p | % | Mean | Std Error | μM | Mean | Std dev | p | % | Mean | Std Error |
| 2D6 | 6.75 | | | | 12.5 | | | 5.90 | | | | 23.5 | | |
| 2D6 | 6.60 | 6.74 | 0.15 | 0.0080 | 14.5 | 12.6 | 1.1 | 5.61 | 5.79 | 0.16 | 0.0007 | 27.3 | 24.9 | 1.2 |
| 2E1 | 6.41 | | | | 16.9 | | | 6.33 | | | | 18.0 | | |
| 2E1 | 6.42 | | | | 16.7 | | | 6.25 | | | | 19.0 | | |
| 2E1 | 6.04 | 6.29 | 0.22 | 0.0028 | 21.7 | 18.4 | 1.6 | 6.60 | 6.39 | 0.18 | 0.0031 | 14.5 | 17.2 | 1.4 |
| 3A4 | 6.36 | | | | 17.5 | | | 5.07 | | | | 34.3 | | |
| 3A4 | 6.43 | | | | 16.7 | | | 5.18 | | | | 32.8 | | |
| 3A4 | 6.50 | 6.43 | 0.07 | 0.0022 | 15.7 | 16.6 | 0.5 | 5.40 | 5.22 | 0.17 | 0.0003 | 30.0 | 32.4 | 1.2 |

NA—NOT INCLUDED IN CALCULATIONS; NO PEAK DETECTED.

In these experiments, several CYP450s at both 5 and 20 pmoles were shown to be capable of metabolizing metaxalone at 0.75 μM including CYP3A4, CYP2E1, CYP2D6, CYP2C19, and CYP1A2 which showed percent turnover of 17.9, 11.3, 9.9, 6.9 and 9.2% at 5 pmol CYP450, and 34.0, 16.2, 19.5, 12.5, and 34.8% at 20 pmol, respectively. At 7.5 μM metaxalone CYP3A4, CYP2E1, CYP2D6, CYP2C19, and CYP1A2 were most effective with percent turnovers of 16.6, 18.4, 12.6, 6.3, and 10.0% at 5 pmol CYP450, and 32.4, 17.2, 24.9, 18.7, and 30.4% at 20 pmol CYP450, respectively. At the higher metaxalone concentration, CYP2C8 and CYP2C9 also moderately metabolized metaxalone (ranging from 3.0% to 9.3% turnover). These data indicate that multiple CYP450s can contribute to the metabolism of metaxalone, with CYP1A2, CYP3A4, CYP2E1, CYP2C19, and CYP2D6 producing the largest percentages for metaxalone metabolism under these conditions.

By combining both approaches to analysis of metaxalone metabolism, selective chemical inhibitors against metabolism by pooled human liver microsomes and individual recombinant CYP450 expressed in microsomes, metaxalone appears to be a substrate for CYP1A2, CYP2C8, CYP2C9, CYP2C19, CYP2D6, CYP2E1, and CYP3A4, with metabolism in the human liver likely to be primarily by hepatic cytochrome P450 isozymes CYP1A2, CYP2E1, and CYP3A4, with possible additional contributions to metabolism by hepatic cytochrome P450 isozymes CYP2C19, CYP2C8, CYP2D6, and CYP2C9.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. A method administering metaxalone to a patient in need of a skeletal muscle relaxant, comprising
    determining that a substance that is a known inducer or a known inhibitor of a cytochrome P450 isozyme (CYP) selected from CYP2C8, CYP2C9, and CYP2C19 is administered to a patient in need of a skeletal muscle relaxant; and
    administering a dose of metaxalone greater than a standard dose if a known inducer of the CYP is administered to the patient or administering a dose less than the standard dose of metaxalone if a known inhibitor of the CYP is administered to the patient.

2. The method of 1, wherein the standard dose of metaxalone is 800 mg.

3. The method of claim 1, further comprising
    determining a frequency per day at which the dose is administered to the patient.

4. The method of claim 1, further comprising
    monitoring plasma concentration of metaxalone in the patient to determine if the patient is at risk of a subtherapeutic outcome or of a metaxalone toxicity.

5. The method of claim 1 wherein the patient in need of a skeletal muscle relaxant has a musculoskeletal condition.

6. The method of claim 3, wherein if the patient is taking a known inducer of the CYP a daily dosing regimen of metaxalone administered to the patient consists of a daily amount of metaxalone greater than that provided by a standard metaxalone daily dosing regimen consisting of 800 mg, three or four times daily, or
    if the patient is taking a known inhibitor of the CYP a daily dosing regimen of metaxalone administered to the patient consists of a daily amount of metaxalone less than that provided by the standard metaxalone daily dosing regimen.

7. The method of claim 1, wherein the selected CYP is CYP2C8 and a known inducer of the selected CYP is administered to the patient.

8. The method of claim 1, wherein the selected CYP is CYP2C9 and a known inducer of the selected CYP is administered to the patient.

9. The method of claim 1, wherein the selected CYP is CYP2C19.

10. The method of claim 1, wherein the selected CYP is CYP2C9 or CYP2C19, the method further comprising:
    determining the patient has a poor metabolizer phenotype for the selected CYP.

11. A method of using metaxalone to treat a musculoskeletal condition, comprising:
    administering metaxalone to a human patient with a musculoskeletal condition;
    administering to the patient an active agent that is a substrate of a cytochrome p450 isozyme (CYP) selected from CYP1A2, CYP2B6, CYP2C9, CYP2C19, and CYP2D6;

determining the patient has increased plasma concentration of the active agent during administration with metaxalone; and altering dosing of the active agent during administration with metaxalone based on the determined increased plasma concentration of the active agent.

12. The method of claim 11, wherein the active agent has a narrow therapeutic index.

13. The method of claim 11, wherein the selected CYP is CYP2B6, CYP2C9, CYP2C19, or CYP2D6, the method further comprising:

determining the patient has a poor metabolizer phenotype for the selected CYP.

14. A method of using metaxalone to treat a musculoskeletal condition, comprising:

administering metaxalone to a human patient with a musculoskeletal condition;

administering to the patient an active agent that is a substrate of a cytochrome p450 (CYP) selected from CYP1A2 and CYP3A4;

determining the patient has a decreased plasma concentration of the active agent during administration with metaxalone; and altering dosing of the active agent during administration with metaxalone based on the determined decreased plasma concentration of the active agent.

15. The method of claim 14, wherein the active agent has a narrow therapeutic index.

16. The method of claim 14, wherein the selected CYP is CYP1A2.

17. The method of claim 14, wherein the selected CYP is CYP3A4.

18. The method of claim 11, wherein the selected CYP is CYP1A2.

19. The method of claim 11, wherein the selected CYP is CYP2B6.

20. The method of claim 11, wherein the selected CYP is CYP2C9.

21. The method of claim 11, wherein the selected CYP is CYP2C19.

22. The method of claim 11, wherein the selected CYP is CYP2D6.

23. The method of claim 1, wherein the selected CYP is CYP2C8 and a known inhibitor of the selected CYP is administered to the patient.

24. The method of claim 1, wherein the selected CYP is CYP2C9 and a known inhibitor of the selected CYP is administered to the patient.

* * * * *